United States Patent
Murphy et al.

(10) Patent No.: US 9,315,043 B2
(45) Date of Patent: Apr. 19, 2016

(54) AUTOMATED DEVICES, SYSTEMS, AND METHODS FOR THE FABRICATION OF TISSUE

(71) Applicant: Organovo, Inc., San Diego, CA (US)

(72) Inventors: Keith Murphy, Palos Verdes Estates, CA (US); Stephen Pentoney, Jr., Chino Hills, CA (US); Frank Lin, San Diego, CA (US); Vivian Gorgen, San Diego, CA (US); Clay Platt, Lake Forest, CA (US); Harry Scott Rapoport, San Diego, CA (US); Samir Damle, North Tustin, CA (US); Vaidehi Joshi, San Diego, CA (US); Sharon C. Presnell, Poway, CA (US)

(73) Assignee: Organovo, Inc., San Diego, CA (US)

( * ) Notice: Subject to any disclaimer, the term of this patent is extended or adjusted under 35 U.S.C. 154(b) by 0 days.

(21) Appl. No.: 14/796,910

(22) Filed: Jul. 10, 2015

(65) Prior Publication Data
US 2015/0314613 A1 Nov. 5, 2015

Related U.S. Application Data

(62) Division of application No. 14/447,412, filed on Jul. 30, 2014.

(60) Provisional application No. 61/860,644, filed on Jul. 31, 2013.

(51) Int. Cl.
*B29C 67/00* (2006.01)
*B41J 3/407* (2006.01)
(Continued)

(52) U.S. Cl.
CPC ............. *B41J 3/407* (2013.01); *B29C 67/0055* (2013.01); *B29C 67/0059* (2013.01); *B29C 67/0088* (2013.01); *B41J 2/04* (2013.01); *C12M 21/08* (2013.01); *C12M 25/00* (2013.01); *C12M 33/00* (2013.01); *C12M 33/12* (2013.01); *C12M 41/00* (2013.01); *A61F 2/00* (2013.01);
(Continued)

(58) Field of Classification Search
CPC ............ B29C 67/0055; B29C 67/0085; B29L 2031/7532
See application file for complete search history.

(56) References Cited

U.S. PATENT DOCUMENTS

| 4,759,764 A | 7/1988 | Fawcett et al. |
| 4,808,435 A | 2/1989 | Cropp et al. |

(Continued)

FOREIGN PATENT DOCUMENTS

| CA | 2306346 A1 | 1/1999 |
| EP | 2090584 A1 | 8/2009 |

(Continued)

OTHER PUBLICATIONS

Zhang, Yahui; Yu, Yin; Chen, Howard; Ozbolat, Ibrahim; "Characterization of printable cellular micro-fluidic channels for tissue engineering", Biofabrication, 5 (2013) 025004, published Mar. 5, 2013.*

(Continued)

*Primary Examiner* — Alison L Hindenlang
(74) *Attorney, Agent, or Firm* — Sterne, Kessler, Goldstein & Fox PLLC

(57) ABSTRACT

Described herein are improvements to bioprinting technology that facilitate automation of tissue and organ fabrication processes.

12 Claims, 35 Drawing Sheets

(51) Int. Cl.

| | |
|---|---|
| *C12M 1/34* | (2006.01) |
| *C12M 1/12* | (2006.01) |
| *C12M 1/26* | (2006.01) |
| *B41J 2/04* | (2006.01) |
| *C12M 3/00* | (2006.01) |
| *B33Y 30/00* | (2015.01) |
| *A61F 2/00* | (2006.01) |
| *B33Y 50/02* | (2015.01) |
| *B29L 31/00* | (2006.01) |

(52) U.S. Cl.
CPC .... *A61F 2240/00* (2013.01); *B29K 2995/0056* (2013.01); *B29L 2031/7532* (2013.01); *B33Y 30/00* (2014.12); *B33Y 50/02* (2014.12)

(56) References Cited

U.S. PATENT DOCUMENTS

| | | | |
|---|---|---|---|
| 5,099,090 | A | 3/1992 | Allan et al. |
| 6,315,469 | B1 | 11/2001 | Alvarez et al. |
| 6,401,795 | B1 | 6/2002 | Cesarano, III et al. |
| 6,454,972 | B1 | 9/2002 | Morisette et al. |
| 6,520,997 | B1 | 2/2003 | Pekkarinen et al. |
| 6,537,567 | B1 | 3/2003 | Niklason et al. |
| 6,561,607 | B1 | 5/2003 | Lubinsky et al. |
| 6,642,243 | B1 | 11/2003 | Imanzahrai |
| 6,713,772 | B2 | 3/2004 | Goodman et al. |
| 6,939,489 | B2 | 9/2005 | Moszner et al. |
| 6,942,830 | B2 | 9/2005 | Muelhaupt et al. |
| 6,979,670 | B1 | 12/2005 | Lyngstadaas et al. |
| 6,986,739 | B2 | 1/2006 | Warren et al. |
| 7,051,654 | B2 | 5/2006 | Boland et al. |
| 7,196,842 | B2 | 3/2007 | Weigl et al. |
| 7,484,837 | B2 | 2/2009 | Koga et al. |
| 7,625,198 | B2 | 12/2009 | Lipson et al. |
| 7,651,665 | B2 | 1/2010 | Gonzalez et al. |
| 7,680,555 | B2 | 3/2010 | Dunn et al. |
| 7,767,446 | B2 | 8/2010 | Robbins et al. |
| 8,143,055 | B2 | 3/2012 | Forgacs et al. |
| 8,241,905 | B2 | 8/2012 | Forgacs et al. |
| 8,343,740 | B2 | 1/2013 | Gonda et al. |
| 8,580,546 | B2 | 11/2013 | Gonda et al. |
| 8,728,807 | B2 | 5/2014 | Forgacs et al. |
| 8,747,880 | B2 | 6/2014 | Forgacs et al. |
| 8,852,932 | B2 | 10/2014 | Forgacs et al. |
| 8,931,880 | B2 | 1/2015 | Murphy et al. |
| 2001/0042942 | A1 | 11/2001 | Hizumi et al. |
| 2002/0171178 | A1 | 11/2002 | Dean et al. |
| 2002/0182633 | A1 | 12/2002 | Chen et al. |
| 2002/0188349 | A1 | 12/2002 | McAllister et al. |
| 2003/0049839 | A1 | 3/2003 | Romero-Ortega et al. |
| 2003/0149505 | A1 | 8/2003 | Mogensen |
| 2003/0153078 | A1 | 8/2003 | Libera et al. |
| 2003/0175410 | A1 | 9/2003 | Campbell et al. |
| 2003/0236588 | A1 | 12/2003 | Jang et al. |
| 2004/0006405 | A1 | 1/2004 | Chen et al. |
| 2004/0096966 | A1 | 5/2004 | Ingram |
| 2004/0132184 | A1 | 7/2004 | Dennis et al. |
| 2004/0197367 | A1 | 10/2004 | Rezania et al. |
| 2004/0219133 | A1 | 11/2004 | Lyles |
| 2004/0237822 | A1 | 12/2004 | Boland et al. |
| 2004/0253365 | A1 | 12/2004 | Warren et al. |
| 2005/0009178 | A1 | 1/2005 | Yost et al. |
| 2005/0169962 | A1 | 8/2005 | Bhatia et al. |
| 2005/0226856 | A1 | 10/2005 | Ahlfors |
| 2005/0276791 | A1 | 12/2005 | Hansford et al. |
| 2006/0099287 | A1 | 5/2006 | Kim et al. |
| 2006/0198918 | A1 | 9/2006 | Koyagi et al. |
| 2006/0237880 | A1 | 10/2006 | Wicker et al. |
| 2006/0270032 | A1 | 11/2006 | Bhatia et al. |
| 2007/0142916 | A1 | 6/2007 | Olson et al. |
| 2007/0200276 | A1 | 8/2007 | Mackey et al. |
| 2007/0231787 | A1 | 10/2007 | Voelker |
| 2007/0299508 | A1 | 12/2007 | Morrison et al. |
| 2008/0027114 | A1 | 1/2008 | Funke et al. |
| 2008/0070304 | A1 | 3/2008 | Forgacs et al. |
| 2008/0097575 | A1 | 4/2008 | Cottone |
| 2008/0192074 | A1 | 8/2008 | Dubois et al. |
| 2008/0193910 | A1 | 8/2008 | Larkin et al. |
| 2009/0076531 | A1 | 3/2009 | Richardson et al. |
| 2009/0117087 | A1 | 5/2009 | Carroll et al. |
| 2009/0142307 | A1 | 6/2009 | Athanasiou et al. |
| 2009/0206522 | A1 | 8/2009 | Hein et al. |
| 2009/0208466 | A1 | 8/2009 | Yoo et al. |
| 2009/0208577 | A1 | 8/2009 | Xu et al. |
| 2009/0239302 | A1 | 9/2009 | Decher et al. |
| 2009/0248145 | A1 | 10/2009 | Chan et al. |
| 2009/0263849 | A1 | 10/2009 | Sun et al. |
| 2009/0267269 | A1 | 10/2009 | Lim et al. |
| 2010/0041134 | A1 | 2/2010 | Forgacs et al. |
| 2010/0056390 | A1 | 3/2010 | Fischbach |
| 2010/0160183 | A1 | 6/2010 | Xu et al. |
| 2010/0191360 | A1 | 7/2010 | Napadensky et al. |
| 2010/0254900 | A1 | 10/2010 | Campbell et al. |
| 2011/0064784 | A1* | 3/2011 | Mullens ............ B82Y 30/00 424/443 |
| 2011/0172611 | A1 | 7/2011 | Yoo et al. |
| 2011/0177590 | A1 | 7/2011 | Clyne et al. |
| 2011/0180914 | A1 | 7/2011 | Do et al. |
| 2011/0212501 | A1 | 9/2011 | Yoo |
| 2011/0250688 | A1 | 10/2011 | Hasan |
| 2012/0045770 | A1 | 2/2012 | Pongracz et al. |
| 2012/0089238 | A1 | 4/2012 | Kang et al. |
| 2012/0116568 | A1 | 5/2012 | Murphy et al. |
| 2012/0196343 | A1 | 8/2012 | Forgacs et al. |
| 2012/0288938 | A1 | 11/2012 | Forgacs et al. |
| 2013/0108726 | A1 | 5/2013 | Uckelmann et al. |
| 2013/0164339 | A1 | 6/2013 | Murphy et al. |
| 2013/0190210 | A1 | 7/2013 | Murphy et al. |
| 2013/0193619 | A1 | 8/2013 | Church et al. |
| 2013/0236431 | A1 | 9/2013 | Gourdie et al. |
| 2013/0236879 | A1 | 9/2013 | Berry et al. |
| 2013/0345794 | A1 | 12/2013 | Khatiwala et al. |
| 2014/0012225 | A1 | 1/2014 | Yoo et al. |
| 2014/0012407 | A1 | 1/2014 | Murphy et al. |
| 2014/0044822 | A1 | 2/2014 | Mulliken |
| 2014/0093932 | A1 | 4/2014 | Murphy et al. |
| 2014/0099709 | A1 | 4/2014 | Presnell et al. |
| 2014/0131313 | A1 | 5/2014 | Wakamatsu et al. |
| 2014/0220685 | A1 | 8/2014 | Forgacs et al. |
| 2014/0265049 | A1 | 9/2014 | Burris et al. |
| 2014/0274802 | A1 | 9/2014 | Shepherd et al. |
| 2014/0287960 | A1 | 9/2014 | Shepherd et al. |
| 2014/0358273 | A1 | 12/2014 | Labossiere et al. |
| 2015/0004273 | A1 | 1/2015 | Forgacs et al. |
| 2015/0037445 | A1 | 2/2015 | Murphy et al. |
| 2015/0057786 | A1 | 2/2015 | Murphy et al. |

FOREIGN PATENT DOCUMENTS

| | | |
|---|---|---|
| JP | 2001038981 A | 2/2001 |
| JP | 2005031144 A | 2/2005 |
| JP | 2006159117 A | 6/2006 |
| KR | 20090087748 A | 8/2009 |
| RU | 2371758 C2 | 10/2009 |
| WO | WO-9901538 A1 | 1/1999 |
| WO | WO-0168811 A2 | 9/2001 |
| WO | WO-2004108418 A1 | 12/2004 |
| WO | WO-2005025493 A2 | 3/2005 |
| WO | WO-2005081970 A2 | 9/2005 |
| WO | WO-2007076272 A2 | 7/2007 |
| WO | WO-2007115336 A2 | 10/2007 |
| WO | WO-2007115337 A2 | 10/2007 |
| WO | WO-2007124023 A2 | 11/2007 |
| WO | WO-2007125893 A1 | 11/2007 |
| WO | WO-2007126411 A2 | 11/2007 |
| WO | WO-2007136936 A2 | 11/2007 |
| WO | WO-2009102484 A2 | 8/2009 |
| WO | WO-2009154466 A1 | 12/2009 |
| WO | WO-2010008905 A2 | 1/2010 |
| WO | WO-2011038373 A2 | 3/2011 |
| WO | WO-2011088213 | 7/2011 |
| WO | WO-2011097330 A2 | 8/2011 |
| WO | WO-2011107599 A1 | 9/2011 |

(56) References Cited

FOREIGN PATENT DOCUMENTS

| WO | WO-2011119059 A1 | 9/2011 |
|---|---|---|
| WO | WO-2012003465 A2 | 1/2012 |
| WO | WO-2012054195 A2 | 4/2012 |
| WO | WO-2012131000 A1 | 10/2012 |
| WO | WO-2013130823 A1 | 9/2013 |
| WO | WO-2013192290 A1 | 12/2013 |

OTHER PUBLICATIONS

Baltich et al. Development of a Scaffoldless Three-Dimensional Engineered Nerve Using a Nerve-Fibroblast Co-Culture. In Vitro Cell. Dev. Biol.—Animal, 2010 46:438-444.
Bioscaffolder 2008, www.syseng.de, SYSENG Dipl.—Ing. Hendrik John.
Boland et al. Application of inkjet printing to tissue engineering. Biotech J. 1:910-917 (2006).
Boland et al. Cell and Organ Printing 2: Fusion of Cell Aggregates in Three-Dimensional Gels. The Anatomical Record, Part A. 272A:497-502 (2003).
Bunnell et al. Adipose-derived Stem Cells: Isolation, Expansion and Differentiation. Methods 45(2):115-120 (2008).
Chaterji et al. Scaffold-Free In Vitro Arterial Mimetics: The Importance of Smooth Muscle-Endothelium Contact. Tissue Engineering Part A 16(8):1901-1912 (2010).
'Sciperio, Inc. 2003 R&D 100 Award Winner. Sciperio, http://www.sciperio.com/news/20031016.asp, accessed on Feb. 1, 2005, 2 pages.
Constans. Body by Science. The Scientist 17(19):34-37 http://www.the-scientist.com/article/display/141541 (2003).
Constans, Body by Science. The Scientist. 17(19):34-37. http://www.the-scientist.com/article/display/141541 (Oct. 6, 2003).
Co-pending U.S. Appl. No. 14/678,392, filed Apr. 3, 2015.
Dai et al. Fibroblast Aggregation by Suspension with Conjugates of Poly(ethylene glycol) and RGD. Biotechnology and Bioengineering 50(4):349-356 (May 20, 1996).
Dominici et al. Minimal criteria for defining multipotent mesenchymal stromal cells, International Society for Cellular Therapy position statement. Cytotherapy 8(4):315-317 (2006).
Edelman. Vascular Tissue Engineering: Designer Arteries. Circ Res 85(12):1115-1117 (1999).
Eisenberg et al. Bone Marrow Cells Transdifferentiate to Cardiomyocytes When Introduced into the Embryonic Heart. Stem Cells 24:1236-1245 (2006).
Fedorovich et al. Distinct Tissue Formation by Heterogeneous Printing of Osteo- and Endothelial Progenitor Cells. Tissue Engineering: Part A 17(15-16):2113-2123 (2011).
Fedorovich et al. Three-Dimensional Fiber Deposition of Cell-Laden, Viable Patterned Constructs for Bone Tissue Printing, Tissue Engineering: Part A 14(1):127-135 (2008).
Forgacs et al. Biological Relevance of Tissue Liquidity and Viscoelasticity Eds. A. Deutsch, M. Falcke, J. Howard and W. Zimmermann. Birkhauser. pp. 269-277 (2004).
Forgacs et al. Viscoelastic Properties of Living Embryonic Tissues: A Quantitative Study, Biophysical Journal 74(5):2227-2234 (May 1998).
Foty et al. Surface Tensions of Embryonic Tissues Predict Their Mutual Envelopment Behavior. Development 122(5):1611-1620 (1996).
Foty et al. The Differential Adhesion Hypothesis: A Direct Evaluation. Developmental Biology 278(1):255-263 (2005).
Frisman et al. Nanostructuring of PEG-fibrinogen polymeric scaffolds. Acta Biomaterialia 6(7):2518-2524 (2009).
Fuellhase et al. 264 Generation of Organized Bladder Tissue Constructs Using a Novel Hybrid Printing System. European Urology Supplements 8(4):186 (2009).
Furukawa et al. Formation of Human Fibroblast Aggregates (Spheroids) by Rotational Culture. Cell Transplantation 10(4-5):441-445 (2001).
Furukawa et al. Scaffold-free cartilage tissue by mechanical stress loading for tissue engineering. In Tissue Engineering, ed by Daniel Eberli. InTech 2010, p. 409-428.
Furukawa et al. Tissue-engineered Skin Using Aggregates of Normal Human Skin Fibroblasts and Biodegradable Material. J. MK Organs 4:353-356 (2001).
Ghorbanian et al. Microfluidic direct writer with integrated declogging mechanism for fabricating cell-laden hydrogel constructs. Biomed Microdevices (doi: 10.1007/s10544-014-9842-8), Springer Science+Business Media New York 2014 (Mar. 4, 2014).
Glazier et al. Simulation of the Differential Adhesion Driven Rearrangement of Biological Cells. Physical Review E 47(3):2128-2154 (Mar. 1993).
Glicklis et al. Modeling Mass Transfer in Hepatocyte Spheroids Via Cell Viability, Spheroid Size, and Hepatocellular Functions. Biotechnology and Bioengineering 86(6):672-680 (Jun. 20, 2004).
Graner et al. Simulation of Biological Cell Sorting Using a Two-Dimensional Extended Potts Model. Physical Review Letters 69(13):2013-2016 (Sep. 28, 1992).
Gruene et al. Laser Printing of Stem Cells for Biofabrication of Scaffold-Free Autologous Grafts. Tissue Engineering: Part C 17(1):79-89 (2011).
Gruene et al. Laser printing of three-dimensional multicellular arrays for studies of cell-cell and cell-environment interactions. Tissue Eng Part C Methods 17(10):973-82 (Oct. 2011).
Guenard et al. Syngeneic Schwann Cells Derived from Adult Nerves Seeded in Semipermeable Guidance Channels Enhance Peripheral Nerve Regeneration. The Journal of Neuroscience 12(9):3310-3320 (Sep. 1992).
Guillemot et al. High-throughput laser printing of cells and biomaterials for tissue engineering. Acta biomaterialia 6:2494-2500 (2010).
Hadlock et al. A Polymer Foam Conduit Seeded with Schwann Cells Promotes Guided Peripheral Nerve Regeneration. Tissue Engineering 6(2):119-127 (2000).
Halley et al. Growing Organs in the Lab. Longevity. 1-7 (Jun. 2009).
Harvey et al. Schwann cells and fetal tectal tissue cografted to the midbrain of newborn rats: fate of Schwann cells and their influence on host retinal innervation of grafts. Exp Neurol. 134(2):179-91 (1995).
Hockaday et al. Rapid 3D printing of anatomically accurate and mechanically heterogeneous aortic valve hydrogel scaffolds. Biofabrication 4(3):1-12 (2012).
Hubbard et al. Bioengineered, Autologous, Scaffold-free Nerve Conduit for Peripheral Nerve Repair. Abstract. AAHS/ASPN/ASRM 2011, Annual Scientific Meetings Program Book. pp. 140 and 159 (Jan. 12-18, 2011).
Ito et al. Novel Methodology for Fabrication of Tissue-Engineered Tubular Constructs Using Magnetite Nanoparticles and Magnetic Force, Tissue Engineering, Larchmont, NY, US, 11(9-10):1553-1561 (2005).
Iwasaki et al. Bioengineered Three-Layered Robust and Elastic Artery Using Hemodynamically-Equivalent Pulsatile Bioreactor. Circulation 18(14 Suppl):S53-S57 (2008).
Izaguirre et al. CompuCell, a multi-model framework for simulation of morphogenesis. Bioinformatics 20(7):1129-1137 (2004).
Jakab et al. Engineering Biological Structures of Prescribed Shape Using Self-assembling Multicellular Systems. PNAS USA 101:2864-2869 (2004).
Jakab et al. Organ printing: fiction or science. Biorheology 43(3-4):371-375 (2004).
Jakab et al. Relating Cell and Tissue Mechanics: Implications and Applications. Developmental Dynamics 237:2438-2449 (2008).
Jakab et al. Three-dimensional tissue constructs built by bioprinting. Biorheology 43(3-4):509-513 (2006).
Jakab et al. Tissue Engineering by Self- Assembly and Bio-printing of living cells. Biofabrication 2(2):022001 (14 pp) (Jun. 2, 2010).
Jakab et al. Tissue Engineering by Self-Assembly of Cells Printed into Topologically Defined Structures. Tissue Engineering: Part A. 14:413-421 (Nov. 3, 2008).
Kasko. Degradable Poly(ethylene glycol) Hydrogels for 2D and 3D Cell Culture. Aldrich Materials Science, pp. 67-75 (no date available).

(56) References Cited

OTHER PUBLICATIONS

Kelm et al. Design of Custom-Shaped Vascularized Tissues Using Microtissue Spheriods as Minimal Building Units. Tissue Engineering 12(8):2151-2160 (2006).
Kelm et al. Microscale Tissue Engineering Using Gravity-Enforced Cell Assembly. TRENDS in Biotechnology 22(4):195-202 (Apr. 2004).
Khatiwala et al. 3D Cell Bioprinting for Regenerative Medicine Research and Therapies. Gene Therapy and Regulation 7(1):1-19 (2012).
King et al. Development of 3D bioprinted human breast cancer for in vitro screening of therapeutics targeted against cancer progression. IEEE The American Society for Cell biology. 2013 ascb annual meeting. New Orleans: IEEE Dec. 14-18, 2013.
Koibuchi et al. Behavior of Cells in Artificially Made Cell Aggregates and Tissue Fragments after Grafting to Developing Hind Limb Buds in Xenopus laevis. The International Journal of Developmental Biology 43(2):141-148 (1999).
Korff et al. Blood Vessel Maturation in a 3-Dimensional Spheroidal Coculture Model: Direct Contact with Smooth Muscle Cells Regulates Endothelial Cell Quiescence and Abrogates VEGF Responsiveness. The FASEB Journal 15:447-457 (Feb. 2001).
Larkin et al. Structure and Functional Evaluation of Tendon-Skeletal Muscle Constructs Engineered in Vitro. Tissue Eng. 12(11):3149-3158 (Nov. 2006).
Lee et al. Multi-layered Culture of Human Skin Fibroblasts and Keratinocytes Through Three-dimensional Freeform Fabrication. Biomaterials 30:1587-1595 (2009).
L'Heureux et al. A completely biological tissue-engineered human blood vessel. The FASEB Journal 12 (1):47-56 (1998).
L'Heureux et al. Human tissue-engineered blood vessels for adult arterial revascularization. Nature Medicine 12 (3):361-365 (2006).
L'Heureux et al. Sheet-Based Tissue Engineering From Bench Top to the First Clinical Use of a Completely Biological Tissue Engineered Vessel. The FASEB Journal 12(1):47-56 (Abstract) (2006).
Luo et al. Three-dimensional microtissue assay for high-throughput cytotoxicity of nanoparticles. Anal Chem. 84(15):6731-6738 (Aug. 7, 2012).
Marga et al. Bioprint Engineered Fully Biological Nerve Graft. Poster Presentation TERMIS Dec. 5-8, 2010, Orlando, Florida, 1 page.
Marga et al. Construction of a Bioprinted Fully Biological Nerve Graft. Biophysical Journal 96(3 supp 1):643a Abstract (Feb. 2009).
Marga et al. Developmental Biology and Tissue Engineering, Birth Defects Research (Part C) 81:320-328 (2007).
Marga et al. Engineered Fully Biological Nerve Graft. Poster Presentation Biophysical Society Meeting, Mar. 4, 2009, 1 page.
Marga et al. Toward Engineering Functional Organ Modules by Additive Manufacturing. Biofabrication 4:022001 (12 pp) (2012).
Martin et al. Computer-Based Technique for Cell Aggregation Analysis and Cell Aggregation in In Vitro Chondrogenesis. Cytometry 28(2):141-146 (1997).
McGuigan et al. Vascularized organoid engineered by modular assembly enables blood perfusion. PNAS, 103(31):11461-11466 (2006).
Mehesz et al. Scalable robotic biofabrication of tissue spheroids. Biofabrication 3:1-8 (2011).
Mironov et al. Bioprinting Living Structures. J. Mat. Chem. 17:2054-2060 (2007).
Mironov et al. Organ Printing: Computer-Aided Jet-Based 3D Tissue Engineering. TRENDS in Biotechnology 21(4):157-161 (Apr. 2003).
Mironov et al. Organ printing: self-assembling cell aggregates as a "bioink". Science and Medicine 9:69-71 (2003).
Mironov et al. Organ Printing: Self-Assembling Cell Aggregates as 'Bioink'. Science & Medicine 9(2):69-71 (Apr. 2003).
Mironov et al. Organ Printing: Tissue Spheroids as Building Blocks. Biomaterials 30:2164-2174 (2009).
Mizumoto et al. Formation of Cylindrical Multicellular Aggregate (Cylindroid) and Express of Liver Specific Functions of Primary Rat Hepatocytes. Cytotechnology 31:69-75 (1999).
Mombach et al. Quantitative Comparison Between Differential Adhesion Models and Cell Sorting in the Presence and Absence of Fluctuations. Physical Review Letters 75(11):2244-2247 (Sep. 11, 1995).
Moon et al. Layer by Layer Three-dimensional Tissue Epitaxy by Cell-Laden Hydrogel Droplets. Tissue Engineering Part C: Methods 16(1):157-166 (2010).
Mroue et al. Three-dimensional cultures of mouse mammary epithelial cells. Methods Mol Biol. 945:221-250 (2013).
Neagu et al. Role of physical mechanisms in biological self-organization. Phys RevLett 95(17):178104 (2005).
Newman et al. Before programs: the physical origination of multicellular forms. Int J Dev Biol. 50(2-3):289-299 (2006).
Nickerson et al. Three-Dimensional Tissue Assemblies: Novel Models for the Study of *Salmonella enterica* Serovar Typhimurium Pathogenesis. Infection and Immunity 69(11):7106-7120 (Nov. 2001).
Niklason et al. Advances in Tissue Engineering of Blood Vessels and Other Tissues. Transpl. Immunol. 5(4):303-306 (1997).
Norotte et al. Scaffold-free vascular tissue engineering using bioprinting. Biomaterials 30:5910-5917 (2009).
Panagiotis et al. A unique aged human retinal pigmental epithelial cell line useful for studying lens differentiation in vitro. International Journal of Developmental Biology 45:753-758 (2001).
Pathology Outlines: Bladder. Normal Histology. pp. 1-4 (2011).
Paul et al. How to improve R&D productivity: the pharmaceutical industry's grand challenge. Nature Reviews Drug Discovery 9(3):203-214 (2010).
PCT/US2005/05735 International Search Report mailed Dec. 7, 2007.
PCT/US2005/05735 International Preliminary Report on Patentability dated Mar. 3, 2009.
PCT/US2009/48530 International Preliminary Report on Patentability dated Jan. 13, 2011.
PCT/US2009/48530 International Search Report mailed Mar. 15, 2010.
PCT/US2011/023520 International Preliminary Report on Patentability dated Aug. 16, 2012.
PCT/US2011/023520 International Search Report dated Oct. 31, 2011.
PCT/US2011/028713 International Preliminary Report on Patentability dated Sep. 18, 2012.
PCT/US2011/028713 International Search Report dated Nov. 30, 2011.
PCT/US2011/053515 International Preliminary Report on Patentability dated May 3, 2013.
PCT/US2011/053515 International Search Report and Written Opinion dated May 1, 2012.
PCT/US2012/054923 International Preliminary Report on Patentability dated Mar. 20, 2014.
PCT/US2012/054923 International Search Report mailed Feb. 26, 2013.
PCT/US2012/054935 International Preliminary Report on Patentability Mar. 20, 2014.
PCT/US2012/054935 International Search Report mailed Feb. 28, 2013.
PCT/US2013/036479 International Preliminary Report on Patentability dated Oct. 21, 2014.
PCT/US2013/036479 International search report mailed Jul. 25, 2013.
PCT/US2013/046519 International Preliminary Report on Patentability dated Dec. 23, 2014.
PCT/US2013/046519 International Search Report mailed Sep. 5, 2013.
PCT/US2014/026679 International Search Report and Written Opinion dated Jul. 22, 2014.
PCT/US2014/041419 International Search Report and Written Opinion dated Jan. 2, 2015.
PCT/US2014/048962 International Search Report and Written Opinion dated Nov. 10, 2014.

(56) References Cited

OTHER PUBLICATIONS

Perez-Pomares et al. Tissue Fusion and Cell Sorting in Embryonic Development and Disease: Biomedical Implications. Bioessays 28:809-821 (2006).
Remuzzi et al. Vascular Smooth Muscle Cells on Hyaluronic Acid: Culture and Mechanical Characterization of an Engineered Vascular Construct. Tissue Engineering 10(516):699-710 (2004).
Riken. Self-healing hydrogels ease into production. Research Highlights: Materials. Downloaded from the Riken website: <http://www.riken.jp/en/research/rikenresearch/highlights/7543/> (Nov. 1, 2013) [accessed Apr. 27, 2015].
Ryan et al. Tissue Spreading on Implantable Substrates is a Competitive Outcome of Cell-Cell vs. Cell-Substratum Adhesivity. PNAS 98(8):4323-4327 (Apr. 10, 2001).
Schuster et al. Why Drugs Fail—A Study on Side Effects in New Chemical Entities. Curr. Pharm. Des. 11:3545 (2005).
Shafrir et al. Mechanotransduction through the cytoskeleton. American Journal of Physiology 282:479-486 (2002).
Sheehan et al. Recent Patents and Trends in Bioprinting. Recent Patents on Biomedical Engineering 4:26-32 (2011).
Shim et al. Bioprinting of a mechanically enhanced three-dimensional dual cell-laden construct for osteochondral tissue engineering using a multi-head tissue/organ building system. J of Micromechanics and Microengineering. 22(Article No. 085014):1-11 (2012).
Siemionow et al. Current Techniques and Concepts in Peripheral Nerve Repair. Chapter 8, International Review of Neurobiology, 87:141-172 (2009).
Skardal et al. Bioprinting vessel-like constructs using hyaluronan hydrogels crosslinked with tetrahedral polyethylene glycol tetracrylates. Biomaterials 31:6173-6181 (2010).
Smith. A direct-write three-dimensional Bioassembly tool for regenerative medicine. The University of Arizona pp. 1-291 (Nov. 1, 2005).
Smith et al. Characterizing Environment Factors that Impact the Viability of Tissue-Engineered Constructs Fabricated by a Direct-Write Bioassembly Tool. Tissue Engineering, 13(2):373-385 (2007).
Smith et al. Three-Dimensional BioAssembly Tool for Generating Viable Tissue-Engineered Constructs. Tissue Engineering 10(9/10):1566-1576 (2004).
Steinberg. Does Differential Adhesion Govern Self-Assembly Processes in Histogenesis? Equilibrium Configurations and the Emergence of a Hierarchy Among Populations of Embryonic Cells. The Journal of Experimental Zoology 173(4):395-433 (Apr. 1970).
Steinberg et al. Liquid Behavior of Embryonic Tissues. Cell Behaviour pp. 583-697 (1982).
Stiles. UA Wins R & D 100 Award for Machine that Prints Tissue Cell-by-Cell. UANews Dec. 2, 2003, http://uanews.org/cgi-binfflebObjects/UANews.woa/wa/goPrint?ArticleID=8305, accessed on Feb. 1, 2005, 2 pages.
Tang et al. Molding of Three-Dimensional Microstructures of Gels. Journal of the American Chemical Society 125(43):12988-12989 (Oct. 29, 2003).
Tao et al. Bio-printing of living organized tissues using an inkjet technology. Database Accession No. PREV200700335042. FASEB Journal 23(5):A636 (2007).
Timmins et al. Hanging-Drop Multicellular Spheroids as a Model of Tumour Angiogenesis. Angiogenesis 7(2):97-103 (2004).
Tsang. Three-Dimensional Tissue Fabrication, Advanced drug delivery reviews 56(11):1635-1647 (2004).
U.S. Appl. No. 10/590,446 Office action dated Jan. 6, 2011.
U.S. Appl. No. 10/590,446 Office action dated Sep. 1, 2011.
U.S. Appl. No. 10/666,836 Office action dated Oct. 28, 2004.
U.S. Appl. No. 11/227,489 Office action dated Dec. 10, 2008.
U.S. Appl. No. 11/227,489 Office action dated Jul. 8, 2009.
U.S. Appl. No. 13/020,000 Office action dated Dec. 31, 2012.
U.S. Appl. No. 13/020,000 Office action dated Jul. 3, 2013.
U.S. Appl. No. 13/246,428 Office Action dated Aug. 26, 2014.
U.S. Appl. No. 13/246,428 Office Action dated Jan. 14, 2015.
U.S. Appl. No. 13/402,215 Office Action dated Mar. 19, 2013.
U.S. Appl. No. 13/529,172 Office action dated Sep. 24, 2013.
U.S. Appl. No. 13/612,768 Office action dated Jul. 30, 2015.
U.S. Appl. No. 13/612,768 Office Action dated May 30, 2014.
U.S. Appl. No. 13/612,768 Office Action dated Nov. 17, 2014.
U.S. Appl. No. 13/612,768 Office Action dated Oct. 1, 2013.
U.S. Appl. No. 13/612,778 Office Action dated Apr. 28, 2014.
U.S. Appl. No. 13/612,778 Office Action dated Nov. 7, 2014.
U.S. Appl. No. 13/634,863 Office Action dated Jan. 28, 2015.
U.S. Appl. No. 13/794,368 Office Action dated May 8, 2015.
U.S. Appl. No. 13/794,368 Office Action dated Nov. 26, 2014.
U.S. Appl. No. 13/801,780 Office Action dated Jun. 5, 2015.
U.S. Appl. No. 13/801,780 Office Action dated Nov. 14, 2014.
U.S. Appl. No. 13/968,313 Office Action dated Jun. 26, 2014.
U.S. Appl. No. 14/295,226 Office Action dated May 7, 2015.
U.S. Appl. No. 14/295,226 Office Action dated Oct. 8, 2014.
U.S. Appl. No. 14/447,412 Office Action dated Jul. 15, 2015.
U.S. Appl. No. 14/447,412 Office Action dated Mar. 3, 2015.
U.S. Appl. No. 14/530,499 Office Action dated May 14, 2015.
Wake Forest Baptist Medical Center (Wake Forest Physician Reports First Human Recipients of Laboratory-Grown Organs. 2006 pp. 1-2).
Wang et al. Bone marrow mesenchymal stem cells promote cell proliferation and neurotrophic function of Schwann cells in vitro and in vivo. Brain Research 1262:7-15 (2009).
Xu et al. A three-dimensional in vitro ovarian cancer coculture model using a high-throughput cell patterning platform. Biotechnology Journal 6(2):204-212 (2011).
Xu et al. In vivo generation of functional tissues using the inkjet printing technology. Tissue Engineering 13(7):1713-1714 (2007).
Yamauchi et al. A Three-Dimensional Cell Culture Model for Bovine Endometrium: Regeneration of a Multicellular Spheroid Using Ascorbate. Placenta 24:258-269 (2003).
ATCC Product Catalog MCF7 (ATCC® HTB-22TM) https://www.atcc.org/products/all/HTB-22.aspx?slp=1#generalinformation, retrieved Sep. 18, 2015.
ATCC Product catalog Primary Subcutaneous Pre-adipocytes; Normal, Human (ATCC® PCS-210-01OTM) https://www.atcc.org/Products/All/PCS-210-010.aspx?slp=1, retrieved Sep. 18, 2015.
Co-pending U.S. Appl. No. 14/827,152, filed Aug. 14, 2015.
Co-pending U.S. Appl. No. 14/876,659, filed Oct. 6, 2015.
Dirat et al. Cancer-associated adipocytes exhibit an activated phenotype and contribute to breast cancer invasion. Cancer Res. 71(7):2455-2465 (2011).
Egebald et al. Tumors as organs: complex tissues that interface with the entire organism. Dev Cell. 18(6):884-901 (2010).
Grange et al. Isolation and characterization of human breast tumor-derived endothelial cells. Oncol Rep. 15(2):381-386 (2006).
Landers et al. Fabrication of soft tissue engineering scaffolds by means of rapid prototyping techniques. Journal of Materials Science 37:3107-3116 (2002).
Marga et al. Engineered Fully Biological Nerve Graft. Oral Presentation, International Conference on Biofabrication, Oct. 3-6, 2010, Philadelphia, Pennsylvania, 1 page.
PCT/US2014/026679 International Preliminary Report on Patentability dated Sep. 24, 2015.
U.S. Appl. No. 13/634,863 Office Action dated Sep. 8, 2015.
U.S. Appl. No. 13/794,368 Office Action dated Sep. 23, 2015.
U.S. Appl. No. 14/295,226 Office Action dated Sep. 9, 2015.
U.S. Appl. No. 14/678,392 Office Action dated Oct. 8, 2015.
U.S. Appl. No. 14/678,392 Office Action dated Sep. 24, 2015.
Zhang et al. Characterization of printable cellular micro-fluidic channels for tissue engineering Biofabrication 5:025004 (2013).
Co-pending U.S. Appl. No. 14/933,822, filed Nov. 5, 2015.
Co-pending U.S. Appl. No. 14/936,580, filed Nov. 9, 2015.
Cui et al. Direct Human Cartilage Repair Using Three-Dimensional Bioprinting Technology. Tissue Engineering Part A 18(11-12):1304-1312 (2012).
Fujita et al. Fabrication of scaffold-free contractile skeletal muscle tissue using magnetite-incorporated myogenic C2C12 cells. J Tissue Eng Regen Med. 4(6):437-443 (2010).
Hierlihy et al. The post-natal heart contains a myocardial stem cell population. FEBS Letters 530:239-243 (2002).
Pearson Education. Human Heart Illustration (2004).
Tanaka et al. A Valved Hepatic Portoduodenal Intestinal Conduit for Biliary Atresia. Ann. Surg. 213(3):230-235 (1991).
U.S. Appl. No. 13/612,778 Office Action dated Nov. 17, 2015.

(56) References Cited

OTHER PUBLICATIONS

U.S. Appl. No. 14/244,679 Office Action dated Oct. 23, 2015.
Co-pending U.S. Appl. No. 14/950,567, filed on Nov. 24, 2015.
Liu et al. Design and Development of Three-Dimensional Scaffolds For Tissue Engineering. Chemical Engineering Research and Design 85(7):1051-1064 (2007).
Tsang et al. Fabrication of 3D hepatic tissues by additive photopatterning of cellular hydrogels. The FASEB Journal 21(3):790-801 (2007).
Chang et al. Biofabrication of a three-dimensional liver micro-organ as an *in vitro* drug metabolism model. Biofabrication 2:045004 (2010).

* cited by examiner

EXTRUSION DEVICE

AUTOMATED DEVICES, SYSTEMS, AND METHODS FOR THE FABRICATION OF TISSUE

CROSS-REFERENCE TO RELATED APPLICATIONS

This application is a divisional of U.S. application Ser. No. 14/447,412, filed Jul. 30, 2014, and claims the benefit of U.S. Application Ser. No. 61/860,644, filed Jul. 31, 2013, both of which are hereby incorporated by reference in their entirety.

BACKGROUND OF INVENTION

A number of pressing problems confront the healthcare industry. As of June 2013, there were approximately 118,000 patients registered by United Network for Organ Sharing (UNOS) as needing an organ transplant. Between January and March 2013, only 6,891 transplants were performed. Each year more patients are added to the UNOS list than transplants are performed, resulting in a net increase in the number of patients waiting for a transplant. For example, as of 2011, over 15,000 people were registered as needing a liver graft/transplant; however only about 5,800 liver transplants were performed that year. In 2010, the median wait time for a liver was over 12 months.

Additionally, the research and development cost of a new pharmaceutical compound is approximately $1.8 billion. See Paul, et al. (2010). How to improve R&D productivity: the pharmaceutical industry's grand challenge. Nature Reviews Drug Discovery 9(3):203-214. Drug discovery is the process by which drugs are discovered and/or designed. The process of drug discovery generally involves at least the steps of: identification of candidates, synthesis, characterization, screening, and assays for therapeutic efficacy. Despite advances in technology and understanding of biological systems, drug discovery is still a lengthy, expensive, and inefficient process with low rate of new therapeutic discovery.

SUMMARY OF THE INVENTION

There is a need for tools and techniques that facilitate application of regenerative medicine and tissue engineering technologies to relieving the urgent need for tissues and organs. There is also a need for tools and techniques that substantially increase the number and quality of innovative, cost-effective new medicines, without incurring unsustainable R&D costs. The inventors describe herein improvements to devices, systems, and methods for fabricating tissues and organs that allow for enhanced speed, accuracy, and scalability. Specifically, the devices, systems, and methods described offer advantages including, but not limited to, improved scalability of production while maintaining control of the spatial orientation of materials, improved three-dimensional calibration of deposition equipment, and improved utilization of multiple distinct materials without significant interruption of a fabrication process.

In one aspect, disclosed herein are automated bioprinters comprising: a printer head comprising one or more cartridges, each cartridge comprising contents selected from: bio-ink, support material, and a combination thereof; and for each cartridge: an actuation means that vertically positions the cartridge relative to a receiving surface to produce a particular three-dimensional geometry in the dispensed contents of the cartridge, the actuation means operating independently from other actuation means; and a deposition orifice; a receiving surface for receiving dispensed contents of a cartridge; and a calibration means comprising a three-dimensional calibration system, the system comprising at least two lasers, a sensor fixed to the receiving surface for determining the position of the deposition orifice; and a sensor fixed to the printer head for determining the position of the receiving surface; whereby the system calculates a print height, the print height comprising the distance between the deposition orifice and the receiving surface; whereby a construct is bioprinted without stopping the bioprinter to manually replace one or more cartridges or to manually adjust the positioning of the printer head or the positioning of one or more of the cartridges. In some embodiments, the three-dimensional calibration system creates a topographical map of the receiving surface. In some embodiments, the three-dimensional calibration system creates a topographical map of the deposition orifice. In some embodiments, the three-dimensional calibration system monitors the print height during deposition of the contents of a cartridge. In some embodiments, the automated bioprinter further comprises at least one die, each die controlling simultaneous deposition of a plurality of constructs in parallel and arranged in a pattern, each construct having a particular three-dimensional geometry; deposition of a single construct having a particular three-dimensional geometry; or a combination thereof. In some embodiments, the automated bioprinter further comprises one or more multiaxial nozzles for controlling the deposition of one or more constructs having a particular three-dimensional geometry, wherein each multiaxial nozzle has dual or greater concentric flow capability with at least two independent inputs for at least two different materials and at least two independent outputs for the preparation of a multiaxial tube with a core layer and a mantle layer and optionally one or more intermediate layers in between the core and mantle layers, any two adjacent layers having different composition of materials with respect to each other and the materials being selected from bio-ink, support material, and a combination thereof. In further embodiments, each of the one or more multiaxial nozzles further comprises a means to independently regulate the flow of each of the at least two different materials through the at least two independent outputs. In still further embodiments, the means to independently regulate the flow of each of the at least two different materials through the at least two independent outputs allows for continuous extrusion or sputter extrusion. In some embodiments, one of the at least two different materials is removed after bioprinting to create one or more voids. In some embodiments, at least one cartridge further comprises a means to adjust and/or maintain the temperature of the cartridge.

In another aspect, disclosed herein are automated bioprinters comprising: a printer head comprising at least three cartridges, wherein (i) at least one cartridge comprises a capillary tube containing bio-ink; (ii) at least one cartridge comprises a needle containing bio-ink; (iii) at least one cartridge is configured for ink jet printing; and (iv) each cartridge comprises contents selected from bio-ink, support material, and a combination thereof; and a receiving surface for receiving dispensed contents of a cartridge; whereby a construct is bioprinted without stopping the bioprinter to manually replace one or more cartridges or to manually adjust the positioning of the printer head or the positioning of one or more of the cartridges. In some embodiments, the needle is in communication with a bio-ink reservoir, bio-ink deposition is by pneumatic displacement, and the bio-ink is a liquid or semi-solid composition. In some embodiments, the capillary tube deposits bio-ink through a positive displacement mechanism, and the bio-ink is a solid or semi-solid composition. In some embodiments, the automated bioprinter further comprises a calibration means comprising a three-dimensional calibration system, the system comprising at least two lasers, a sensor fixed to the receiving surface for determining the position of a deposition orifice; and a sensor fixed to the printer head for determining the position of the receiving surface; whereby the system calculates a print height, the print height comprising the distance between the deposition orifice and receiving surface. In some embodiments, the automated bioprinter further comprises at least one die, each die controlling simultaneous deposition of a plurality of constructs in parallel and arranged in a pattern, each construct having a particular three-dimensional geometry; deposition of a single construct having a particular three-dimensional geometry; or a combination thereof. In some embodiments, the automated bioprinter further comprises one or more multiaxial nozzles for controlling the deposition of one or more constructs having a particular three-dimensional geometry, wherein each multiaxial nozzle has dual or greater concentric flow capability with at least two independent inputs for at least two different materials and at least two independent outputs for the preparation of a multiaxial tube with a core layer and a mantle layer and optionally one or more intermediate layers in between the core and mantle layers, any two adjacent layers having different composition of materials with respect to each other and the materials being selected from bio-ink, support material, and a combination thereof. In some embodiments, at least one cartridge further comprises a means to adjust and/or maintain the temperature of the cartridge.

In another aspect, disclosed herein are automated bioprinters comprising: at least one die, each die controlling simultaneous deposition of a plurality of constructs in parallel and arranged in a pattern, each construct having a particular three-dimensional geometry; deposition of a single construct having a particular three-dimensional patterned geometry; or a combination thereof; whereby the single construct or plurality of constructs are bioprinted without stopping the bioprinter to manually replace or to manually adjust the positioning of one or more components of the bioprinter. In some embodiments, the die is permanently fixed. In some embodiments, the die is reversibly fixed. In some embodiments, the die controls simultaneous deposition of 2-384 constructs in parallel and arranged in a pattern. In some embodiments, the die is connected to one or more chambers for containing a uniform layer of bio-ink, support material, or a combination thereof. In some embodiments, the die controls simultaneous deposition of a plurality of materials in parallel. In further embodiments, the die comprises an input port for each material. In some embodiments, each construct in the plurality of constructs has the same three-dimensional geometry. In some embodiments, each of the constructs in the plurality of constructs is in contact with one another to form a single construct.

In another aspect, disclosed herein are automated bioprinters comprising one or more multiaxial nozzles for controlling the deposition of one or more constructs having a particular three-dimensional geometry, wherein each multiaxial nozzle has dual or greater concentric flow capability with at least two independent inputs for at least two different materials and at least two independent outputs for the preparation of a multiaxial tube with a core layer and a mantle layer and optionally one or more intermediate layers in between the core and mantle layers, any two adjacent layers having different composition of materials with respect to each other and the materials being selected from bio-ink, support material, and a combination thereof; whereby the one or more constructs are bioprinted without stopping the bioprinter to manually replace or to manually adjust the positioning of one or more components of the bioprinter. In some embodiments, each of the one or more multiaxial nozzles further comprises a means to independently regulate the flow of each of the at least two different materials through the at least two independent outputs. In further embodiments, the means to independently regulate the flow of each of the at least two different materials through the at least two independent outputs allows for continuous extrusion or sputter extrusion. In some embodiments, one of the at least two different materials is removed after bioprinting to create one or more voids. In some embodiments, one or more of the multiaxial nozzles are coaxial nozzles. In some embodiments, one or more of the multiaxial nozzles are triaxial nozzles.

In another aspect, disclosed herein are bioprinters comprising: one or more printer heads, wherein each printer head comprises a cartridge carrier for receiving and holding a plurality of cartridges, the cartridge carrier rotatable to align a selected cartridge with a drive pathway, each cartridge comprising contents selected from one or more of: bio-ink and support material; a drive means for dispensing the contents of the selected cartridge; a receiving surface for receiving dispensed contents of the selected cartridge; an actuation means for positioning the one or more printer heads relative to the receiving surface to produce a particular three-dimensional geometry in the dispensed contents of the selected cartridge; and a calibration means for determining the position of: 1) a deposition orifice associated with the selected cartridge, and 2) a print target surface supported by the receiving surface. In some embodiments, the drive means utilizes positive displacement, pneumatic displacement, hydraulic displacement, acoustic resonance, or a combination thereof to dispense the contents of a cartridge. In some embodiments, the cartridge carrier receives and holds 2-10 cartridges. In some embodiments, each printer head comprises a deposition orifice for each cartridge. In some embodiments, each printer head comprises a common deposition orifice for the plurality of cartridges. In some embodiments, the plurality of cartridges comprises a wash cartridge to decontaminate a dispensing path of the bioprinter. In some embodiments, the receiving surface is moved relative to the one or more printer heads to produce a particular three-dimensional geometry in the dispensed contents of the plurality of cartridges. In some embodiments, at least one of the cartridges is connected to a remote reservoir of contents. In some embodiments, at least one of the cartridges is a disposable, single-use cartridge. In some embodiments, the calibration means calculates a print height, the print height comprising the distance between a deposition orifice and the print target surface. In further embodiments, the calibration means monitors the print height during deposition of materials. In some embodiments, the calibration means utilizes one or more sensors selected from: triangulation sensors, ultrasonic distance sensing probes, and digital cameras. In some embodiments, the bio-ink comprises mammalian cells.

In another aspect, disclosed herein are cartridge carriers for a bioprinter, the cartridge carrier attached to a positionable printer head of the bioprinter and adapted to receive and hold a plurality of cartridges, each cartridge comprising contents selected from one or more of: bio-ink and support material, the cartridge carrier rotatable to align a selected cartridge with a drive pathway of the bioprinter such that a drive mechanism engages the selected cartridge to dispense said contents. In some embodiments, the cartridge carrier is adapted to receive and hold 2-10 cartridges.

In another aspect, disclosed herein are three-dimensional calibration systems for an automated bioprinter, the system comprising: a sensor fixed to a receiving surface of the bioprinter for determining the position of a deposition orifice of the bioprinter; and a sensor fixed to a printer head of the bioprinter for determining the position of a print target surface associated with the receiving surface; whereby the system calculates a print height, the print height comprising the distance between the deposition orifice and a print target surface. In some embodiments, the sensors are selected from: triangulation sensors, ultrasonic distance sensing probes, and digital cameras.

In another aspect, disclosed herein are bioprinters comprising: a printer head, the printer head comprising a means for receiving and holding a cartridge, the cartridge comprising contents selected from one or more of: bio-ink and support material; a drive means for dispensing the contents of the cartridge; a receiving surface for receiving dispensed contents of the cartridge; an actuation means for positioning the printer head relative to the receiving surface; and a die for controlling simultaneous deposition of a plurality of constructs in parallel, each construct having a particular three-dimensional geometry. In some embodiments, the drive means utilizes positive displacement, pneumatic displacement, hydraulic displacement, acoustic resonance, or a combination thereof to dispense the contents of a cartridge. In some embodiments, the printer head comprises a deposition orifice for the cartridge. In some embodiments, the receiving surface is moved relative to the one or more printer heads to produce a particular three-dimensional geometry in the dispensed contents of the cartridge. In some embodiments, the cartridge is connected to a remote reservoir of contents. In some embodiments, the cartridge is a disposable, single-use cartridge. In some embodiments, the bioprinter further comprises a calibration means for determining the position of: 1) a deposition orifice associated with the cartridge, and 2) a print target surface supported by the receiving surface. In further embodiments, the calibration means calculates a print height, the print height comprising the distance between a deposition orifice and the print target surface. In still further embodiments, the calibration means monitors the print height during deposition of materials. In further embodiments, the calibration means utilizes one or more sensors selected from: triangulation sensors, ultrasonic distance sensing probes, and digital cameras. In some embodiments, the die is permanently fixed. In some embodiments, the die is reversibly fixed. In some embodiments, the die controls simultaneous deposition of 2-384 constructs in parallel. In further embodiments, the die controls simultaneous deposition of 96 constructs in parallel. In still further embodiments, the die controls simultaneous deposition of 24 constructs in parallel. In still further embodiments, the die controls simultaneous deposition of 12 constructs in parallel. In some embodiments, the die is connected to a chamber for containing a uniform layer of bio-ink or support material. In some embodiments, the die controls simultaneous deposition of a plurality of materials in parallel. In further embodiments, the die comprises an input port for each material. In some embodiments, each construct in the plurality of constructs has the same three-dimensional geometry. In some embodiments, the bio-ink comprises mammalian cells.

In another aspect, disclosed herein are tissue constructs fabricated by the bioprinters described herein.

In another aspect, disclosed herein are dies for controlling materials deposited from a bioprinter, the die comprising: one or more input ports for receiving bio-ink or support material deposited from the bioprinter; and a plurality of output molds, each output mold comprising a well associated with each input port for shaping the bio-ink or support material; whereby the die allows simultaneous deposition of a plurality of constructs in parallel, each construct having a particular three-dimensional geometry. In some embodiments, the die controls simultaneous deposition of 2-384 constructs in parallel. In further embodiments, the die controls simultaneous deposition of 96 constructs in parallel. In still further embodiments, the die controls simultaneous deposition of 24 constructs in parallel. In still further embodiments, the die controls simultaneous deposition of 12 constructs in parallel. In some embodiments, the die is connected to a chamber for containing a uniform layer of bio-ink or support material, the chamber positioned between the die and a drive mechanism of the bioprinter. In some embodiments, the die controls simultaneous deposition of a plurality of materials in parallel.

In another aspect, disclosed herein are dies comprising one or more molds for stamping or cutting to shape one or more three-dimensional bioprinted tissues into a desired geometry.

In another aspect, disclosed herein are printer heads comprising: a plurality of cartridges, each cartridge comprising contents selected from: bio-ink, support material, and a combination thereof; a calibration means for determining the position of a deposition orifice associated with each cartridge; and for each cartridge: a means for receiving and holding the cartridge that aligns the cartridge with a drive pathway; a drive means that dispenses the contents of the cartridge, the drive means operating independently from other drive means; and an actuation means that vertically positions the cartridge relative to a receiving surface to produce a particular three-dimensional geometry in the dispensed contents of the cartridge, the actuation means operating independently from other actuation means; provided that the printer head is for a bioprinter. In various embodiments, each drive means utilizes positive displacement, pneumatic displacement, hydraulic displacement, acoustic resonance, or a combination thereof to dispense the contents of the cartridge.

In another aspect, disclosed herein are bioprinters comprising: a printer head comprising: a cartridge carrier for receiving and holding a plurality of cartridges, each cartridge comprising contents selected from: bio-ink, support material, and a combination thereof; and for each cartridge: a means for receiving and holding the cartridge that aligns the cartridge with a drive pathway; a drive means that dispenses the contents of the cartridge, the drive means operating independently from other drive means; an actuation means that vertically positions the cartridge relative to a receiving surface to produce a particular three-dimensional geometry in the dispensed contents of the cartridge, the actuation means operating independently from other actuation means; a receiving surface for receiving dispensed contents of a cartridge; and a calibration means for determining the position of: 1) a deposition orifice associated with each cartridge, and 2) a print target surface supported by the receiving surface. In various embodiments, each drive means utilizes positive displacement, pneumatic displacement, hydraulic displacement, acoustic resonance, or a combination thereof to dispense the contents of the cartridge.

BRIEF DESCRIPTION OF FIGURES

FIG. 8-1 illustrates a non-limiting schematic example of a two-part die fixed to a deposition mechanism; in this case, a die that controls the geometry of deposited material to facilitate deposition of multiple constructs in parallel.

FIG. 8-2 illustrates a non-limiting schematic example of the two-part die of FIG. 8-1; in this case, a schematic depicting the die attached to a chamber filled with a cell suspension forming a uniform layer of bio-ink, which is extruded though the die to form contiguous, hollow, cylindrical structures.

FIG. 9-1 illustrates a non-limiting schematic example of a centrifugal apparatus intended for spinning cartridges containing bio-ink to increase cell concentration from a suspension and a compatible cartridge; in this case, (a) a perspective view of a centrifugal apparatus; (b). a perspective view of a compatible cartridge; and (c) a schematic view along A-A of the compatible cartridge are shown.

FIG. 9-2 illustrates a non-limiting schematic example of a cartridge loaded onto an extrusion device.

FIG. 9-3 illustrates a non-limiting example of a die installed on a cartridge, for which bio-ink extruded through this die will form six contiguous, hollow, cylindrical structures; in this case, (a) a perspective view of a cartridge with installed die; (b) a schematic view along B-B of the cartridge with installed die; and (c) three different perspective views of the die itself are shown.

FIG. 23a illustrates a non-limiting example of a printer head with independent z-axis motion; in this case, the printer head has a z-axis positioning mechanism to adjust the location of an attached cartridge relative to the target printing surface and a drive mechanism to dispense the contents of the attached cartridge.

FIG. 23b illustrates a non-limiting example of the z-axis positioning mechanism to adjust the location of an attached cartridge relative to the target printing surface for the printer head shown in FIG. 23a.

DETAILED DESCRIPTION OF INVENTION

Figure 1:
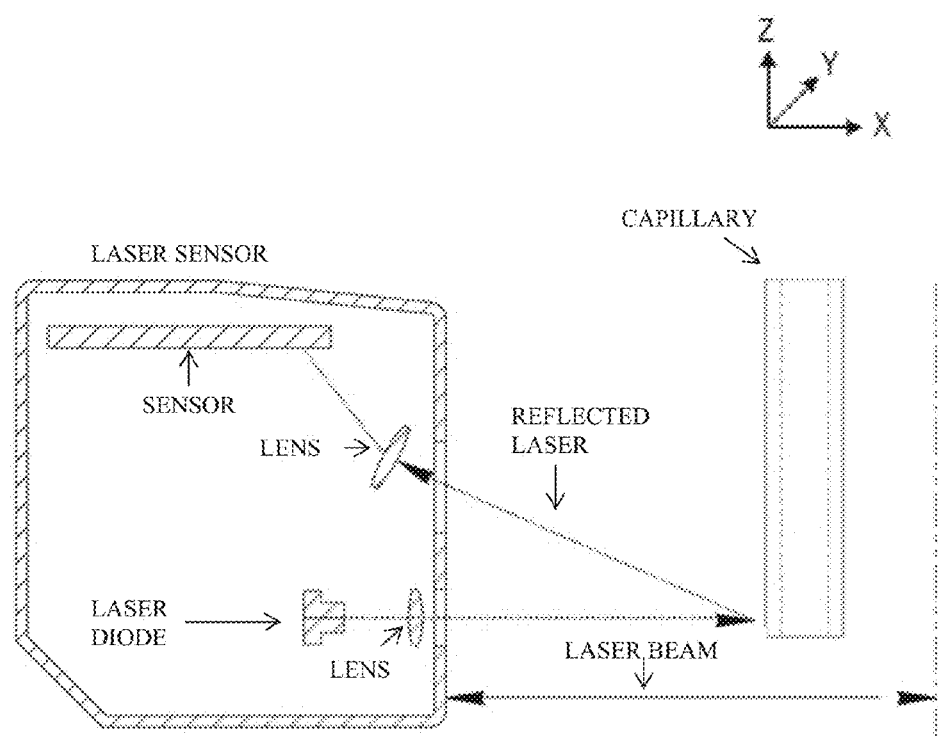
FIG. 1 illustrates a non-limiting example of a laser distance sensor mounted in the horizontal position.

The invention relates to the fields of regenerative medicine, tissue/organ engineering, biologic and medical research, and drug discovery. More particularly, the invention relates to improved devices for fabricating tissues and organs, systems and methods for calibrating and using such devices, and tissues and organs fabricated by the devices, systems, and methods disclosed herein. By way of example, the devices, systems, and methods described herein offer significant improvements to scalability of production while maintaining accuracy in the spatial positioning of materials through use of die and mold apparatus attached to a bioprinter that allows for bioprinting multiple constructs in parallel. By way of further example, the devices, systems, and methods described herein offer significant improvements to three-dimensional calibration of deposition equipment through use of sensors to rapidly and accurately determine the relative positions of a material deposition orifice and a target print surface including the height of a deposition orifice above a print surface. By way of still further example, the devices, systems, and methods described herein offer significant improvements to tissue fabrication with multiple distinct materials through use of a means to exchange print cartridges without performing a changeover operation and through the introduction of disposable, single-use print cartridges.

Disclosed herein, in certain embodiments, are automated bioprinters comprising: a printer head comprising one or more cartridges, each cartridge comprising contents selected from: bio-ink, support material, and a combination thereof; and for each cartridge: an actuation means that vertically positions the cartridge relative to a receiving surface to produce a particular three-dimensional geometry in the dispensed contents of the cartridge, the actuation means operating independently from other actuation means; and a deposition orifice; a receiving surface for receiving dispensed contents of a cartridge; and a calibration means comprising a three-dimensional calibration system, the system comprising at least two lasers, a sensor fixed to the receiving surface for determining the position of the deposition orifice; and a sensor fixed to the printer head for determining the position of the receiving surface; whereby the system calculates a print height, the print height comprising the distance between the deposition orifice and the receiving surface; whereby a construct is bioprinted without stopping the bioprinter to manually replace one or more cartridges or to manually adjust the positioning of the printer head or the positioning of one or more of the cartridges.

Also disclosed herein, in certain embodiments, are automated bioprinters comprising: a printer head comprising at least three cartridges, wherein (i) at least one cartridge comprises a capillary tube containing bio-ink; (ii) at least one cartridge comprises a needle containing bio-ink; (iii) at least one cartridge is configured for ink-jet printing; and (iv) each cartridge comprises contents selected from bio-ink, support material, and a combination thereof; and a receiving surface for receiving dispensed contents of a cartridge; whereby a construct is bioprinted without stopping the bioprinter to manually replace one or more cartridges or to manually adjust the positioning of the printer head or the positioning of one or more of the cartridges.

Also disclosed herein, in certain embodiments, are automated bioprinters comprising: at least one die, each die controlling simultaneous deposition of a plurality of constructs in parallel and arranged in a pattern, each construct having a particular three-dimensional geometry; deposition of a single construct having a particular three-dimensional patterned geometry; or a combination thereof; whereby the single construct or plurality of constructs are bioprinted without stopping the bioprinter to manually replace or to manually adjust the positioning of one or more components of the bioprinter.

Also disclosed herein, in certain embodiments, are automated bioprinters comprising one or more multiaxial nozzles for controlling the deposition of one or more constructs having a particular three-dimensional geometry, wherein each multiaxial nozzle has dual or greater concentric flow capability with at least two independent inputs for at least two different materials and at least two independent outputs for the preparation of a multiaxial tube with a core layer and a mantle layer and optionally one or more intermediate layers in between the core and mantle layers, any two adjacent layers having different composition of materials with respect to each other and the materials being selected from bio-ink, support material, and a combination thereof; whereby the one or more constructs are bioprinted without stopping the bioprinter to manually replace or to manually adjust the positioning of one or more components of the bioprinter.

Also disclosed herein, in certain embodiments, are bioprinters comprising: one or more printer heads, wherein each printer head comprises a cartridge carrier for receiving and holding a plurality of cartridges, the cartridge carrier rotatable to align a selected cartridge with a drive pathway, each cartridge comprising contents selected from one or more of: bio-ink and support material; a drive means for dispensing the contents of the selected cartridge; a receiving surface for receiving dispensed contents of the selected cartridge; an actuation means for positioning the one or more printer heads relative to the receiving surface to produce a particular three-dimensional geometry in the dispensed contents of the selected cartridge; and a calibration means for determining the position of: 1) a deposition orifice associated with the selected cartridge, and 2) a print target surface supported by the receiving surface.

Also disclosed herein, in certain embodiments, are cartridge carriers for a bioprinter, the cartridge carrier attached to a positionable printer head of the bioprinter and adapted to receive and hold a plurality of cartridges, each cartridge comprising contents selected from one or more of: bio-ink and support material, the cartridge carrier rotatable to align a selected cartridge with a drive pathway of the bioprinter such that a drive mechanism engages the selected cartridge to dispense said contents.

Also disclosed herein, in certain embodiments, are three-dimensional calibration systems for an automated bioprinter, the system comprising: a sensor fixed to a receiving surface of the bioprinter for determining the position of a deposition orifice of the bioprinter; and a sensor fixed to a printer head of the bioprinter for determining the position of a print target surface associated with the receiving surface; whereby the system calculates a print height, the print height comprising the distance between the deposition orifice and a print target surface.

Also disclosed herein, in certain embodiments, are bioprinters comprising: a printer head, the printer head comprising a means for receiving and holding a cartridge, the cartridge comprising contents selected from one or more of: bio-ink and support material; a drive means for dispensing the contents of the cartridge; a receiving surface for receiving dispensed contents of the cartridge; an actuation means for positioning the printer head relative to the receiving surface; and a die for controlling simultaneous deposition of a plurality of constructs in parallel, each construct having a particular three-dimensional geometry.

Also disclosed herein, in certain embodiments, are tissue constructs fabricated by the bioprinters described herein.

Also disclosed herein, in certain embodiments, are dies for controlling materials deposited from a bioprinter, the die comprising: one or more input ports for receiving bio-ink or support material deposited from the bioprinter; and a plurality of output molds, each output mold comprising a well associated with each input port for shaping the bio-ink or support material; whereby the die allows simultaneous deposition of a plurality of constructs in parallel, each construct having a particular three-dimensional geometry.

Also disclosed herein, in certain embodiments, are printer heads comprising: a plurality of cartridges, each cartridge comprising contents selected from: bio-ink, support material, and a combination thereof; a calibration means for determining the position of a deposition orifice associated with each cartridge; and for each cartridge: a means for receiving and holding the cartridge that aligns the cartridge with a drive pathway; a drive means that dispenses the contents of the cartridge, the drive means operating independently from other drive means; and an actuation means that vertically positions the cartridge relative to a receiving surface to produce a particular three-dimensional geometry in the dispensed contents of the cartridge, the actuation means operating independently from other actuation means; provided that the printer head is for a bioprinter.

Also disclosed herein, in certain embodiments, are bioprinters comprising: a printer head comprising: a cartridge carrier for receiving and holding a plurality of cartridges, each cartridge comprising contents selected from: bio-ink, support material, and a combination thereof; and for each cartridge: a means for receiving and holding the cartridge that aligns the cartridge with a drive pathway; a drive means that dispenses the contents of the cartridge, the drive means operating independently from other drive means; an actuation means that vertically positions the cartridge relative to a receiving surface to produce a particular three-dimensional geometry in the dispensed contents of the cartridge, the actuation means operating independently from other actuation means; a receiving surface for receiving dispensed contents of a cartridge; and a calibration means for determining the position of: 1) a deposition orifice associated with each cartridge, and 2) a print target surface supported by the receiving surface.

CERTAIN DEFINITIONS

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

As used in this specification and the appended claims, the singular forms "a," "an," and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth. Any reference to "or" herein is intended to encompass "and/or" unless otherwise stated.

As used herein, "allograft" means an organ or tissue derived from a genetically non-identical member of the same species as the recipient.

As used herein, "bio-ink" means a liquid, semi-solid, or solid composition comprising a plurality of cells. Bio-ink has high cell density, or native-like cell density. In some embodiments, bio-ink consists essentially of cells. In some embodiments, bio-ink comprises cell solutions, cell aggregates, cell-comprising gels, multicellular bodies, or tissues. In some embodiments, the bio-ink additionally comprises support material. In some embodiments, the bio-ink additionally comprises non-cellular materials that provide specific biomechanical properties that enable bioprinting.

As used herein, "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated, computer-aided, three-dimensional prototyping device (e.g., a bioprinter).

As used herein, "cartridge" means any object that is capable of receiving (and holding) a bio-ink or a support material.

As used herein, a "computer module" means a software component (including a section of code) that interacts with a larger computer system. In some embodiments, a software module (or program module) comes in the form of a file and typically handles a specific task within a larger software system. In some embodiments, a module is included in one or more software systems. In other embodiments, a module is seamlessly integrated with one or more other modules into one or more software systems. A computer module is optionally a stand-alone section of code or, optionally, code that is not separately identifiable. A key feature of a computer module is that it allows an end user to use a computer to perform the identified functions.

As used herein, "implantable" means biocompatible and capable of being inserted or grafted into or affixed onto a living organism either temporarily or substantially permanently.

As used herein, "organ" means a collection of tissues joined into structural unit to serve a common function.

Examples of organs include, but are not limited to, skin, sweat glands, sebaceous glands, mammary glands, bone, brain, hypothalamus, pituitary gland, pineal body, heart, blood vessels, larynx, trachea, bronchus, lung, lymphatic vessel, salivary glands, mucous glands, esophagus, stomach, gallbladder, liver, pancreas, small intestine, large intestine, colon, urethra, kidney, adrenal gland, conduit, ureter, bladder, fallopian tube, uterus, ovaries, testes, prostate, thyroid, parathyroid, meibomian gland, parotid gland, tonsil, adenoid, thymus, and spleen.

As used herein, "patient" means any individual. The term is interchangeable with "subject," "recipient," and "donor." None of the terms should be construed as requiring the supervision (constant or otherwise) of a medical professional (e.g., physician, nurse, nurse practitioner, physician's assistant, orderly, hospice worker, social worker, clinical research associate, etc.) or a scientific researcher.

As used herein, "stem cell" means a cell that exhibits potency and self-renewal. Stem cells include, but are not limited to, totipotent cells, pluripotent cells, multipotent cells, oligopotent cells, unipotent cells, and progenitor cells. Stem cells are optionally embryonic stem cells, peri-natal stem cells, adult stem cells, amniotic stem cells, and induced pluripotent stem cells.

As used herein, "tissue" means an aggregate of cells. Examples of tissues include, but are not limited to, connective tissue (e.g., areolar connective tissue, dense connective tissue, elastic tissue, reticular connective tissue, and adipose tissue), muscle tissue (e.g., skeletal muscle, smooth muscle and cardiac muscle), genitourinary tissue, gastrointestinal tissue, pulmonary tissue, bone tissue, nervous tissue, and epithelial tissue (e.g., simple epithelium and stratified epithelium), endoderm-derived tissue, mesoderm-derived tissue, and ectoderm-derived tissue.

As used herein, "xenograft" means an organ or tissue derived from a different species as the recipient.

Current Methods of Organ Transplants

Currently, there is no reliable method for de novo organ synthesis. Organs are only derived from living donors (e.g., for kidney and liver donations), deceased donors (e.g., for lung and heart donations) and, in a few cases, animals (e.g., porcine heart valves). Thus, patients needing an organ transplant must wait for a donor organ to become available. This results in a shortage of available organs. Additionally, reliance on organs harvested from a living organism increases the chance of transplant rejection.

Transplant Rejections

In certain instances, a patient receiving an organ transplant experience hyperacute rejection. As used herein, "hyperacute rejection" means a complement-mediated immune response resulting from the recipient's having pre-existing antibodies to the donor organ. Hyperacute rejection occurs within minutes and is characterized by blood agglutination. If the transplanted organ is not immediately removed, the patient may become septic. Xenografts will produce hyperacute rejection unless the recipient is first administered immunosuppressants. In some embodiments, a tissue or organ fabricated de novo will not comprise any antigens and thus cannot be recognized by any antibodies of the recipient.

In certain instances, a patient receiving an organ transplant experiences acute rejection. As used herein, "acute rejection" means an immune response that begins about one week after transplantation to about one year after transplantation. Acute rejection results from the presence of foreign HLA molecules on the donor organ. In certain instances, APCs recognize the foreign HLAs and activate helper T cells. In certain instances, helper T cells activate cytotoxic T cells and macrophages. In certain instances, the presence of cytotoxic T cells and macrophages results in the death of cells with the foreign HLAs and thus damage (or death) of the transplanted organ. Acute rejection occurs in about 60-75% of kidney transplants, and 50-60% of liver transplants. In some embodiments, a tissue or organ fabricated de novo will not comprise any HLAs and thus will not result in the activation of helper T cells.

In certain instances, a patient receiving an organ transplant experiences chronic rejection. As used herein, "chronic rejection" means transplant rejection resulting from chronic inflammatory and immune responses against the transplanted tissue. In some embodiments, a tissue or organ fabricated de novo will not comprise any antigens or foreign HLAs and thus will not induce inflammatory or immune responses.

In certain instances, a patient receiving an organ transplant experiences chronic allograft vasculopathy (CAV). As used herein, "chronic allograft vasculopathy" means loss of function in transplanted organs resulting from fibrosis of the internal blood vessels of the transplanted organ. In certain instances, CAV is the result of long-term immune responses to a transplanted organ. In some embodiments, a tissue or organ fabricated de novo will not comprise any antigens or foreign HLAs and thus will not result in an immune response.

In order to avoid transplant rejection, organ recipients are administered immunosuppressant drugs. Immunosuppressants include, but are not limited to, corticosteroids (e.g., prednisone and hydrocortisone), calcineurin inhibitors (e.g., cyclosporine and tacrolimus), anti-proliferative agents (e.g., azathioprine and mycophenolic acid), antibodies against specific components of the immune system (e.g., basiliximab, dacluzimab, anti-thymocyte globulin (ATG) and anti-lymphocyte globulin (ALG) and mTOR inhibitors (e.g., sirolimus and everolimus)). However, immunosuppressants have several negative side-effects including, but not limited to, susceptibility to infection (e.g., infection by *pneumocystis carinii* pneumonia (PCP), cytomegalovirus pneumonia (CMV), herpes simplex virus, and herpes zoster virus) and the spread of malignant cells, hypertension, dyslipidaemia, hyperglycemia, peptic ulcers, liver and kidney injury, and interactions with other medicines. In some embodiments, a tissue or organ fabricated de novo will not result in an immune response and thus will not require the administration of an immunosuppressant.

Infections

In certain instances, a donor organ may be infected with an infectious agent. Following the transplant of the infected organ, the infectious agent is able to spread throughout the donor (due in part to the use of immunosuppressant drugs). By way of non-limiting example, recipients have contracted HIV, West Nile Virus, rabies, hepatitis C, lymphocytic choriomeningitis virus (LCMV), tuberculosis, Chagas disease, and Creutzfeldt-Jakob disease from transplanted organs. While such infections are rare, they can nevertheless occur—social histories for deceased donors are often inaccurate as they are necessarily derived from next-of-kin, serological tests may produce false-negative results if seroconversion has not occurred, or serological tests may also produce false-negatives due to hemodilution following blood transfusion. Further, many uncommon infectious agents are not screened for due to the limited time a harvested organ is viable. In some embodiments, a tissue or organ fabricated de novo will not comprise any infectious agents.

Donor Complications

A living donor may also experience complications as a result of donating an organ. These complications include nosocomial infections, allergic reactions to the anesthesia, and surgical errors. Further, an organ donor may one day find themselves in need of the organ they donated. For example, the remaining kidney of a kidney donor or the remaining lobe of a liver donor may become damaged. In some embodiments, a tissue or organ fabricated de novo obviates the need for donor organs and thus will avoid negative side-effects to the donor.

In light of the shortage of available organs and all the complications that can follow a donor organ transplant, there is a need for a method of de novo fabrication of tissues and organs.

Tissue Engineering

Tissue engineering is an interdisciplinary field that applies and combines the principles of engineering and life sciences toward the development of biological substitutes that restore, maintain, or improve tissue function through augmentation, repair, or replacement of an organ or tissue. The basic approach to classical tissue engineering is to seed living cells into a biocompatible and eventually biodegradable environment (e.g., a scaffold), and then culture this construct in a bioreactor so that the initial cell population can expand further and mature to generate the target tissue upon implantation. With an appropriate scaffold that mimics the biological extracellular matrix (ECM), the developing tissue may adopt both the form and function of the desired organ after in vitro and in vivo maturation. However, achieving high enough cell density with a native tissue-like architecture is challenging due to the limited ability to control the distribution and spatial arrangement of the cells throughout the scaffold. These limitations may result in tissues or organs with poor mechanical properties and/or insufficient function. Additional challenges exist with regard to biodegradation of the scaffold, entrapment of residual polymer, and industrial scale-up of manufacturing processes. Scaffoldless approaches have been attempted. Current scaffoldless approaches are subject to several limitations:

Complex geometries, such as multi-layered structures wherein each layer comprises a different cell type, may require definitive, high-resolution placement of cell types within a specific architecture to reproducibly achieve a native tissue-like outcome.

Scale and geometry are limited by diffusion and/or the requirement for functional vascular networks for nutrient supply.

The viability of the tissues may be compromised by confinement material that limits diffusion and restricts the cells' access to nutrients.

Disclosed herein, in certain embodiments, are devices, systems, and methods that generate a three-dimensional tissue construct. The devices, systems, and methods disclosed herein utilize a three-phase process: (i) pre-processing, or bio-ink preparation, (ii) processing, i.e. the actual automated delivery/printing of the bio-ink particles into the bio-paper by the bioprinter, and (iii) post-processing, i.e., the maturation/incubation of the printed construct in the bioreactor. Final structure formation takes place during post-processing via the fusion of the bio-ink particles. The devices, systems, and methods disclosed herein have the following advantages:

They are capable of producing cell-comprising tissues and/or organs.

They mimic the environmental conditions of the natural tissue-forming processes by exploiting principles of developmental biology.

They can achieve a broad array of complex topologies (e.g., multilayered structures, repeating geometrical patterns, segments, sheets, tubes, sacs, etc.).

They are compatible with automated means of manufacturing and are scalable.

Bioprinting enables improved methods of generating cell-comprising implantable tissues that are useful in tissue repair, tissue augmentation, tissue replacement, and organ replacement. Additionally, bioprinting enables improved methods of generating micro-scale tissue analogs including those useful for in vitro assays.

Bioprinting

Disclosed herein, in certain embodiments, are devices, systems, and methods for fabricating tissues and organs. In some embodiments, the devices are bioprinters. In some embodiments, the methods comprise the use of bioprinting techniques. In further embodiments, the tissues and organs fabricated by use of the devices, systems, and methods described herein are bioprinted.

In some embodiments, bioprinted cellular constructs, tissues, and organs are made with a method that utilizes a rapid prototyping technology based on three-dimensional, automated, computer-aided deposition of cells, including cell solutions, cell suspensions, cell-comprising gels or pastes, cell concentrations, multicellular bodies (e.g., cylinders, spheroids, ribbons, etc.), and support material onto a biocompatible surface (e.g., composed of hydrogel and/or a porous membrane) by a three-dimensional delivery device (e.g., a bioprinter). As used herein, in some embodiments, the term "engineered," when used to refer to tissues and/or organs means that cells, cell solutions, cell suspensions, cell-comprising gels or pastes, cell concentrates, multicellular aggregates, and layers thereof are positioned to form three-dimensional structures by a computer-aided device (e.g., a bioprinter) according to computer code. In further embodiments, the computer script is, for example, one or more computer programs, computer applications, or computer modules. In still further embodiments, three-dimensional tissue structures form through the post-printing fusion of cells or multicellular bodies similar to self-assembly phenomena in early morphogenesis.

While a number of methods are available to arrange cells, multicellular aggregates, and/or layers thereof on a biocompatible surface to produce a three-dimensional structure including manual placement, positioning by an automated, computer-aided machine such as a bioprinter is advantageous. Advantages of delivery of cells or multicellular bodies with this technology include rapid, accurate, and reproducible placement of cells or multicellular bodies to produce constructs exhibiting planned or pre-determined orientations or patterns of cells, multicellular aggregates and/or layers thereof with various compositions. Advantages also include assured high cell density, while minimizing cell damage.

In some embodiments, methods of bioprinting are continuous and/or substantially continuous. A non-limiting example of a continuous bioprinting method is to dispense bio-ink from a bioprinter via a dispense tip (e.g., a syringe, capillary tube, etc.) connected to a reservoir of bio-ink. In further non-limiting embodiments, a continuous bioprinting method is to dispense bio-ink in a repeating pattern of functional units. In various embodiments, a repeating functional unit has any suitable geometry, including, for example, circles, squares, rectangles, triangles, polygons, and irregular geometries. In further embodiments, a repeating pattern of bioprinted function units comprises a layer and a plurality of layers are bioprinted adjacently (e.g., stacked) to form an engineered tissue or organ. In various embodiments, 2, 3, 4, 5, 6, 7, 8, 9, 10, 11, 12, 13, 14, 15, or more layers are bioprinted adjacently (e.g., stacked) to form an engineered tissue or organ.

In some embodiments, a bioprinted functional unit repeats in a tessellated pattern. A "tessellated pattern" is a plane of figures that fills the plane with no overlaps and no gaps. An advantage of continuous and/or tessellated bioprinting can include an increased production of bioprinted tissue. Increased production can include achieving increased scale, increased complexity, or reduced time or cost of production. Another non-limiting potential advantage can be reducing the number of calibration events that are required to complete the bioprinting of a three-dimensional construct. Continuous bioprinting also facilitates printing larger tissues from a large reservoir of bio-ink, optionally using a syringe mechanism.

Methods in continuous bioprinting optionally involve optimizing and/or balancing parameters such as print height, pump speed, robot speed, or combinations thereof independently or relative to each other. In one example, the bioprinter head speed for deposition was 3 mm/s, with a dispense height of 0.5 mm for the first layer and dispense height was increased 0.4 mm for each subsequent layer. In some embodiments, the dispense height is approximately equal to the diameter of the bioprinter dispense tip. Without limitation a suitable and/or optimal dispense distance does not result in material flattening or adhering to the dispensing needle. In various embodiments, the bioprinter dispense tip has an inner diameter of about, 20, 50, 100, 150, 200, 250, 300, 350, 400, 450, 500, 550, 600, 650, 700, 750, 800, 850, 900, 950, 1000 µm, or more, including increments therein. In various embodiments, the bio-ink reservoir of the bioprinter has a volume of about 0.5, 1, 2, 3, 4, 5, 6, 7, 8, 9, 10, 15, 20, 25, 30, 35, 40, 45, 50, 55, 60, 65, 70, 75, 80, 85, 90, 95, 100 cubic centimeters, or more, including increments therein. The pump speed may be suitable and/or optimal when the residual pressure build-up in the system is low. Favorable pump speeds may depend on the ratio between the cross-sectional areas of the reservoir and dispense needle with larger ratios requiring lower pump speeds. In some embodiments, a suitable and/or optimal print speed enables the deposition of a uniform line without affecting the mechanical integrity of the material.

In some embodiments, a bioprinted functional unit is a multiaxial tube comprising a core layer, a mantle layer, and optionally one or more intermediate layers between the core and mantle layers. In some embodiments, a bioprinted functional unit is a triaxial tube.

Figure 28:
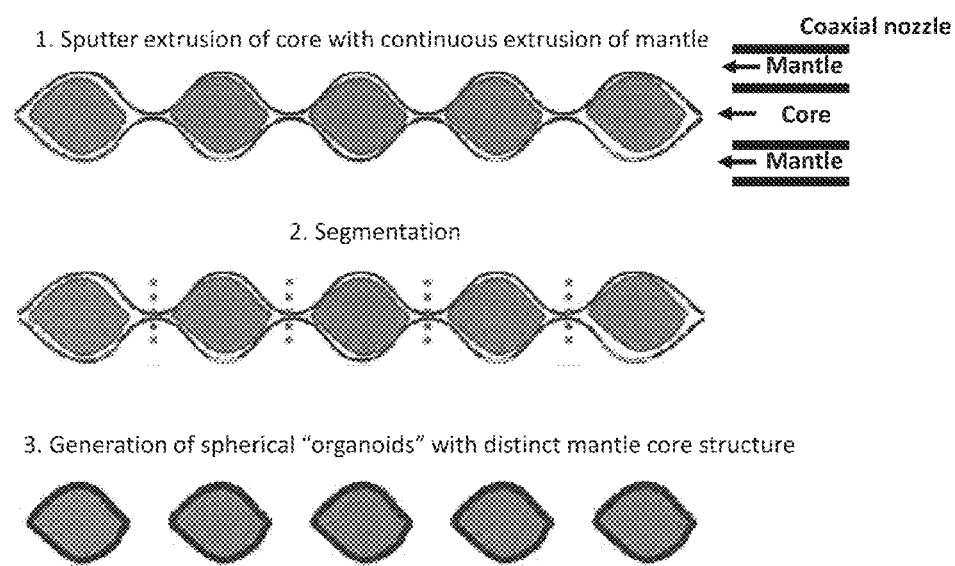
FIG. 28 illustrates a non-limiting example of extrusion through a coaxial nozzle; in this example, sputter-extrusion of a core layer with simultaneous continuous extrusion of a mantle layer leads to a segmented coaxial tube, which is subsequently severed between the segments to form spherical "organoids".

In some embodiments, a bioprinted functional unit is a coaxial tube. In certain embodiments, the coaxial tube comprises a core layer (inner layer) and a mantle layer (outer layer). In certain embodiments, the bio-ink of the core layer differs from the bio-ink of the mantle layer and the resultant coaxial tube is a cylinder with bilayer morphology. In certain embodiments, the bio-ink of the core layer comprises only non-cellular components and can be removed after bioprinting and the resultant coaxial tube is a hollow cylinder. In other embodiments, the core layer is non-continuously bioprinted in a "sputter core feed" pattern while the mantle layer is continuously bioprinted (see FIG. 28). The sputter-extrusion of a core layer with concomitant continuous extrusion of a mantle layer creates a segmented coaxial tube. Subsequent manipulation of the segmented coaxial tube may result in the mantle layer collapsing onto itself along a region where the core layer is absent. Severing each segment at these collapsed regions creates spherical spheres, or organoids, with distinct mantle and core structure.

In some embodiments, methods of bioprinting are non-continuous and/or substantially non-continuous. A non-limiting example of a non-continuous bioprinting method is to dispense bio-ink from a bioprinter via a cartridge configured as part of an ink jet head. In some embodiments, the ink jet head comprises a high precision dispense tip and an ink jet solenoid valve closely coupled to a syringe pump. In some embodiments, dispense volume is controlled by syringe pressure, valve actuation time, or a high precision dispense tip, or any combination thereof. In some embodiments, dispense volume is controlled by syringe pressure, valve actuation time, and a high precision dispense tip. In various embodiments, the ink jet dispense volume is 10, 20, 30, 40, 50, 60, 70, 80, 90, 100, 110, 120, 130, 140, 150, 160, 170, 180, 190, or 200 picoliters per droplet, or more, including increments therein. In some embodiments, bulk dispensing is performed by using an external pressurized reservoir.

The inventions disclosed herein include business methods. In some embodiments, the speed and scalability of the devices and methods disclosed herein are utilized to design, build, and operate industrial and/or commercial facilities for production of engineered tissues and/or organs. In further embodiments, the engineered tissues and/or organs are produced, stored, distributed, marketed, advertised, and sold as, for example, materials, tools, and kits for medical treatment of tissue damage, tissue disease, and/or organ failure or materials, tools, and kits to conduct biological assays and/or drug screening as a service.

Bioprinter

Disclosed herein, in certain embodiments, are bioprinters for fabricating tissues and organs. In some embodiments, a bioprinter is any instrument that automates a bioprinting process. In certain embodiments, a bioprinter disclosed herein comprises: a printer head comprising a cartridge carrier for receiving and holding a plurality of cartridges, each cartridge comprising contents selected from: bio-ink, support material, and a combination thereof and for each cartridge: a means for receiving and holding the cartridge that aligns the cartridge with a drive pathway; a drive means that dispenses the contents of the cartridge, the drive means operating independently from other drive means; and an actuation means that vertically positions the cartridge relative to a receiving surface to produce a particular three-dimensional geometry in the dispensed contents of the cartridge, the actuation means operating independently from other actuation means; a receiving surface for receiving dispensed contents of a cartridge; and a calibration means for determining the position of: 1) a deposition orifice associated with each cartridge, and 2) a print target surface supported by the receiving surface. In certain embodiments, a bioprinter disclosed herein comprises: one or more printer heads (also called print heads), wherein a printer head comprises a means for receiving and holding at least one cartridge, and wherein said cartridge comprises contents selected from one or more of: bio-ink and support material; a means for calibrating the position of at least one cartridge; and a means for dispensing the contents of at least one cartridge. In certain embodiments, a bioprinter disclosed herein comprises: one or more printer heads, wherein each printer head comprises a cartridge carrier for receiving and holding a plurality of cartridges, the cartridge carrier rotatable to align a selected cartridge with a drive pathway, each cartridge comprising contents selected from one or more of: bio-ink and support material; a drive means for dispensing the contents of the selected cartridge; an actuation means for positioning the one or more printer heads relative to the receiving surface to produce a particular three-dimensional geometry in the dispensed contents of the selected cartridge; and a calibration means for determining the position of: 1) a deposition orifice associated with the selected cartridge, and 2) a print target surface supported by the receiving surface. In certain embodiments, a bioprinter disclosed herein comprises a printer head, the printer head comprising a means for receiving and holding a cartridge, the cartridge comprising contents selected from one or more of:

bio-ink and support material; a drive means for dispensing the contents of the cartridge; a receiving surface for receiving dispensed contents of the cartridge; an actuation means for positioning the printer head relative to the receiving surface; and a die for controlling simultaneous deposition of a plurality of constructs in parallel, each construct having a particular three-dimensional geometry.

In various embodiments, a bioprinter dispenses bio-ink and/or support material in pre-determined geometries (e.g., positions, patterns, etc.) in two or three dimensions. In some embodiments, a bioprinter achieves a particular geometry by moving a printer head relative to a printer stage or receiving surface adapted to receive bioprinted materials. In other embodiments, a bioprinter achieves a particular geometry by moving a printer stage or receiving surface relative to a printer head. In further embodiments, a bioprinter achieves a particular three-dimensional geometry by moving the receiving surface relative to one or more printer heads. In some embodiments, a bioprinter achieves a particular geometry by moving a printer head relative to a printer stage or receiving surface adapted to receive bioprinted materials and by moving the printer stage or receiving stage relative to the printer head. In certain embodiments, the bioprinter is maintained in a sterile environment.

In some embodiments, a bioprinter disclosed herein comprises one or more printer heads. In further embodiments, a printer head comprises a means for receiving and holding at least one cartridge. In some embodiments, a printer head comprises a deposition orifice for each cartridge. In some embodiments, the cartridge is connected to a remote reservoir of contents. In some embodiments, the cartridge is a disposable, single-use cartridge. In some embodiments, a printer head comprises a means for receiving and holding more than one cartridge. In some embodiments, the means for receiving and holding at least one cartridge is selected from: magnetic attraction, a collet chuck grip, a ferrule, a nut, a barrel adapter, or a combination thereof. In some embodiments, the means for receiving and holding at least one cartridge is a collet chuck grip. In some embodiments, a printer head comprises an independent actuation means for z-axis positioning of the printer head relative to a receiving surface. In some embodiments, a printer head further comprises an independent means to adjust and/or maintain the temperature of the printer head, the cartridge, and/or the deposition orifice. In further embodiments, a printer head comprises a heat exchanger jacket around the cartridge to allow coolant flow, wherein an external device regulates the temperature and flow of coolant to the printer head. In other embodiments, a printer head comprises a heat exchanger jacket around the cartridge to allow heated liquid flow, wherein an external device regulates the temperature and flow of the heated liquid to the printer head.

In some embodiments, a bioprinter disclosed herein comprises one or more printer heads, wherein each printer head comprises a cartridge carrier for receiving and holding a plurality of cartridges. In further embodiments, the cartridge carrier receives and holds any suitable number of cartridges. In various embodiments, the cartridge carrier suitably receives and holds about 2, 3, 4, 5, 6, 7, 8, 9, 10, 11, 12, 13, 14, 15, 16, 17, 18, 19, 20 or more cartridges. In some embodiments, the cartridge carrier receives and holds about 2 to about 10 cartridges. In further embodiments, each printer head comprises a deposition orifice for each cartridge. In other embodiments, each printer head comprises a common deposition orifice for the plurality of cartridges. In some embodiments, the plurality of cartridges comprises a wash cartridge to decontaminate a dispensing path of the bioprinter. In certain embodiments, a bioprinter further comprises a corresponding wash station to provide a place for spent wash medium to be stored. In some embodiments, at least one of the cartridges is connected to a remote reservoir of contents. In some embodiments, at least one of the cartridges is a disposable, single-use cartridge. In some embodiments, a printer head comprises an independent actuation means for z-axis positioning of the printer head relative to a receiving surface. In some embodiments, a printer head further comprises an independent means to adjust and/or maintain the temperature of the printer head, the cartridge, and/or the deposition orifice.

Figure 13:
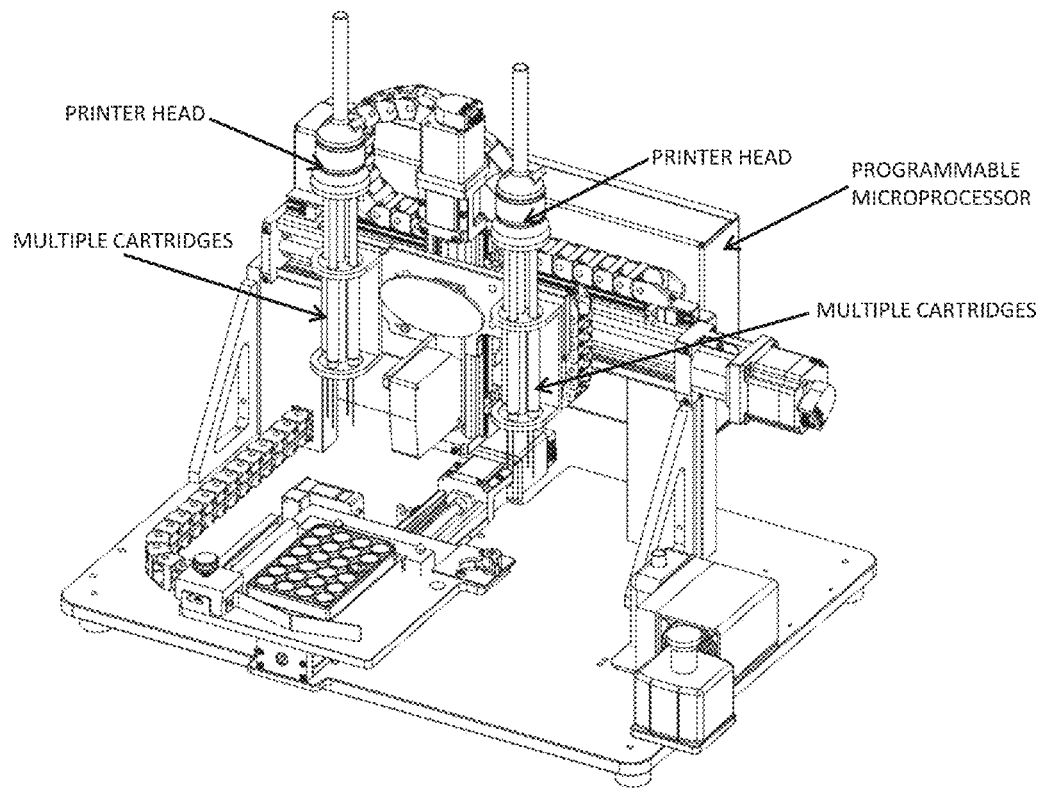
FIG. 13 illustrates a non-limiting example of a bioprinter with two printer heads including multiple print cartridges, each cartridge containing a distinct material for deposition; in this case, each printer head utilizes a separate deposition tip for each cartridge.

Referring to FIG. 13, in a particular embodiment, the bioprinter has two printer heads, each of which comprises a deposition orifice for each of the attached cartridges.

Figure 14:
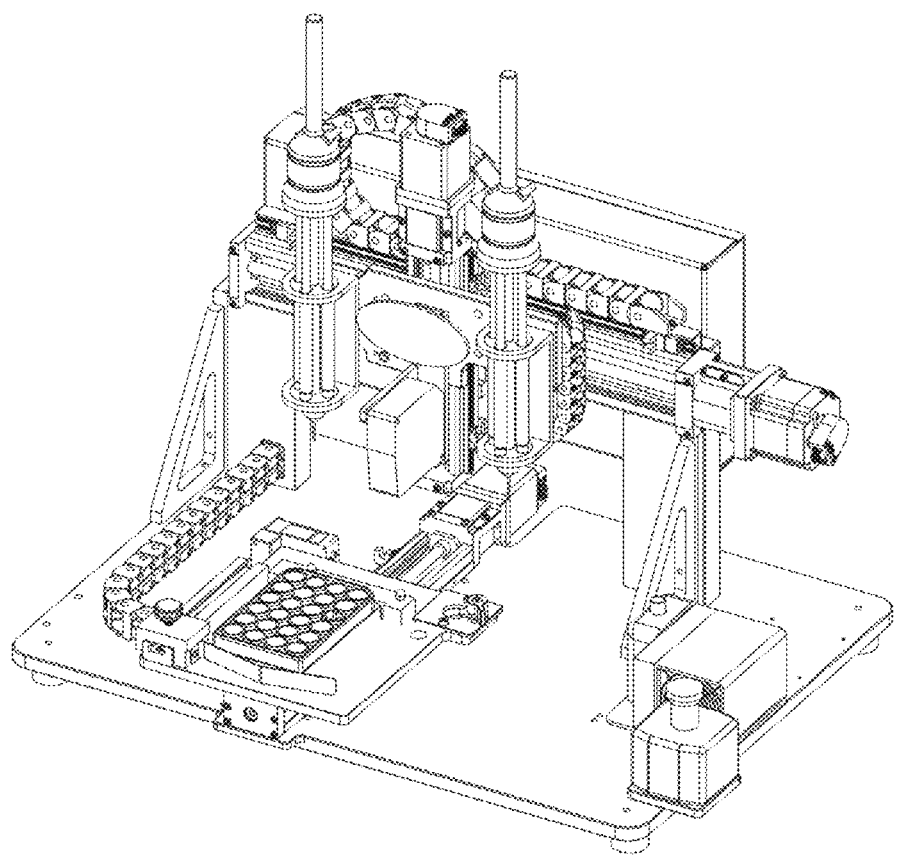
FIG. 14 illustrates a non-limiting example of a bioprinter with two printer heads including multiple print cartridges, each cartridge containing a distinct material for deposition; in this case, each printer head utilizes a common deposition tip for the multiple cartridges.

Referring to FIG. 14, in a particular embodiment, the bioprinter has two printer heads, comprises a common deposition orifice for the attached plurality of cartridges.

Figure 15:
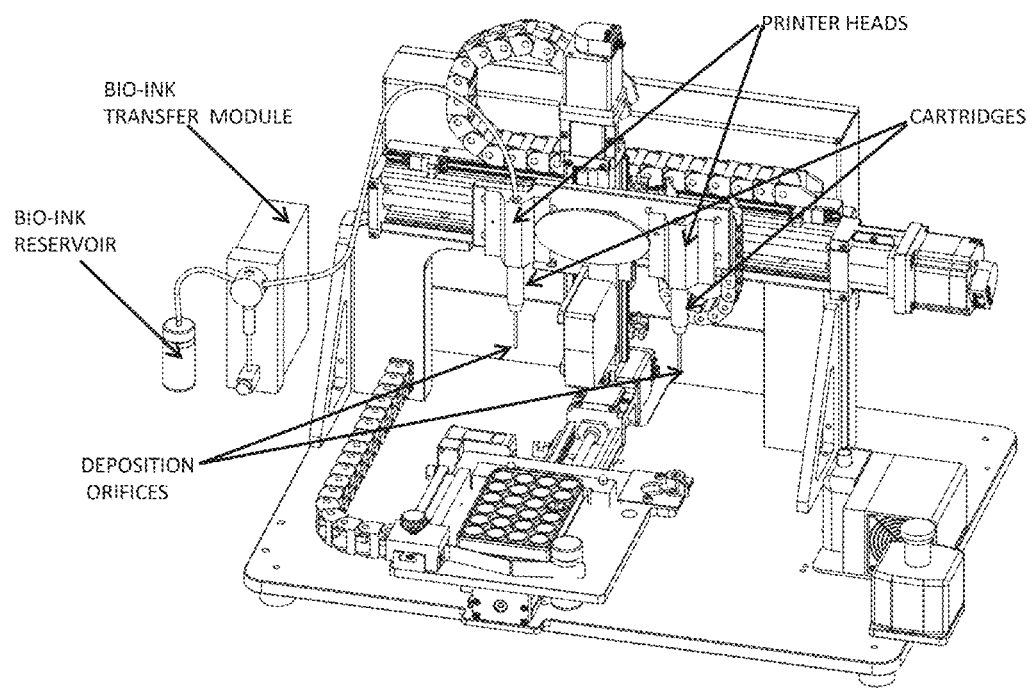
FIG. 15 illustrates a non-limiting example of a bioprinter with two printer heads, one of which is connected to a remote reservoir in the form of a single container; in this case, the printer head utilizes a single deposition tip.

Referring to FIG. 15, in a particular embodiment, the bioprinter has two printer heads, and a remote reservoir of material is connected to one of the two printer heads. Use of a reservoir is optionally controlled by electronic, pneumatic, or mechanical signaling.

Figure 18:
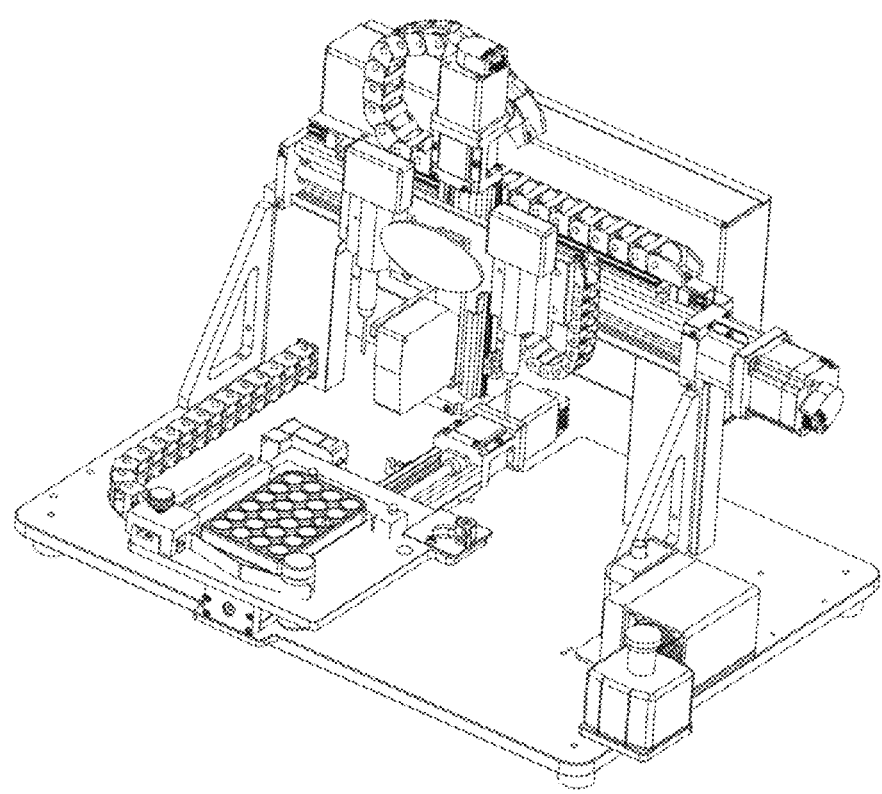
FIG. 18 illustrates a non-limiting example of a bioprinter with two printer heads; in this case, each print head receives bio-ink from a reservoir.

Referring to FIG. 18, in a particular embodiment, the bioprinter has two printer heads, each of which is connected to an internal reservoir system.

Figure 26:
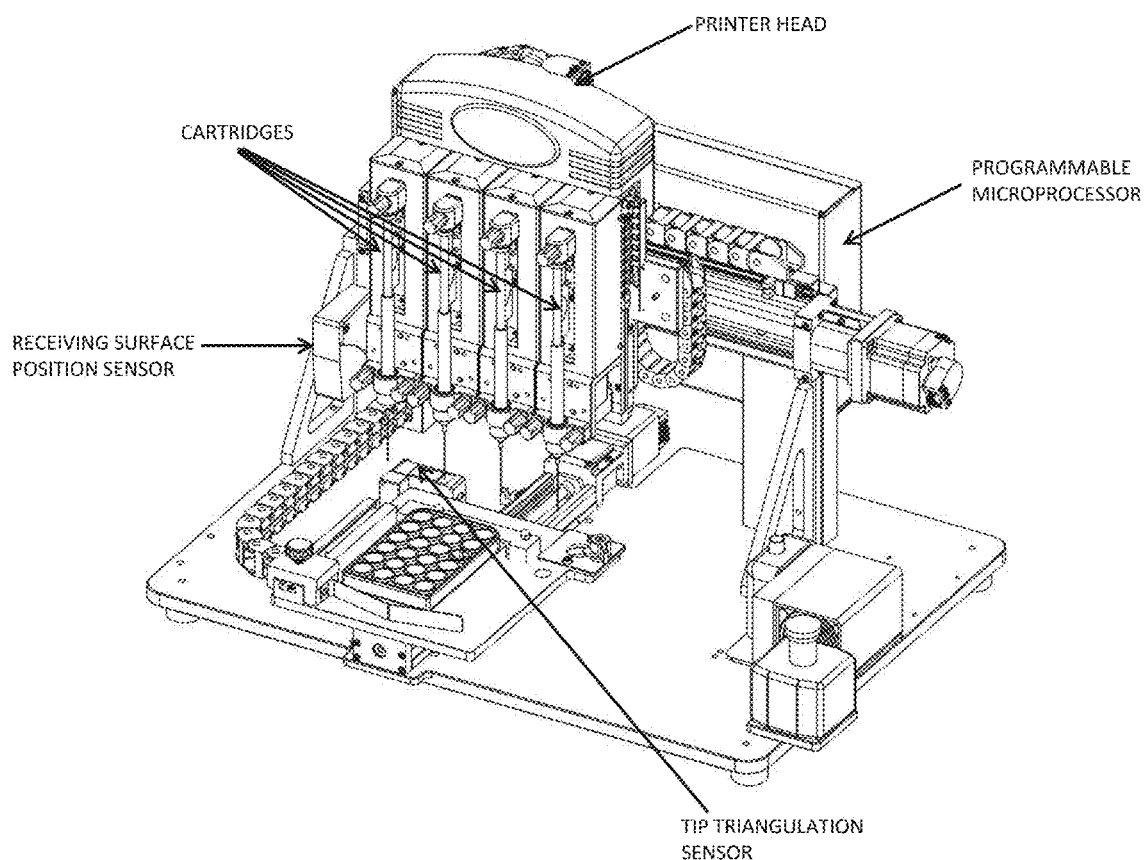
FIG. 26 illustrates a non-limiting example of a bioprinter with the printer head of FIG. 22.

Referring to FIG. 26, in a particular embodiment, the bioprinter has one printer head with four cartridges. Each cartridge has independent z-axis motion with respect to the other cartridges. Each cartridge is also associated with its own deposition orifice. In certain further embodiments, only one cartridge at a time is lowered to interact with the printer stage or receiving surface adapted to receive bioprinted materials. In other further embodiments, one or more cartridges are lowered to interact with the printer stage or receiving surface adapted to receive bioprinted materials.

In some embodiments, a bioprinter disclosed herein comprises a means for calibrating the position of at least one cartridge. In some embodiments, the means for calibrating the position of at least one cartridge of is selected from: laser alignment, optical alignment, mechanical alignment, piezoelectric alignment, magnetic alignment, electrical field or capacitance alignment, ultrasound alignment, image-based alignment, or a combination thereof. In some embodiments, the means for calibrating the position of at least one cartridge is laser alignment. In some embodiments, the means for calibrating the position of at least one cartridge is image-based alignment. In some embodiments, the means for calibrating the position of at least one cartridge is a combination of laser alignment and image-based alignment.

In some embodiments, a bioprinter disclosed herein comprises a calibration means for determining the position of: 1) a deposition orifice associated with the selected cartridge, and 2) a print target surface supported by the receiving surface. In further embodiments, the calibration means calculates a print height, the print height comprising the distance between a deposition orifice and the print target surface. In still further embodiments, the calibration means monitors the print height during deposition of materials. In some embodiments, the calibration means utilizes one or more sensors selected from: triangulation sensors, ultrasonic distance sensing probes, and digital cameras. In some embodiments, the calibration means is a three-dimensional calibration system for an automated bioprinter. In various embodiments, the three-dimensional calibration system comprises a sensor fixed to a receiving surface of the bioprinter for determining the position of a deposition orifice of the bioprinter; and a sensor fixed to a printer head of the bioprinter for determining the position of a print target surface associated with the receiving surface;

whereby the system calculates a print height, the print height comprising the distance between the deposition orifice and a print target surface. In some embodiments, the sensors are selected from: triangulation sensors, ultrasonic distance sensing probes, and digital cameras.

In some embodiments, a bioprinter disclosed herein comprises a means for dispensing the contents of at least one cartridge. In some embodiments, the means for dispensing the contents of at least one cartridge is application of a piston, application of pressure, application of compressed gas, application of hydraulics, or application of a combination thereof. In some embodiments, the means for dispensing the contents of at least one cartridge is application of a piston. In some embodiments, the diameter of the piston is less than the diameter of a cartridge.

In some embodiments, a bioprinter disclosed herein comprises a drive means for dispensing the contents of a selected cartridge. In some embodiments, the drive means for dispensing the contents of a selected cartridge utilizes positive displacement, pneumatic displacement, hydraulic displacement, acoustic resonance, or a combination thereof. In some embodiments, a printer head has its own independent drive means for dispensing the contents of a selected cartridge.

Figures 23A, 23B:
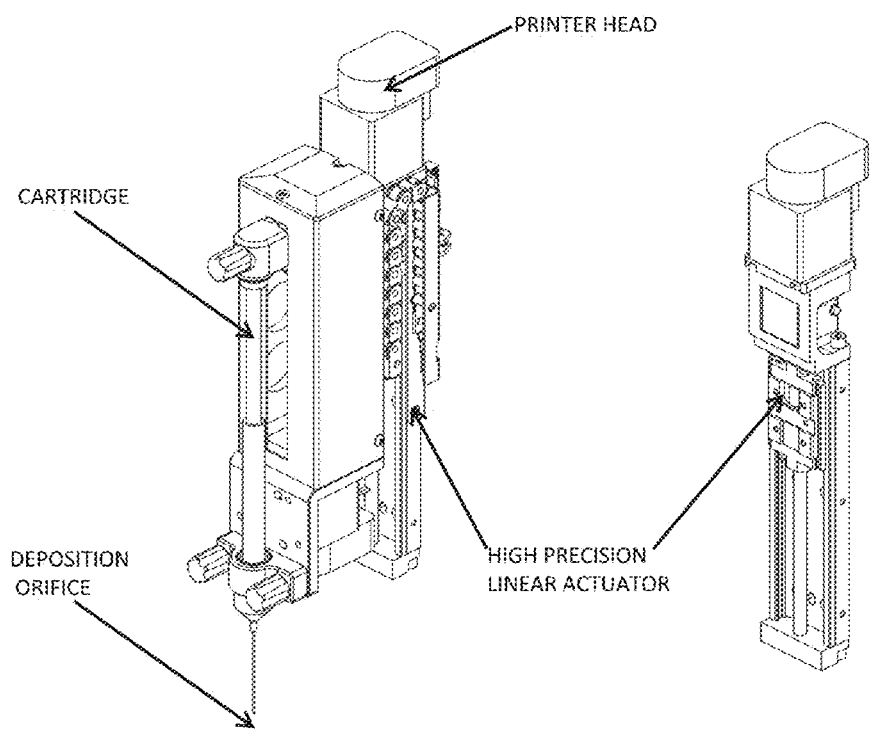
Figure 24A:
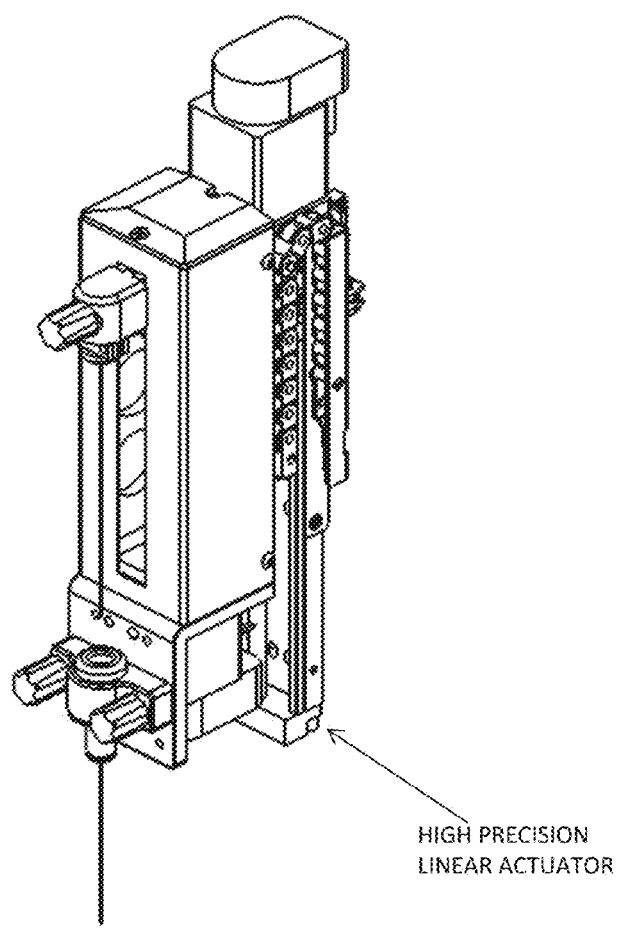
FIG. 24a illustrates the non-limiting example of FIGS. 23a and 23b, without a cartridge and dispense tip.
Figure 24B:
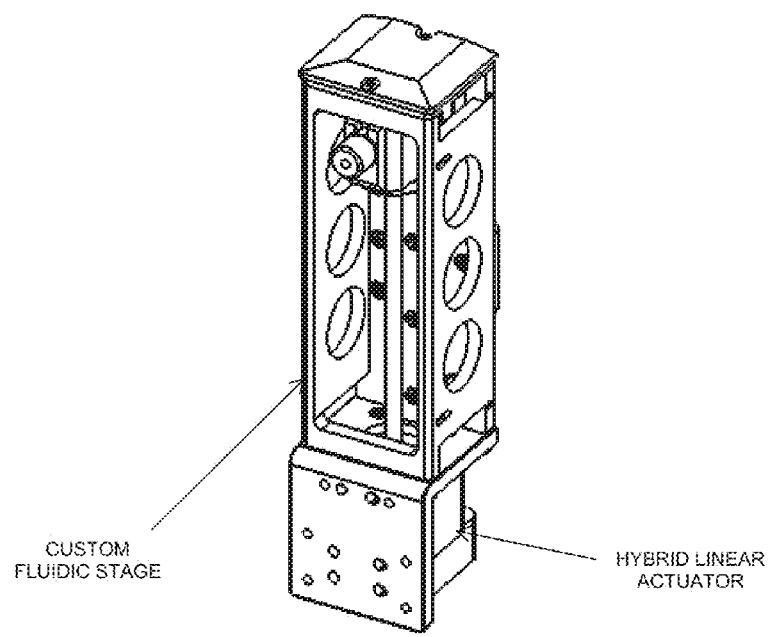
FIG. 24b illustrates the non-limiting example of FIGS. 23a and 23b; in this case, an internal view of the custom fluidic stage and the high precision linear stage are shown.

Referring to FIGS. 23a, 24a, and 24b, in a particular embodiment, the drive means for dispensing the contents of a cartridge is a drive mechanism that comprises dual linear guide rails, a stepper motor and an integral lead screw and motor shaft. In this particular embodiment, the drive mechanism is attached to a z-axis positioning mechanism to adjust the location of the attached cartridge relative to the target printing surface.

In some embodiments, a bioprinter disclosed herein further comprises a receiving surface. In further embodiments, a receiving surface is a non-cytotoxic surface onto which a bioprinter dispenses bio-ink and/or support material. In some embodiments, a bioprinter disclosed herein further comprises a printer stage. In further embodiments, a receiving surface is a surface of a printer stage. In other embodiments, a receiving surface is component separate from a printer stage, but is affixed to or supported by a stage. In some embodiments the receiving surface is flat or substantially flat. In some embodiments the surface is smooth or substantially smooth. In other embodiments, the surface is both substantially flat and substantially smooth. In still further embodiments the receiving surface is designed specifically to accommodate the shape, size, texture, or geometry of the bioprinted structure. In still further embodiments, the receiving surface controls or influences the size, shape, texture, or geometry of a bioprinted construct. In some embodiments, the receiving surface is moved relative to the one or more printer heads to produce a particular three-dimensional geometry in the dispensed contents of a cartridge or a plurality of cartridges. In some embodiments, the receiving surface is a standard assay plate. In some embodiments, the receiving surface is a transwell insert fitted into a 24-well transwell carrier.

In some embodiments, a bioprinter disclosed herein comprises an actuation means for positioning the printer head relative to the receiving surface. In other embodiments, a bioprinter disclosed herein comprises an actuation means for positioning the one or more printer heads relative to the receiving surface to produce a particular three-dimensional geometry in the dispensed contents of the selected cartridge. In some embodiments, the actuation means comprises a ball or lead screw. In some embodiments, the actuation means comprises an optical encoder. In some embodiments, the actuation means comprises a brake mechanism to prevent the printer head from inadvertent contact with the receiving surface. In other embodiments, the actuation means does not comprise a brake mechanism to prevent the printer head from inadvertent contact with the receiving surface. In some embodiments, a printer head has its own independent actuation means for z-axis positioning to adjust the location of the cartridge relative to the target printing surface. In some embodiments, a bioprinter disclosed herein further comprises a second x-axis and/or y-axis positioning mechanism.

Figure 25:
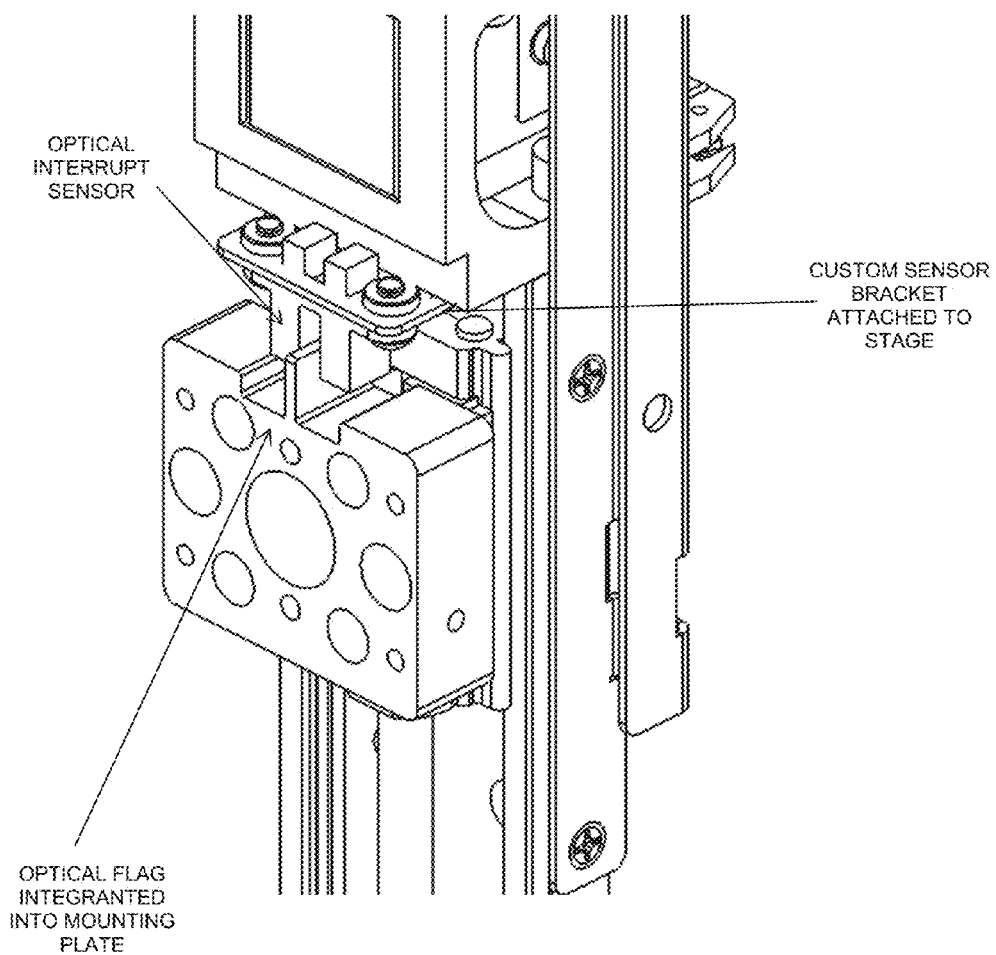
FIG. 25 illustrates a non-limiting example of the z-axis positioning mechanism of FIG. 23b; in this case, the mounting plate is shown along with the optical interrupt sensor and custom sensor bracket.

Referring to FIGS. 23a, 23b, and 25, in a particular embodiment, a printer head has its own independent actuation means for z-axis positioning to adjust the location of the cartridge relative to the target printing surface.

Figure 22:
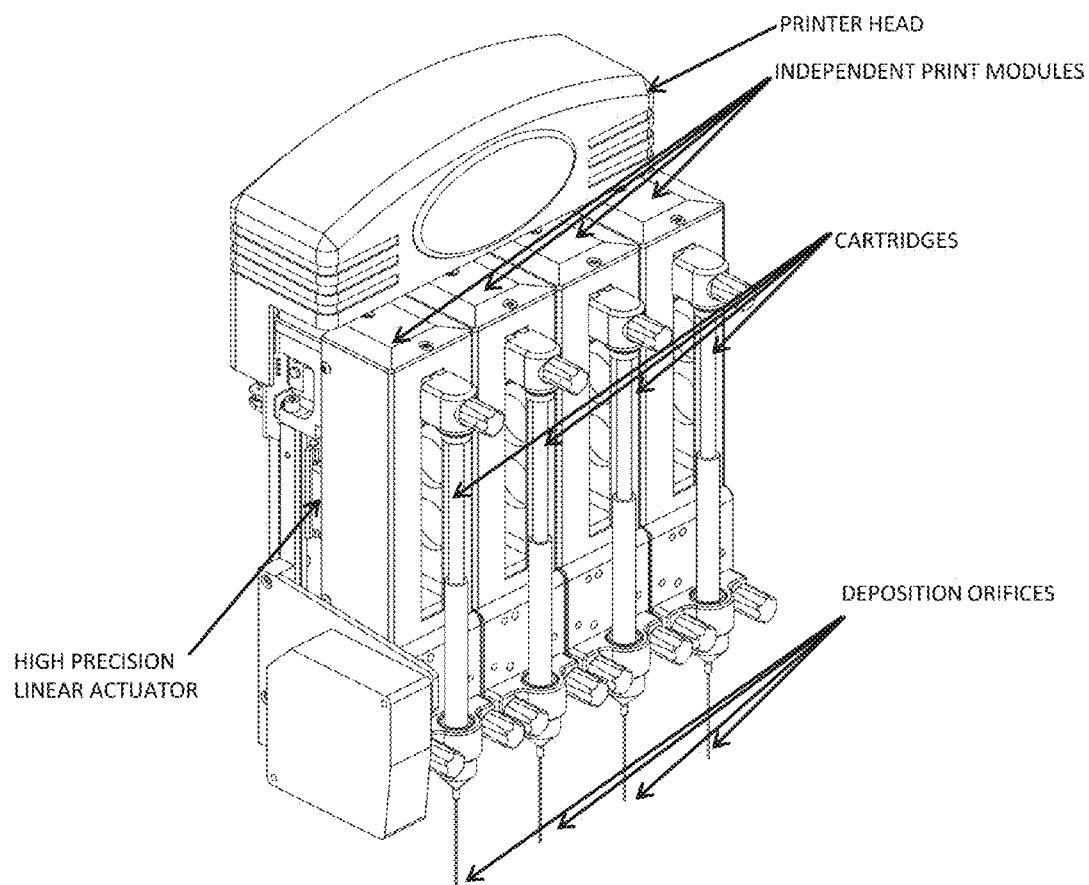
FIG. 22 illustrates a non-limiting exemplary printer head; in this case, a printer head with four cartridges, wherein each cartridge includes its own deposition tip and has independent z-axis (e.g., vertical) motion relative to the other cartridges as well as an independent drive mechanism to dispense the contents of the cartridge.

Referring to FIG. 22, in a particular embodiment, a printer head comprises four independent cartridges, each with its own z-axis positioning mechanism for independent z-axis motion relative to the other cartridges.

In some embodiments, a bioprinter disclosed herein comprises a die for controlling simultaneous deposition of a plurality of constructs in parallel and arranged in a pattern, each construct having a particular three-dimensional geometry; deposition of a single construct having a particular three-dimensional geometry; or a combination thereof. In further embodiments, the die is permanently fixed. In other embodiments, the die is reversibly fixed. In some embodiments, the die controls simultaneous deposition of any suitable number of constructs in parallel. In various embodiments, the die suitably controls simultaneous deposition of about 2, 6, 12, 24, 48, 64, 96, 384, 1536, 3456, or 9600 constructs in parallel. In some embodiments, the die controls simultaneous deposition of about 2 to about 384 constructs in parallel. In some embodiments, the die is configured to be complementary to a standard assay plate. In some embodiments, each construct in the plurality of constructs has the same three-dimensional geometry. In other embodiments, the plurality of constructs does not have the same three-dimensional geometry. Non-limiting examples of the geometries are cylinders, hollow cylinders, polygons, sheets, and circles. In some embodiments, the die controls simultaneous deposition of a plurality of materials in parallel. In further embodiments, the die comprises an input port for each material. In some embodiments, the die is connected to a chamber for containing a uniform layer of bio-ink or support material. In some embodiments, each of the constructs in the plurality of constructs is in contact with one another to form a single construct.

In some embodiments, a bioprinter disclosed herein comprises a die comprising one or more molds for stamping or cutting to shape one or more three-dimensional bioprinted tissues into a desired geometry. In some embodiments, a bioprinter disclosed herein comprises a coaxial or triaxial nozzle for extrusion of one or more three-dimensional bioprinted tissues into a desired geometry. Non-limiting examples of the geometries are cylinders, hollow cylinders, polygons, sheets, and spheres. In some embodiments, an outer diameter of the cylinder is 50, 60, 70, 80, 90, 100, 150, 200, 250, 300, 350, 400, 450, or 500 µm, or more, including increments therein. In some embodiments, an outer diameter of the cylinder is 250 µm or 500 µm. In further embodiments, the coaxial nozzle has dual flow capability with at least two independent inputs for at least two different materials and at least two independent outputs for the preparation of a coaxial tube with a core layer and a mantle layer, the core layer and mantle layer having different composition of materials with respect to each other. In still further embodiments, each of the one or more coaxial nozzles further comprises a means to independently regulate the flow of each of the at least two different materials through the at least two independent outputs. In some embodiments, the means to independently regulate the flow of each of the at least two different materials through the at least two independent outputs allows for continuous extrusion or sputter extrusion.

Figure 2:
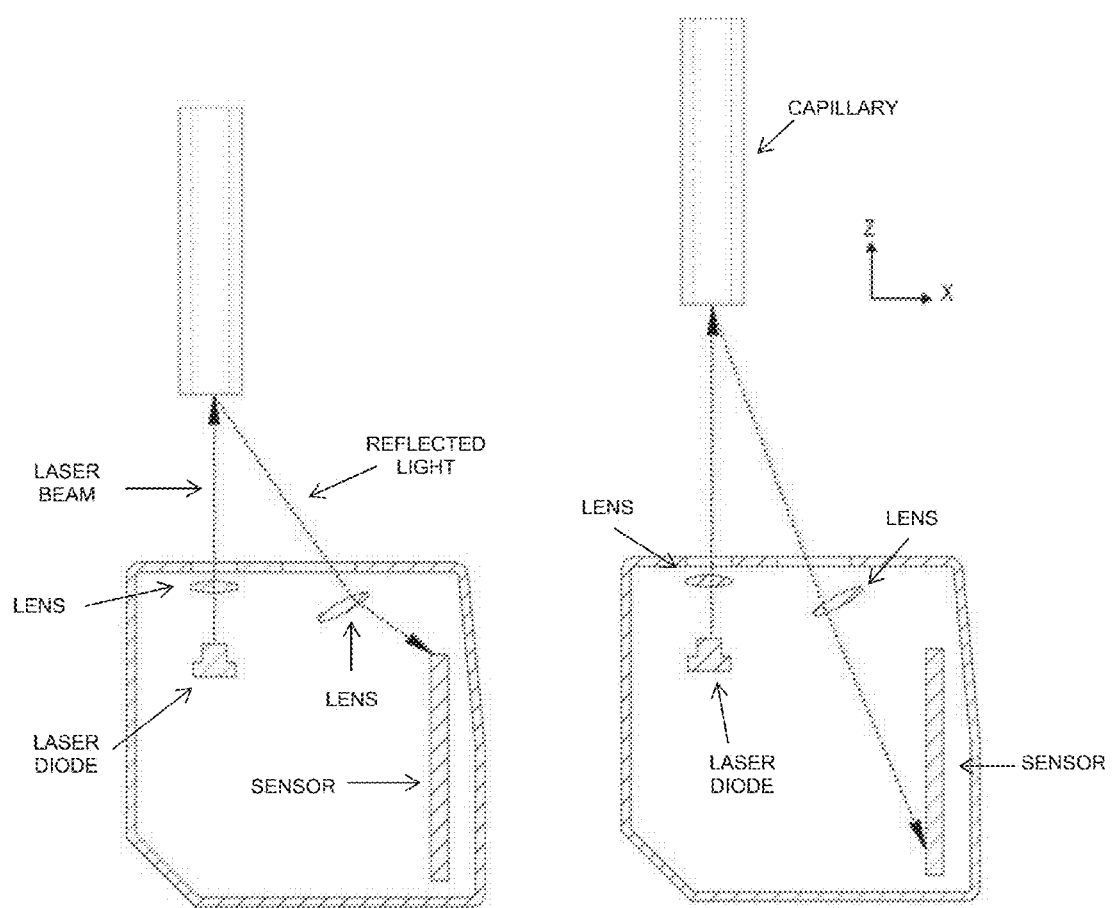
FIG. 2 illustrates a non-limiting example of a laser distance sensor mounted in the vertical position detecting range to capillary.
Figures 1, 8:
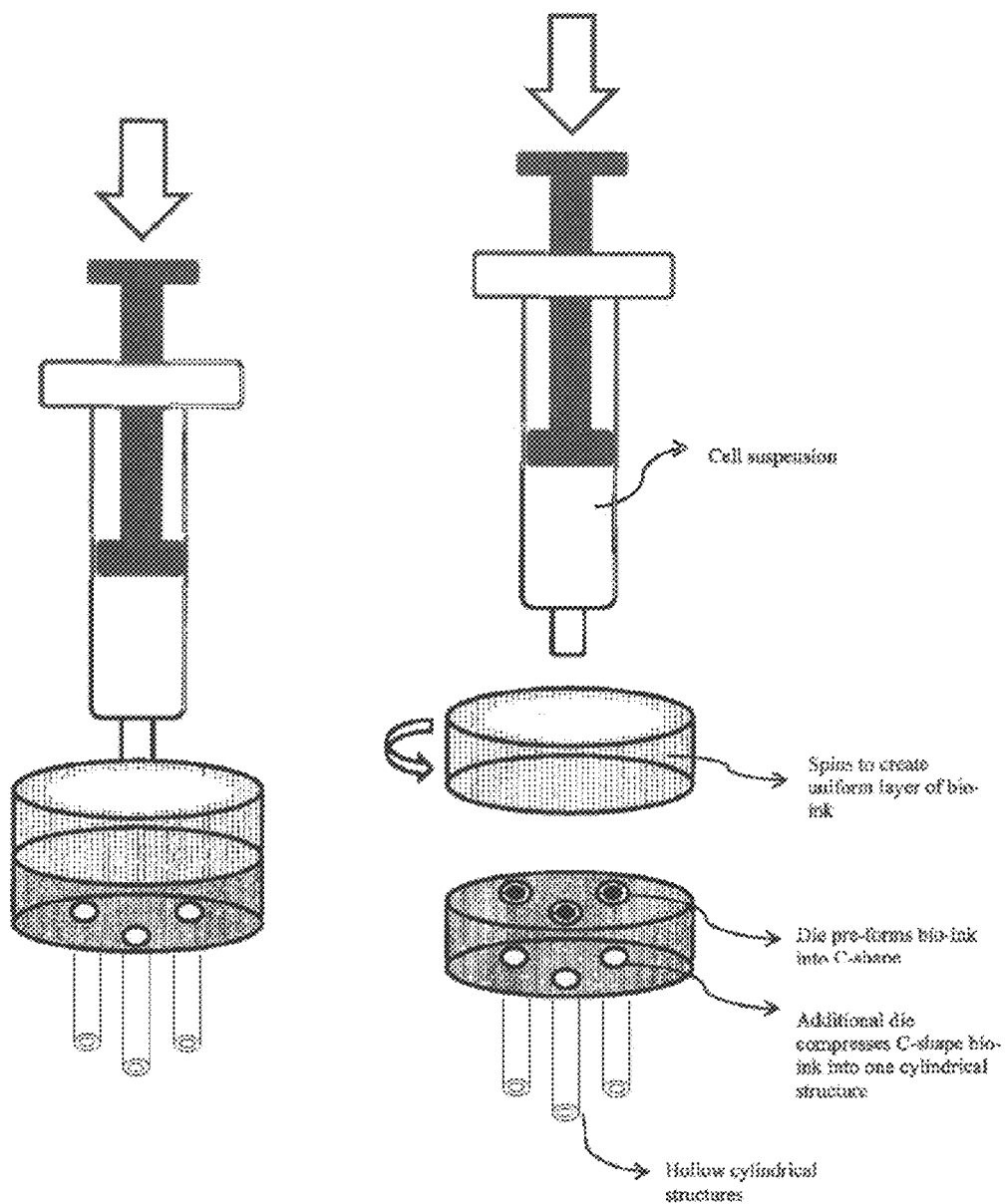
Figures 2, 8:
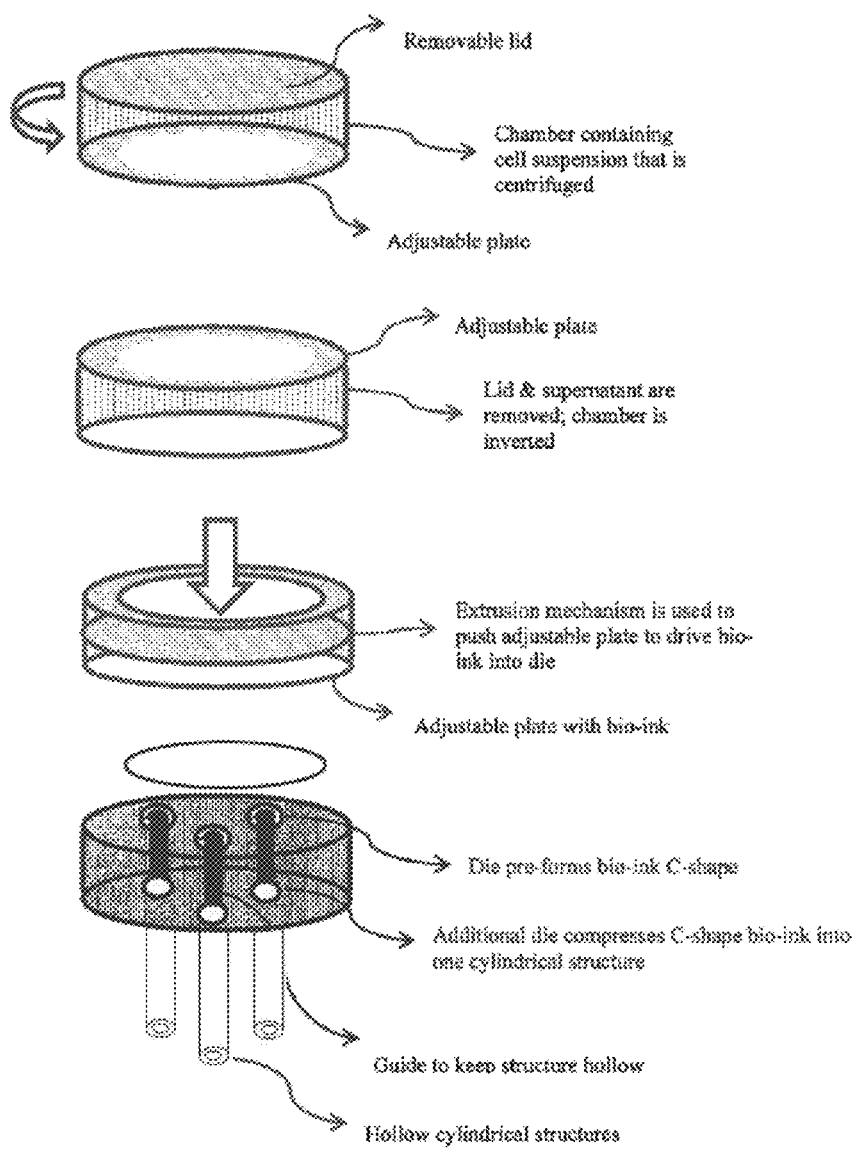

Referring to FIGS. 8-1 and 8-2, in a particular embodiment, a two-part die is connected to a chamber for containing a uniform layer of bio-ink. This chamber comprises a removable lid and an adjustable bottom plate. In order to obtain a uniform layer of bio-ink within the chamber, the chamber is charged with a cell suspension and centrifuged. After the lid and supernatant are removed, the chamber is inverted and attached either permanently or temporarily to an extrusion mechanism. This extrusion mechanism pushes the adjustable bottom plate towards the die, driving the bio-ink into the two-part die. The two-part die comprises a first die with a C-shape mold and a second die that compresses the C-shaped bio-ink to form a contiguous, hollow cylindrical structure as bio-ink exits the second die.

Figure 3:
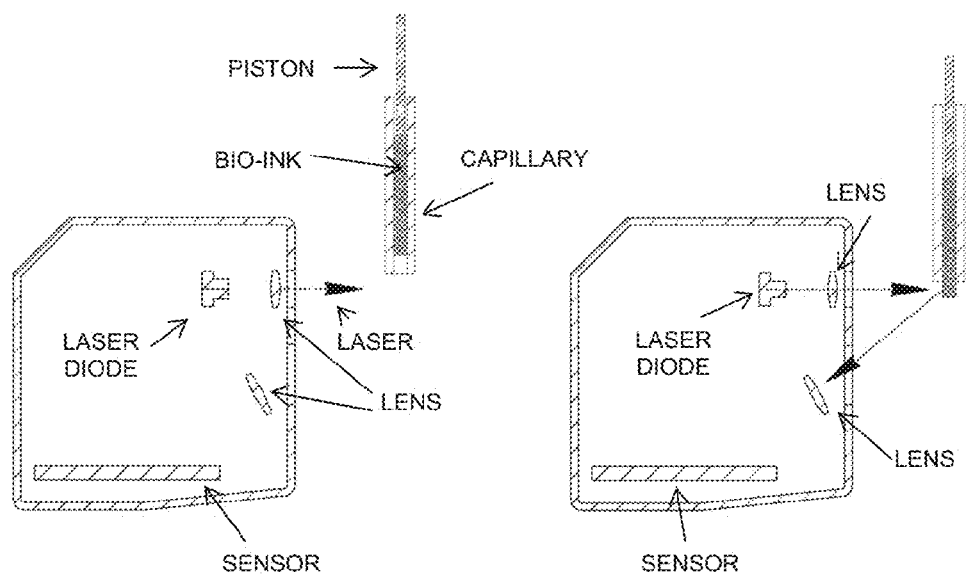
FIG. 3 illustrates a non-limiting example of a laser distance sensor in the horizontal position detecting range to capillary with wire.
Figures 1, 9:
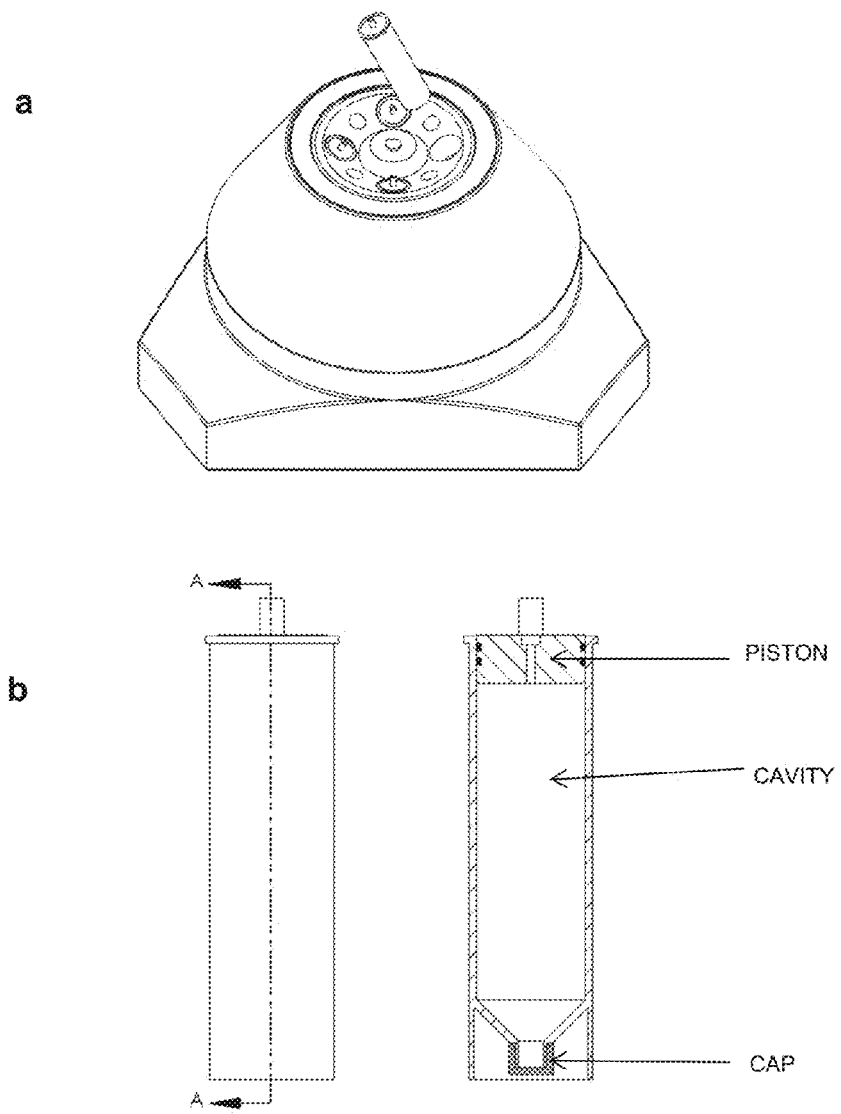
Figures 2, 9:
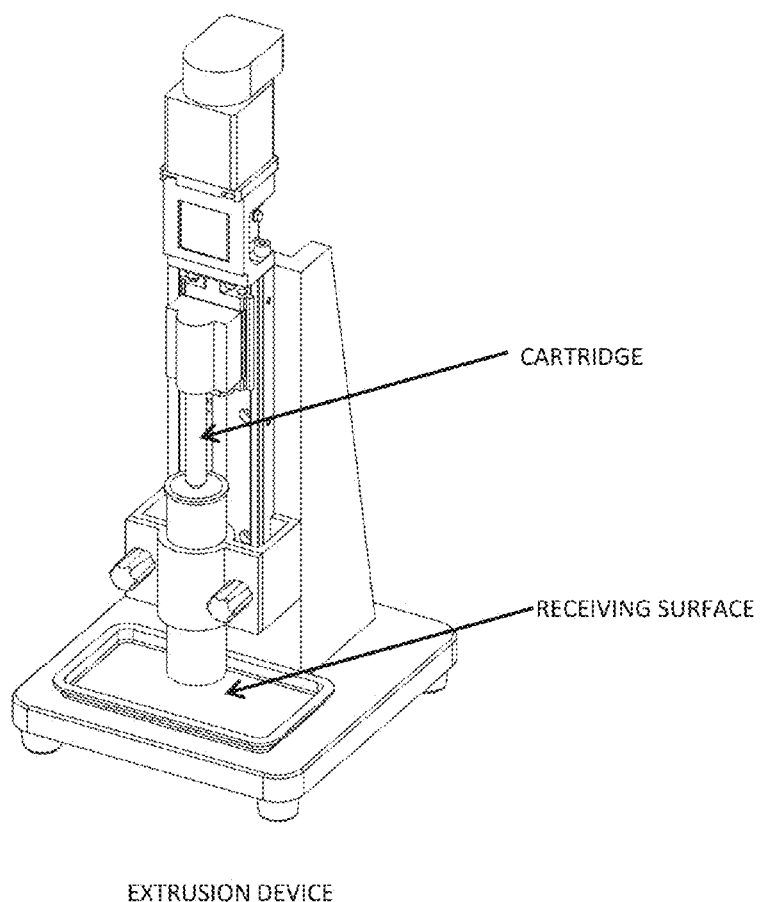
Figures 3, 9:
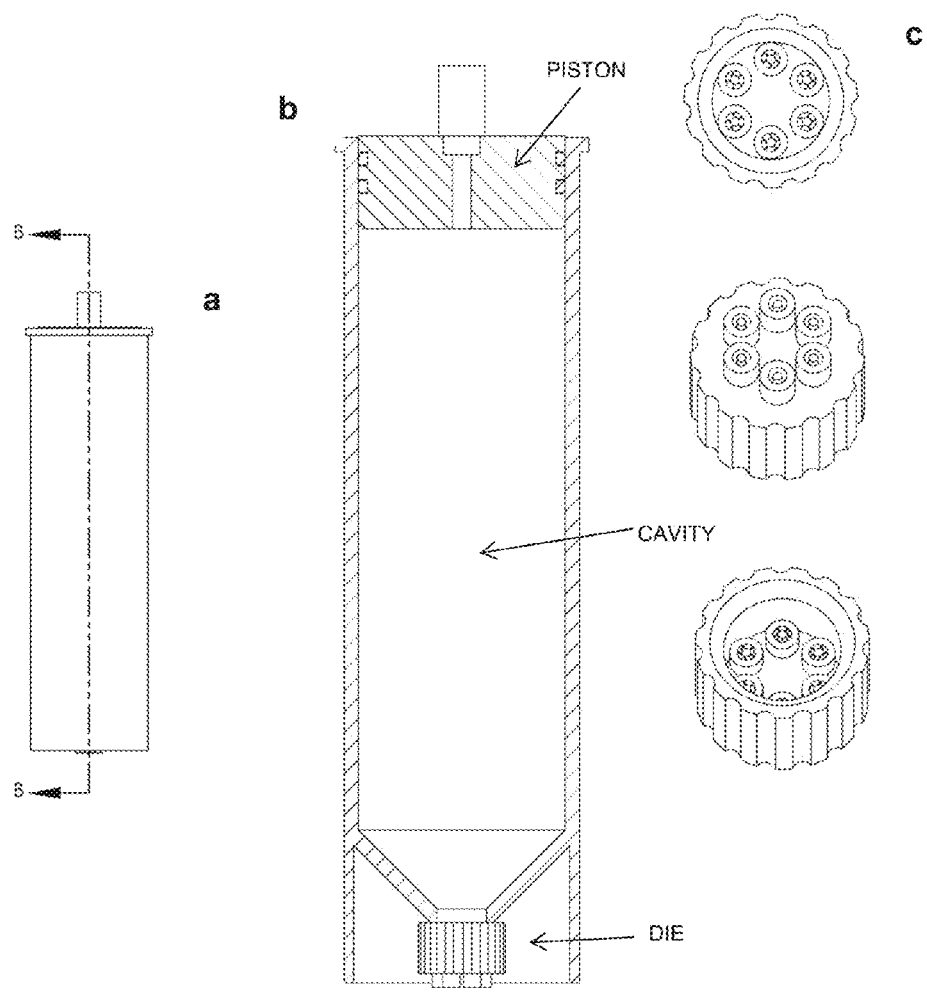

Referring to FIG. 9-3, a die with molds to simultaneously create six hollow tubes is installed onto a cartridge. In other embodiments, the die has molds to extrude one or more tubes in the same or different shapes. In some embodiments, the cartridge is pre-treated prior to installation of the die to increase the cell concentration. A centrifugal apparatus, such as that shown in FIG. 9-1, is used with a cartridge having a removable plug at one end and a self-sealing port at the other end. The self-sealing port provides the entry of bio-ink suspension and later removal of supernatant. The cartridge contains a piston with seals to prevent leakage. Once a die is installed onto a cartridge containing bio-ink, the cartridge may be attached to a bioprinter disclosed herein or to an extrusion device (see FIG. 9-2).

Figure 10:
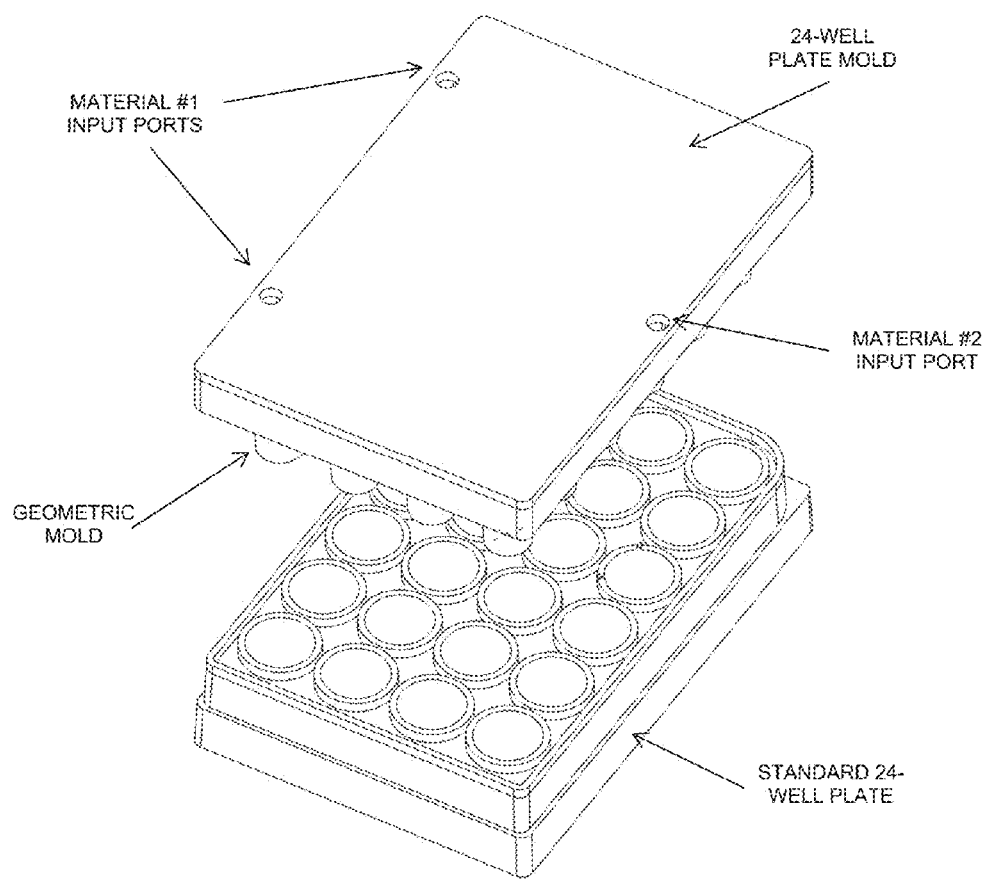
FIG. 10 illustrates a non-limiting schematic example of a two material extrusion plate, or mold lid, which is compatible with a standard 24-well plate.
Figure 11:
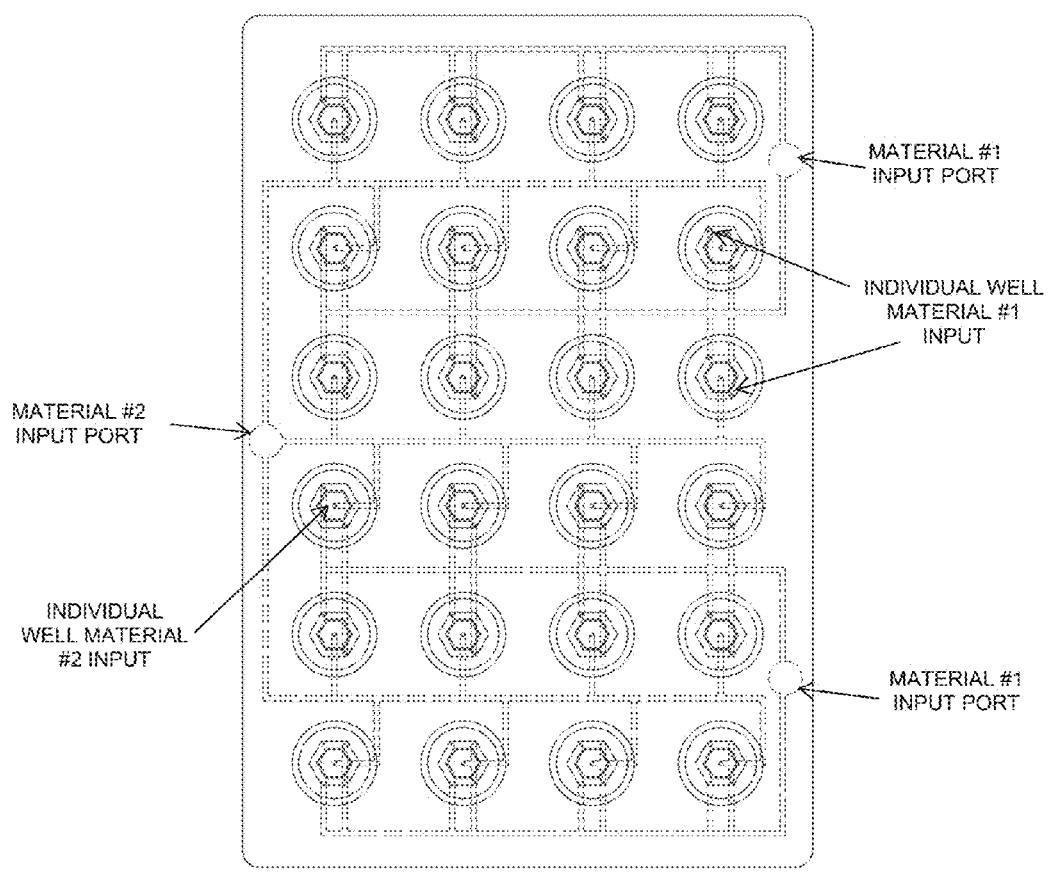
FIG. 11 illustrates a non-limiting schematic example of the extrusion plate of FIG. 10; in this case, a schematic depicting the individual geometric molds, each adapted to deposit materials into a well of the standard 24-well plate, as well as the channels connected to each geometric mold and to the material input ports.
Figure 12:
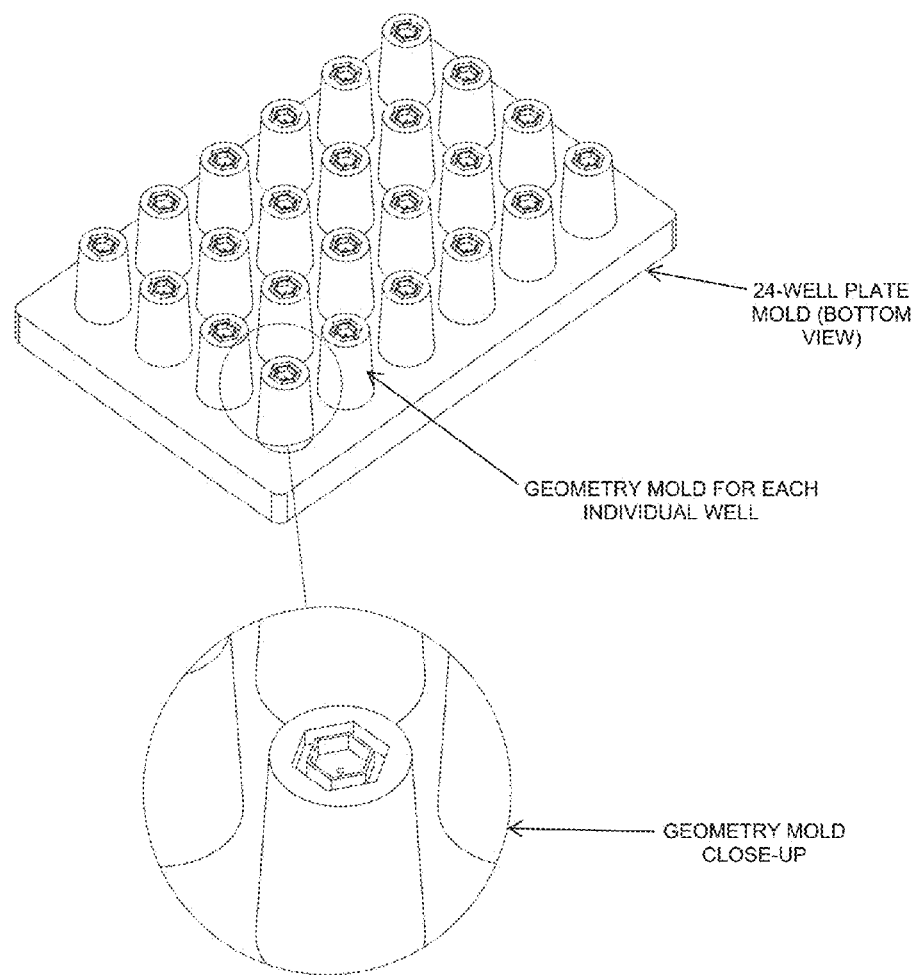
FIG. 12 illustrates a non-limiting schematic example of the mold lid of FIG. 10; in this case, a schematic depicting the individual geometric molds, each adapted to deposit two distinct materials into a specific geometry.

Referring to FIGS. 10, 11, and 12, in a particular embodiment, a die is configured to be an extrusion plate, or mold lid, compatible for a 24-well plate. The die has 24 individual geometric molds and input ports for materials #1 and #2. In general, such geometric molds can produce a single geometry or a mixture of geometries. In this particular embodiment, all 24 individual geometric molds will produce the same geometry for all 24 wells of the receiving surface. Once material is injected through the input ports, the material flows through pre-defined pathways in the form of the geometric molds that control the deposition or extrusion location and geometry of the material into each individual well of the standard 24-well assay plate, which serves as the receiving surface. In this way, material is deposited or extruded into a single well, multiple wells simultaneously or all wells simultaneously. In this particular embodiment, the resultant tissue in an individual well is optionally composed of one or two materials.

In some embodiments, a bioprinter disclosed herein further comprises a means for adjusting temperature. In some embodiments, the means for adjusting temperature adjusts and/or maintains the ambient temperature. In other various embodiments, the means for adjusting temperature adjusts and/or maintains the temperature of, by way of non-limiting example, the print head, cartridge, contents of the cartridge (e.g., bio-ink, support material, etc.), the printer stage, and the receiving surface.

In some embodiments, the means for adjusting temperature is a heating element. In some embodiments, the means for adjusting temperature is a heater. In some embodiments, the means for adjusting temperature is a radiant heater, a convection heater, a conductive heater, a fan heater, a heat exchanger, or a combination thereof. In some embodiments, the means for adjusting temperature is a cooling element. In some embodiments, the means for adjusting temperature is a container of coolant, a chilled liquid, ice, or a combination thereof. In some embodiments, the means for adjusting temperature is a radiant cooler, convection cooler, a conductive cooler, a fan cooler, or a combination thereof.

In various embodiments, the means for adjusting temperature adjusts a temperature to about 0, 5, 10, 15, 20, 25, 30, 35, 40, 45, 50, 55, 60, 65, 70, 75, 80, 85, or 90° C. including increments therein. In some embodiments, temperature is adjusted to between about 40° C. and about 90° C. In some embodiments, temperature is adjusted to between about 37° C. and about 90° C. In other embodiments, temperature is adjusted to between about 0° C. and about 10° C.

In some embodiments, the means for adjusting temperature adjusts the temperature of the deposition tip and/or part or all of the cartridge. In some embodiments, the means for adjusting temperature is located on the printer head. In further embodiments, the means for adjusting temperature is a heat exchanger jacket located around at least part of the cartridge to allow flow of temperature-regulated liquid, wherein an external device regulates the temperature and flow of the temperature-regulated liquid to the printer head. In some embodiments, the temperature range of the temperature-regulated liquid is 4° C. to 40° C. In some embodiments, a cooling or heating device is not located on the printer head and the printer head must be moved to the location of the cooling or heating device within the bioprinter.

Figure 27:
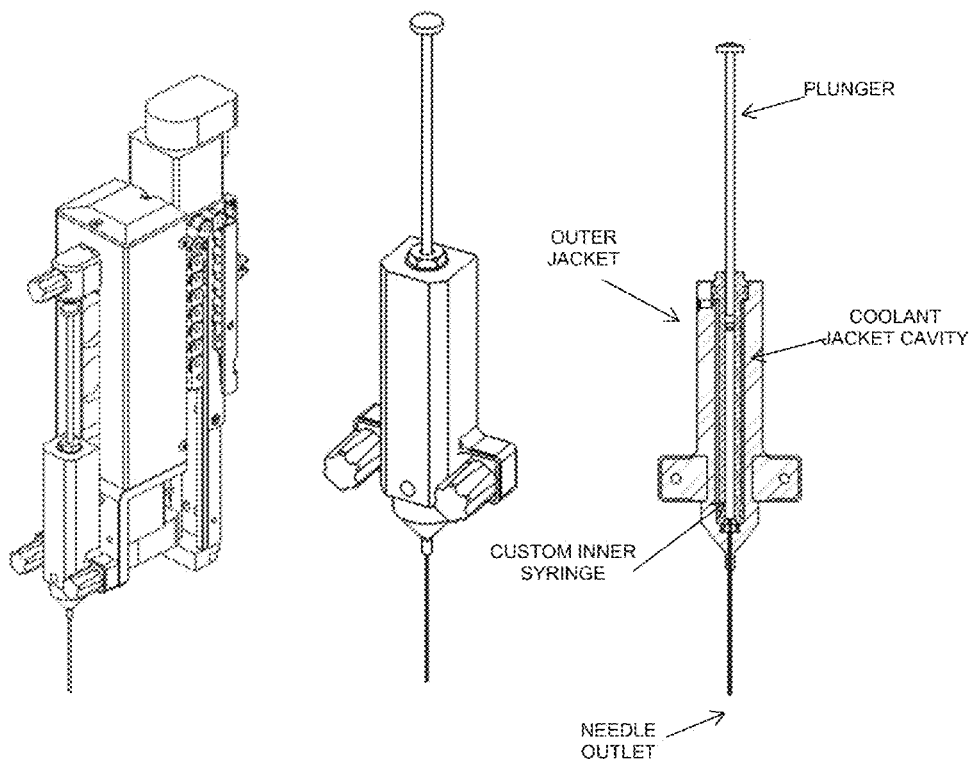
FIG. 27 illustrates a non-limiting example of a printer head comprising a means to control syringe temperature; in this example, (a) a printer head is shown with a heat exchange jacket around a syringe; (b) the heat exchange jacket around the syringe is shown in the absence of the print head; and (c) a schematic view of the heat exchange jacket around the syringe is shown.

Referring to FIG. 27, in a particular embodiment, a printer head comprises a heat exchanger jacket located around a syringe, wherein an external device regulates the temperature and flow of coolant to the printer head. The outer jacket is made of PET. Coolant flows into the jacket at a maximum of 27 psi. The coolant flows out of the jacket at about 1 atm.

In some embodiments, a bioprinter disclosed herein, further comprises a means for applying a wetting agent to one or more of: the printer stage; the receiving surface, the deposition orifice, bio-ink, support material, or the printed construct. In some embodiments, the means for applying the wetting agent is any suitable method of applying a fluid (e.g., a sprayer, a pipette, an inkjet, etc.). In some embodiments, the wetting agent is water, tissue culture media, buffered salt solutions, serum, or a combination thereof. In further embodiments, a wetting agent is applied after the bio-ink or supporting material is dispensed by the bioprinter. In some embodiments, a wetting agent is applied simultaneously or substantially simultaneously with the bio-ink or supporting material being dispensed by the bioprinter. In some embodiments, a wetting agent is applied prior to the bio-ink or supporting material being dispensed by the bioprinter.

Printer Head

Disclosed herein, in certain embodiments, are bioprinters for fabricating tissues and organs. In some embodiments, a bioprinter disclosed herein comprises one or more printer heads (also called print heads). In further embodiments, a printer head comprises a means for receiving and holding at least one cartridge. In still further embodiments, a printer head attaches at least one cartridge to a bioprinter.

Many means for receiving and holding at least one cartridge are suitable. Suitable means for receiving and holding at least one cartridge include those that reliably, precisely, and securely attach at least one cartridge to a bioprinter. In various embodiments, the means for receiving and holding at least one cartridge is, by way of non-limiting example, magnetic attraction, a collet chuck grip, a ferrule, a nut, a barrel adapter, or a combination thereof.

In some embodiments, a printer head disclosed herein receives and holds one cartridge. In various other embodiments, a printer head disclosed herein receives and holds 2, 3, 4, 5, 6, 7, 8, 9, 10, or more cartridges simultaneously. In further embodiments, a printer head disclosed herein further comprises a means to select a cartridge to be employed in bioprinting from among a plurality of cartridges received and held.

In some embodiments, a printer head disclosed herein further comprises (or is in fluid communication with) a reservoir to contain bio-ink and/or support materials beyond the capacity of the one or more cartridges. In further embodiments, a reservoir supplies bio-ink and/or support materials to one or more cartridges for dispensing via a dispensing orifice. Printer head configurations including a reservoir are particularly useful in continuous or substantially continuous bioprinting applications. Many volumes are suitable for a reservoir disclosed herein. In various embodiments, a reservoir has an internal volume of, for example, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500 ml or more, including increments therein.

In some embodiments, bioprinting involves using a computer to configure parameters such as cell type, print height, pump speed, robot speed, deposition order, deposition location, or combinations thereof independently or relative to each other. In further embodiments, computer code specifies the positioning of a printer head to configure printer head height above a receiving surface. In further embodiments, computer code specifies the direction and speed of the motion of a printer head to configure dispensing characteristics for bio-ink and/or support material.

In some embodiments, a printer head disclosed herein is connected to an independent z-axis positioning mechanism. In some embodiments, a printer head disclosed herein is connected to an independent means to adjust and/or maintain the temperature of the printer head, the attached cartridge, and/or the deposition orifice. In some embodiments, a printer head disclosed herein is connected to an independent z-axis positioning mechanism and an independent means to adjust and/or maintain the temperature of the printer head, the attached cartridge, and/or the deposition orifice.

Referring to FIG. 22, in particular embodiments, a printer head comprises four independent print cartridges, each with its own deposition tip and attached to an independent drive mechanism to dispense the contents of the cartridge. Each cartridge also has independent z-axis motion relative to the other three cartridges via its own z-axis positioning mechanism. Although shown in FIG. 22 with each cartridge associated with a syringe needle, each cartridge independently has a deposition tip selected from syringe needle, capillary tube, or inkjet tip. In certain embodiments, only one cartridge at a time is lowered to interact with the printer stage or receiving surface adapted to receive bioprinted materials. In other further embodiments, one or more cartridges are lowered to interact with the printer stage or receiving surface adapted to receive bioprinted materials. Optionally, each cartridge has an independent means to adjust and/or maintain the temperature of the cartridge, the deposition orifice, and/or the contents. In certain embodiments, one or more cartridges are able to reach a gel heater and cooler located on the bioprinter. In further embodiments, only two cartridges, either the two right-most or the two left-most, are able to reach a gel heater and cooler located on the bioprinter.

Referring to FIG. 26, in a particular embodiment, a bioprinter comprises the printer head as described in FIG. 22. This bioprinter allows for the use of one or two multi-well plates or Petri dishes as the receiving surface. This bioprinter also comprises a calibration means to determine the position of each deposition orifice and each print target surface supported by the receiving surface. Optionally, the bioprinter may further comprise a second x-axis and/or y-axis positioning mechanism to enhance the capabilities of the bioprinter.

Referring to FIGS. 23a, 23b, 24a, 24b, and 25, in a particular embodiment, a printer head has a custom fluidic stage and a high precision linear stage. The printer head has independent z-axis motion relative to other components within the bioprinter through the use of an attached z-axis positioning mechanism to rapidly adjust the location of the attached cartridge relative to the target printing surface with high precision and resolution. The positioning mechanism comprises a lead screw and an optical encoder. In addition, the printer head is attached to a drive mechanism to dispense the contents of the attached cartridge. In this particular embodiment, the printer head is connected to an integrated positioning mechanism and drive mechanism. This particular positioning mechanism also does not comprise a braking mechanism to prevent the printer head from inadvertent contact with the receiving surface. A hybrid linear actuator drives the plunger attached to a carriage assembly (see FIG. 24b). Lead screw pitch and motor specifications are optimized for speed and precision. The carriage assembly is mounted to the linear guide system (see FIG. 25), which includes a custom sensor bracket attached to the linear stage, an optical interrupt sensor, and an optical flag integrated on the mounting plate.

Cartridge Carriers

Disclosed herein, in certain embodiments, are bioprinters for fabricating tissues and organs. In some embodiments, a bioprinter disclosed herein comprises one or more printer heads. In further embodiments, a printer head comprises a cartridge carrier for receiving and holding a plurality of cartridges, each cartridge comprising contents selected from: bio-ink, support material, and a combination thereof; and for each cartridge: a means for receiving and holding the cartridge that aligns the cartridge with a drive pathway; a drive means that dispenses the contents of the cartridge, the drive means operating independently from other drive means; and an actuation means that vertically positions the cartridge relative to a receiving surface to produce a particular three-dimensional geometry in the dispensed contents of the cartridge, the actuation means operating independently from other actuation means. In other embodiments, a printer head comprises a cartridge carrier for receiving and holding a plurality of cartridges, the cartridge carrier rotatable to align a selected cartridge with a drive pathway.

In some embodiments, the cartridge carrier is attached to a positionable printer head of the bioprinter and adapted to receive and hold a plurality of cartridges. In further embodiments, the cartridge carrier is rotatable to align a selected cartridge with a drive pathway of the bioprinter such that a drive mechanism engages the selected cartridge to dispense said contents.

In some embodiments, each cartridge comprises contents selected from one or more of: bio-ink and support material.

In some embodiments, the cartridge carrier is adapted to receive and holds a plurality of cartridges. In various embodiments, a cartridge carrier is adapted to receive and hold about 2, 3, 4, 5, 6, 7, 8, 9, 10, 11, 12, 13, 14, 15, 16, 17, 18, 19, 20 or more cartridges. In some embodiments, a cartridge carrier is adapted to receive and hold about 2 to about 10 cartridges. In some embodiments, a cartridge carrier is adapted to receive and hold 4 cartridges.

Many means for receiving and holding at least one cartridge are suitable. Suitable means for receiving and holding at least one cartridge include those that reliably, precisely, and securely attach at least one cartridge to a bioprinter. In various embodiments, the means for receiving and holding at least one cartridge is, by way of non-limiting example, magnetic attraction, a collet chuck grip, a ferrule, a nut, a barrel adapter, or a combination thereof.

In some embodiments, the cartridge carrier is cylindrical.

Dies

Disclosed herein, in certain embodiments, are bioprinters for fabricating tissues and organs. In some embodiments, a bioprinter disclosed herein comprises a die for controlling simultaneous deposition of a plurality of constructs in parallel, each construct having a particular three-dimensional geometry.

In some embodiments, the die comprises one or more input ports for receiving bio-ink or support material deposited from the bioprinter; and a plurality of output molds, each output mold comprising a well associated with each input port for shaping the bio-ink or support material; whereby the die allows simultaneous deposition of a plurality of constructs in parallel, each construct having a particular three-dimensional geometry.

In some embodiments, the die is permanently fixed. In other embodiments, the die is reversibly fixed. In some embodiments, each construct in the plurality of constructs has the same three-dimensional geometry. In some embodiments, the plurality of constructs is of homogeneous geometries. In other embodiments, the plurality of constructs is of heterogeneous geometries. In some embodiments, the plurality of constructs is bioprinted into standard assay plates.

In some embodiments, the die controls simultaneous deposition of 2-384 constructs in parallel. In some embodiments, the die controls simultaneous deposition of 96 constructs in parallel. In some embodiments, the die controls simultaneous deposition of 24 constructs in parallel. In some embodiments, the die controls simultaneous deposition of 12 constructs in parallel. In various embodiments, the die controls simultaneous deposition of about 2, 4, 6, 8, 12, 24, 36, 48, 96, or 384 constructs in parallel.

In some embodiments, the die is connected to a chamber for containing a uniform layer of bio-ink or support material, the chamber positioned between the die and a drive mechanism of the bioprinter.

In some embodiments, the die controls simultaneous deposition of a plurality of materials in parallel. In further embodiments, the die comprises an input port for each material.

Multiaxial Nozzles

Disclosed herein, in certain embodiments, are bioprinters for fabricating tissues and organs. In some embodiments, a bioprinter disclosed herein comprises one or more multiaxial nozzles for extrusion of one or more three-dimensional bioprinted tissues into a desired geometry.

In some embodiments, the one or more multiaxial nozzles are one or more specifically shaped nozzles such that bio-ink passing through the nozzles is shaped into a specific geometry. Non-limiting examples of the geometries are cylinders, hollow cylinders, polygons, sheets, and spheres. In some embodiments, the bioprinter has one or more coaxial nozzles. In some embodiments, the bioprinter has one or more triaxial nozzles. In some embodiments, the bioprinter has one or more coaxial or triaxial nozzles.

The multiaxial nozzle has dual or greater concentric flow capability to prepare a multiaxial tube with multiple-layer morphology consisting of a core layer (inner layer), a mantle layer (outer layer), and optionally one or more intermediate layers between the core and mantle layers. Dimensions of the nozzle vary based on design modifications.

In some embodiments of a nozzle, the outer diameter of the nozzle is 0.5 to 4 mm. In some embodiments of a nozzle, the outer diameter of the nozzle is 0.5 to 3 mm. In some embodiments of a nozzle, the outer diameter of the nozzle is 0.5 to 2 mm. In some embodiments of a nozzle, the outer diameter of the nozzle is 1 to 4 mm. In some embodiments of a nozzle, the outer diameter of the nozzle is 2 to 4 mm. In some embodiments of a nozzle, the outer diameter of the nozzle is 3 to 4 mm.

In some embodiments of a coaxial nozzle, the inner diameter of the nozzle is 0.1 to 1.5 mm. In some embodiments of a coaxial nozzle, the inner diameter of the nozzle is 0.1 to 1.3 mm. In some embodiments of a coaxial nozzle, the inner diameter of the nozzle is 0.1 to 1.0 mm. In some embodiments of a coaxial nozzle, the inner diameter of the nozzle is 0.1 to 0.8 mm. In some embodiments of a coaxial nozzle, the inner diameter of the nozzle is 0.1 to 0.6 mm. In some embodiments of a coaxial nozzle, the inner diameter of the nozzle is 0.1 to 0.4 mm. In some embodiments of a coaxial nozzle, the inner diameter of the nozzle is 0.6 to 1.5 mm. In some embodiments of a coaxial nozzle, the inner diameter of the nozzle is 0.6 to 1.3 mm. In some embodiments of a coaxial nozzle, the inner diameter of the nozzle is 0.6 to 1.0 mm.

In some embodiments, the multiaxial nozzle further comprises a means to independently regulate the flow of each of at least two different materials through at least two independent outputs to prepare the coaxial tube, wherein any two adjacent layers have different composition of materials with respect to each other. In various embodiments, the flow rate of extrusion through the nozzle is 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mL/min, or more, including increments therein.

In some embodiments of a coaxial nozzle, the flow rate of the inner layer bio-ink is equivalent to the flow rate of the outer layer bio-ink. In some embodiments of a coaxial nozzle, the flow rate of the inner layer bio-ink is different from the flow rate of the outer layer bio-ink. In some embodiments of a coaxial nozzle, the flow rate of the inner layer bio-ink is 50% faster than the flow rate of the outer layer bio-ink. In some embodiments of a coaxial nozzle, the flow rate of the inner layer bio-ink is twice as fast as the flow rate of the outer layer bio-ink. In some embodiments, the flow rate of any one of the layers is slower than an adjacent layer.

In some embodiments, the multiaxial nozzle is capable of continuous extrusion and/or sputter extrusion. In some embodiments of a coaxial nozzle, the core layer is prepared by sputter extrusion as the mantle layer is prepared by continuous extrusion. In other embodiments of a coaxial nozzle, the core layer is prepared by continuous extrusion as the mantle layer is prepared by sputter extrusion.

Figure 34:
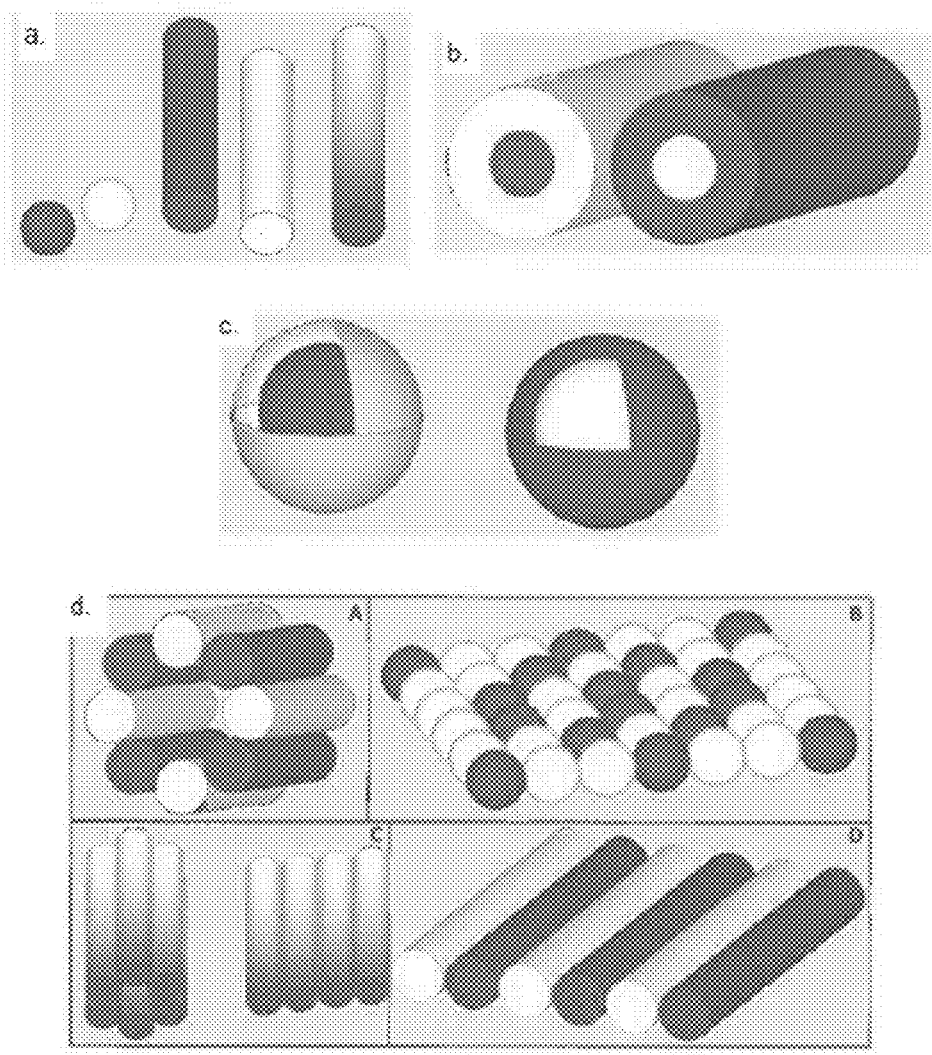
FIG. 34 illustrates non-limiting examples of bio-printing constructs, some of which comprise I-bio-ink (shown in darker shading); in this case, (a) spheres or cylinders are shown; (b) coaxial cylinders are shown; (c) coaxial spheres are shown; and (d) complex structures derived from I-bio-ink and normal bio-ink (bio-ink without immunomodulatory cells).

Spheres and cylinders (e.g., FIG. 34a) represent fundamental geometries using the methods described herein. In various embodiments of a bioprinted structure, I-bio-ink (shown in dark shading in FIG. 34a) is the sole component, is present in a gradient with normal bio-ink (i.e., bio-ink without immunomodulatory cells), or is absent altogether. Coaxial or triaxial extrusion nozzles facilitate multi-laminated structures of a cylindrical- (e.g., FIG. 34b: I-bio-ink is placed in the core layer or mantle layer) or spherical-nature (e.g., FIG. 34c: I-bio-ink is placed in the core layer or mantle layer). Triaxial deposition involves an additional symmetrically nestled cylinder when viewed in cross-section (not shown). These geometries represent variable building blocks that are utilized to construct much larger and more complex structures with the goal of recapitulating a degree of tissue function in vitro and at tissue-like cellular densities with or without the inclusion of biomaterials. Thus some representative assemblages utilizing the basic building blocks are presented in FIG. 34d: (A) patterning example with tubular construct, (B) patches generated from spheres, where patterning can be varied with precision on the resolution of the spherical bio-ink, (C) use of gradient I-bio-ink cylinders in patches and tubular constructs, and (D) use of homogeneous I-bio-ink and normal bio-ink cylinders in patches with simple pattern.

Cartridges

Disclosed herein, in certain embodiments, are bioprinters for fabricating tissues and organs. In some embodiments, a cartridge attached to the bioprinter comprises bio-ink or support material. In some embodiments, the bioprinter dispenses bio-ink or support material in a specific pattern and at specific positions in order to form a specific cellular construct, tissue, or organ. In order to fabricate complex tissue constructs, the bioprinter deposits the bio-ink or support material at precise speeds and in uniform amounts. Thus, there is a need for a cartridge with (a) a dispensing orifice that is smooth or substantially smooth, and (b) an internal surface that is smooth or substantially smooth. As used herein, "cartridge" means any object that is capable of receiving (and holding) a bio-ink and/or support material.

In some embodiments, a cartridge disclosed herein comprises bio-ink. In some embodiments, a cartridge disclosed herein comprises support material. In some embodiments, a cartridge disclosed herein comprises a combination of bio-ink and support material. In some embodiments, a cartridge disclosed herein comprises bio-ink comprising mammalian cells.

Disclosed herein, in certain embodiments, are cartridges for use with a bioprinter disclosed herein, comprising at least one dispensing orifice. In some embodiments, a cartridge comprises one dispensing orifice. In various other embodiments, a cartridge comprises 2, 3, 4, 5, 6, 7, 8, 9, 10, 11, 12, 13, 14, 15, 20, 30, 40, 50, 60, 70, 80, 90, 100, or more dispensing orifices. In further embodiment, the edges of a dispensing orifice are smooth or substantially smooth.

Many shapes are suitable for the dispensing orifices disclosed herein. In various embodiments, suitable shapes for dispensing orifices include, by way of non-limiting examples, circular, ovoid, triangular, square, rectangular, polygonal, and irregular. In some embodiments, the orifice is circular. In other embodiments, the orifice is square. In yet other embodiments, the orifice is oval, oblong, or rectangular and dispenses solid or semi-solid bio-ink and/or support materials in a ribbon-like form.

In some embodiments, the internal surface of the cartridge is smooth or substantially smooth. In some embodiments, the cartridge is comprised of a rigid structure to facilitate calibration. In some embodiments, the walls of the cartridge are comprised of a material that resists attachment of cells. In some embodiments, the cartridges are comprised of a material that is biocompatible.

In some embodiments, the cartridge is a disposable, single-use cartridge. The disposable, single-use cartridge is installed into an appropriate means for receiving and holding the cartridge on the bioprinter that ultimately aligns the cartridge with a drive pathway. The cartridge is preferably filled in a streamlined manufacturing process and is easily installed into and removed from the print head of the bioprinter. In some embodiments, the cartridge is a plastic syringe.

Figure 16:
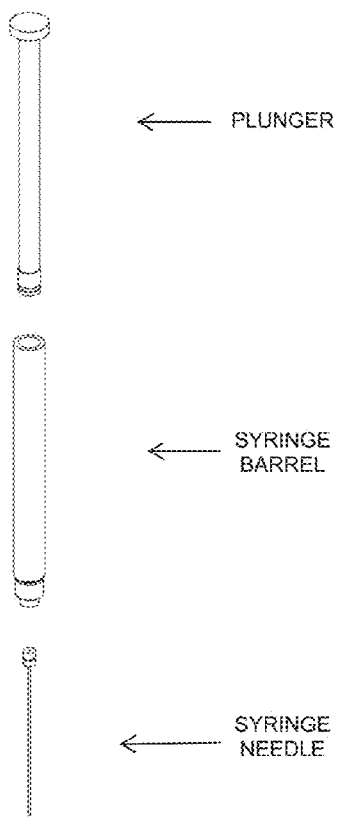
FIG. 16 illustrates a non-limiting example of a disposable, single use bio-ink cartridge in the form of a plastic syringe; in this case, an exploded view is shown.
Figure 17:
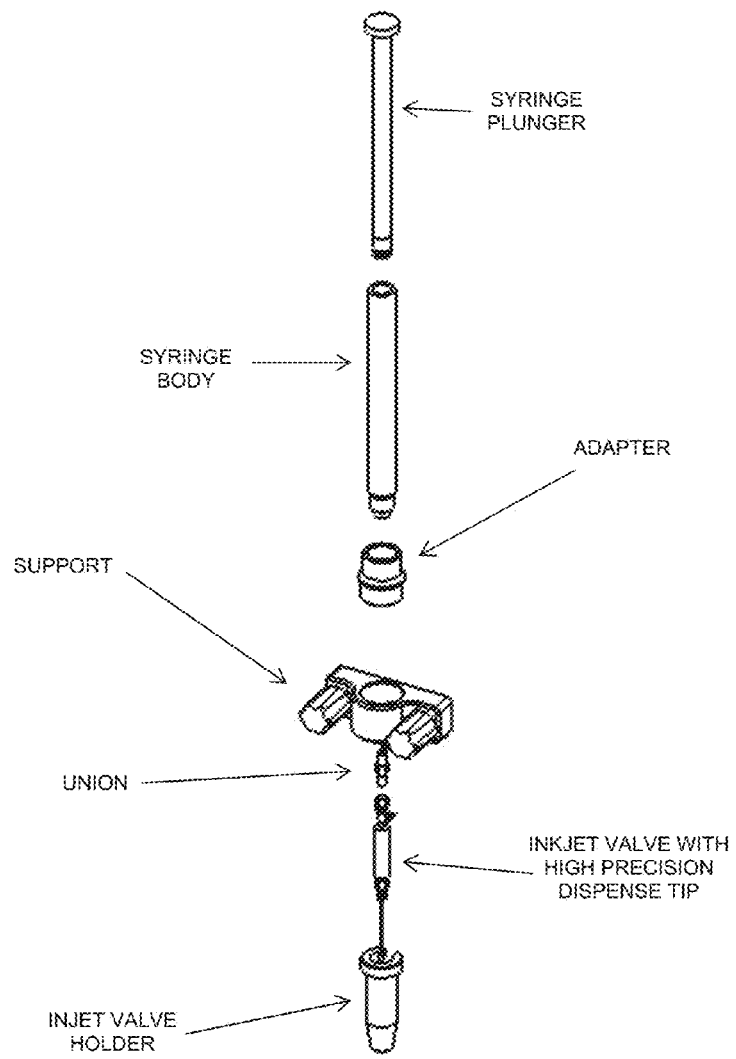
FIG. 17 illustrates a non-limiting example of a cartridge configured as part of an ink jet head; in this case, in an exploded view, the ink jet head comprises a syringe body with syringe plunger, a syringe adapter, a support for the ink jet head, an ink jet valve coupled to a high precision dispense tip, a union element between the syringe adapter and the ink jet valve, and an ink jet valve holder.

Referring to FIG. 16, in a particular embodiment, a disposable, single-use cartridge is a plastic syringe, shown here with a syringe needle as the dispensing orifice.

Many types of cartridges are suitable for use with bioprinters disclosed herein and the methods of using the same. In some embodiments, a cartridge is compatible with bioprinting that involves extruding a semi-solid or solid bio-ink or a support material through one or more dispensing orifices. In some embodiments, a cartridge is compatible with bioprinting that involves dispensing a liquid or semi-solid cell solution, cell suspension, or cell concentration through one or more dispensing orifices. In some embodiments, a cartridge is compatible with non-continuous bioprinting. In some embodiments, a cartridge is compatible with continuous and/or substantially continuous bioprinting. In some embodiments, the cartridge is connected to a remote reservoir of contents. A remote reservoir suitably contains a wide range of volumes. In various embodiments, a remote reservoir suitably contains about 1, 2, 3, 4, 5, 6, 7, 8, 9, 10 mL of contents or more. In various further embodiments, a remote reservoir suitably contains about 10, 20, 30, 40, 50, 60, 70, 80, 90, 100 mL of contents or more. In still further embodiments, a remote reservoir suitably contains about 100, 200, 300, 400, 500, 600, 700, 800, 900, 1000 mL of contents or more.

In some embodiments, a cartridge is a capillary tube or a micropipette. In some embodiments, a cartridge is a syringe or a needle, or a combination thereof. Many internal diameters are suitable for substantially round or cylindrical cartridges. In various embodiments, suitable internal diameters include, by way of non-limiting examples, 1, 10, 50, 100, 200, 300, 400, 500, 600, 700, 800, 900, 1000 or more µm, including increments therein. In other various embodiments, suitable internal diameters include, by way of non-limiting examples, 1, 2, 3, 4, 5, 6, 7, 8, 9, 10, 20, 30, 40, 50, 60, 70, 80, 90, 100 or more mm, including increments therein. In some embodiments, a cartridge has an internal diameter of about 1 µm to about 1000 µm. In a particular embodiment, a cartridge has an internal diameter of about 500 µm. In another particular embodiment, a cartridge has an internal diameter of about 250 µm. Many internal volumes are suitable for the cartridges disclosed herein. In various embodiments, suitable internal volumes include, by way of non-limiting examples, 1, 10, 20, 30, 40, 50, 100, 200, 300, 400, 500, 600, 700, 800, 900, 1000 or more including increments therein. In other various embodiments, suitable internal volumes include, by way of non-limiting examples, 1, 2, 3, 4, 5, 10, 20, 30, 40, 50, 60, 70, 80, 90, 100, 200, 300, 400, 500 or more ml, including increments therein. In some embodiments, a cartridge has a volume of about 1 µl to about 50 In a particular embodiment, a cartridge has a volume of about 5 µl.

In some embodiments, a cartridge is compatible with inkjet printing of bio-ink and/or support material onto a receiving surface such as that described in U.S. Pat. No. 7,051,654. In further embodiments, a cartridge includes dispensing orifices in the form of voltage-gated nozzles or needles under the control of the computer code described herein.

In some embodiments, the ink jet printing requires a syringe pump closely coupled to a specialized high speed ink jet solenoid valve. In some embodiments, dispense volume is controlled by syringe pressure, valve actuation time and a precision dispense tip. In some embodiments, the precision dispense control is controlled through a two stage electronic valve, wherein a high voltage pulse is followed by a lower voltage hold current. In further embodiments, the high voltage pulse is 12 to 40 VDC, and the lower voltage hold current is 12 to 24 VDC. In some embodiments, the valve timing is controlled by TTL control voltage. In some embodiments, the pulse is 0.35 to 2.0 milliseconds. In some embodiments, the syringe pressure is 0 to 120 psig.

In some embodiments, the cartridge is primed. In some embodiments, priming the cartridge increases the accuracy of the dispensing, deposition, or extrusion process. As used herein, "primed" means the contents of the cartridge are made ready for dispensing, deposition, or extrusion by compacting and advancing the contents of the cartridge until the material to be dispensed (bio-ink or supporting material) is located in a position in contact with the dispensing orifice. See, e.g., FIG. 3. In some embodiments, the cartridge is primed when the contents are compact or substantially compact, and the contents are in physical contact with the orifice of the cartridge.

In some embodiments, a cartridge is marked to indicate the composition of its contents. In further embodiments, a cartridge is marked to indicate the composition of a bio-ink and/or support material contained therein. In some embodiments, the surface of the cartridge is colored. In some embodiments, the outer surface of the cartridge is dyed, painted, marked with a pen, marked by a sticker, or a combination thereof.

In some embodiments, the outer surface of a cartridge is marked to increase the opacity of the surface of the cartridge (e.g., to increase the amount of a laser beam that is reflected off the surface of the cartridge). In some embodiments, the surface of a cartridge is colored. In some embodiments, the outer surface of a cartridge is scored. As used herein, "scored" means marking the surface of a cartridge to reduce the smoothness of the surface. Any suitable method is used to score the surface of a cartridge (e.g., application of an acidic substance, application of a caustic substance, application of an abrasive substance, etc.). In some embodiments, the outer surface of a cartridge is painted, polished (e.g., fire polished), etched (e.g., laser etched), marked with a pen, marked by a sticker, or a combination thereof.

Grip

Disclosed herein, in certain embodiments, are bioprinters for fabricating tissues and organs. In some embodiments, a cartridge attached to a bioprinter comprises bio-ink and/or support material. In some embodiments, the bioprinter dispenses the bio-ink and/or support material in a specific pattern and at specific positions in order to form a specific cellular construct, tissue, or organ. In some embodiments, a cartridge comprising bio-ink is disposable. In some embodiments, the cartridge is ejected from the bioprinter following extrusion of the contents. In some embodiments, a new cartridge is subsequently attached to the bioprinter.

In order to fabricate complex structures, the bioprinters disclosed herein dispense bio-ink and/or support material from a cartridge with a suitable repeatable accuracy. In various embodiments, suitable repeatable accuracies include those of about ±5, 10, 20, 30, 40, or 50 µm on any axis. In some embodiments, the bioprinters disclosed herein dispense bio-ink and/or support material from a cartridge with a repeatable accuracy of about ±20 µm. However, uncontrolled removal and insertion of cartridges can result in alterations of the position of the printer head (and thus the cartridges) with respect to the tissue construct, such that precision of the placement of the first bio-ink particle deposited from a new cartridge optionally varies relative to the last bio-ink particle deposited from the previous cartridge. Thus, there is a need for a method of attaching and securing a cartridge to a printer head, wherein said attaching and securing produce minimal alterations in the position of the printer head.

Disclosed herein, in certain embodiments, are methods of attaching a cartridge to a bioprinter, comprising: (a) inserting the cartridge into a collet chuck, wherein the collet chuck is attached to a printer head of the bioprinter; and (b) adjusting the outer collar of the collet chuck; wherein the inserting and adjusting do not substantially alter the position of the printer head.

Disclosed herein, in certain embodiments, are systems for attaching a cartridge to a bioprinter, comprising: a means for receiving and securing a cartridge to a printer head of a bioprinter; wherein use of the means for receiving and securing the cartridge do not substantially alter the position of the printer head. In some embodiments, the means for receiving and securing the cartridge to a printer head is a chuck or ferrule. As used herein, "chuck" means a holding device consisting of adjustable jaws. In some embodiments, the means for receiving and securing the cartridge to a printer head is a collet. As used herein, "collet" means a subtype of chuck—that forms a collar around the object to be held and exerts a strong clamping. As used herein, "ferrule" means a band (e.g., a metal band) used to secure one object to another. In some embodiments, the means for receiving and securing the cartridge to a printer head is a barrel adaptor. As used herein, "barrel adaptor" means a threaded tube used to secure one object to another.

UV Module

Disclosed herein, in certain embodiments, are bioprinters for fabricating tissues and organs. In some embodiments, a bioprinter comprises an ultraviolet (UV) light module. In further embodiments, a UV module enables a bioprinter disclosed herein to automatically cure and print UV cross-linkable materials. In some embodiments, a UV module comprises a light chamber for exposing the contents of a cartridge (e.g., a glass capillary tube) to UV light. In some embodiments, a UV module comprises a UV light line to expose the contents of a cartridge to UV light evenly along its length. In some embodiments, a UV module comprises a slot to accept an optional attenuation filter that reduces the intensity of UV light to which the contents of a cartridge is exposed. In some embodiments, a UV module is integrated with a bioprinter. In various further embodiments, a UV module is permanently, semi-permanently, or reversibly attached to a bioprinter. In other embodiments, a UV module is not attached to a bioprinter.

In some embodiments, a UV module described herein is used by first aspirating uncured material into a glass capillary tube. In further embodiments, the glass capillary then is lowered into the light chamber, where a high power fiber optic light line transmits UV light from a UV light source across the length of the capillary. In still further embodiments, once cured (e.g., cross-linked), the glass capillary is lifted out of the light chamber and the material is ready to print (e.g., be extruded or deposited, etc.). For applications where the contents of a cartridge include bio-ink and/or support material that comprises cells, an optional attenuation filter is placed between the capillary and the light guide to achieve lower UV intensities.

Many UV light sources are suitable for use with the UV module described herein. UV light is electromagnetic radiation with a wavelength in the range 10 nm to 400 nm and energies from 3 eV to 124 eV. UV light, in some cases, alters chemical bonds in molecules and can cause chemical reactions. UV light from various sources is characterized by having many suitable wavelengths and many suitable associated energies. See Table 1, infra.

TABLE 1

| UV light type | Wavelength range (nanometers) | Energy per photon (electronvolts) |
|---|---|---|
| Ultraviolet A (UVA) or long wave | 400-315 nm | 3.10-3.94 eV |
| Near UV | 400-300 nm | 3.10-4.13 eV |
| Ultraviolet B (UVB) or medium wave | 315-280 nm | 3.94-4.43 eV |
| Middle UV | 300-200 nm | 4.13-6.20 eV |
| Ultraviolet C (UVC) or short wave | 280-100 nm | 4.43-12.4 eV |

TABLE 1-continued

| UV light type | Wavelength range (nanometers) | Energy per photon (electronvolts) |
|---|---|---|
| Far UV | 200-122 nm | 6.20-10.2 eV |
| Vacuum UV | 200-100 nm | 6.20-12.4 eV |
| Low UV | 100-88 nm | 12.4-14.1 eV |
| Super UV | 150-10 nm | 8.28-124 eV |
| Extreme UV | 121-10 nm | 10.25-124 eV |

In some embodiments, suitable sources of UV light include, by way of non-limiting examples, UV lamps, UV fluorescent lamps, UV LEDs, UV lasers, and the like. A UV lamp (e.g., black light, black light blue or BLB lamps, etc.) emits long-wave UV radiation and very little visible light. Fluorescent black lights are typically made using a UV-emitting phosphor. The phosphor typically used for a near 368-371 nm emission peak is either europium-doped strontium fluoroborate ($SrB_4O_7F:Eu^{2+}$) or europium-doped strontium borate ($SrB_4O_7:Eu^{2+}$), whereas the phosphor used to produce a peak around 350-353 nm is lead-doped barium silicate ($BaSi_2O_5:Pb^+$). Fluorescent black lights are also typically made using Wood's glass, a nickel-oxide-doped glass, which blocks almost all visible light above 400 nm. A black light may also be formed, very inefficiently, by simply using Wood's glass instead of clear glass as the envelope for a common incandescent bulb. UV fluorescent lamps without a phosphorescent coating to convert UV to visible light, emit ultraviolet light with two peaks at 253.7 nm and 185 nm due to the peak emission of the mercury within the bulb. With the addition of a suitable phosphor (phosphorescent coating), they can be modified to produce UVA or UVB. Light-emitting diodes (LEDs) can be manufactured to emit light in the UV range, although practical LED arrays are limited below 365 nm. UV laser diodes and UV solid-state lasers can be manufactured to emit light in the UV range. Direct UV-emitting laser diodes are available at 375 nm. UV diode lasers have been demonstrated using crystals of cerium doped with lithium strontium aluminum fluoride (Ce:LiSAF). Wavelengths shorter than 375 nm are generated from diodes in solid-state modules that use frequency doubling or tripling diode-pumped solid state (DPSS) technology. Wavelengths available include 262, 266, 349, 351, 355, and 375 nm.

Figure 19:
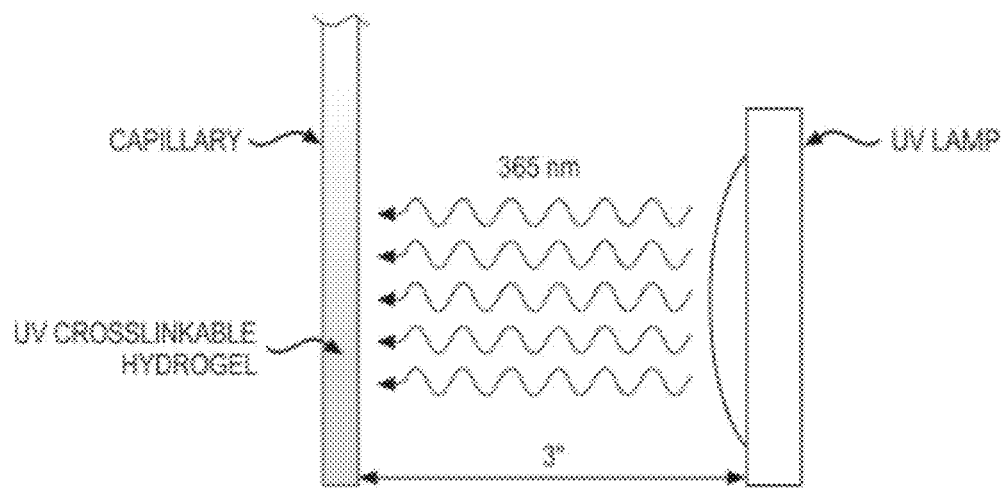
FIG. 19 illustrates a non-limiting schematic diagram depicting exemplary parameters for exposing a UV cross-linkable material to a UV light source in the context of a bioprinter.

Referring to FIG. 19, in a particular embodiment, a UV module comprises a UV light source that is a UV lamp. Further in this embodiment, a cartridge includes a glass capillary tube into which a UV cross-linkable material is aspirated. The cartridge is positioned within the light chamber of the UV module such that it is about 3 inches from the UV lamp. The UV lamp in this embodiment emits UV light with a wavelength of about 365 nm.

Figure 20:
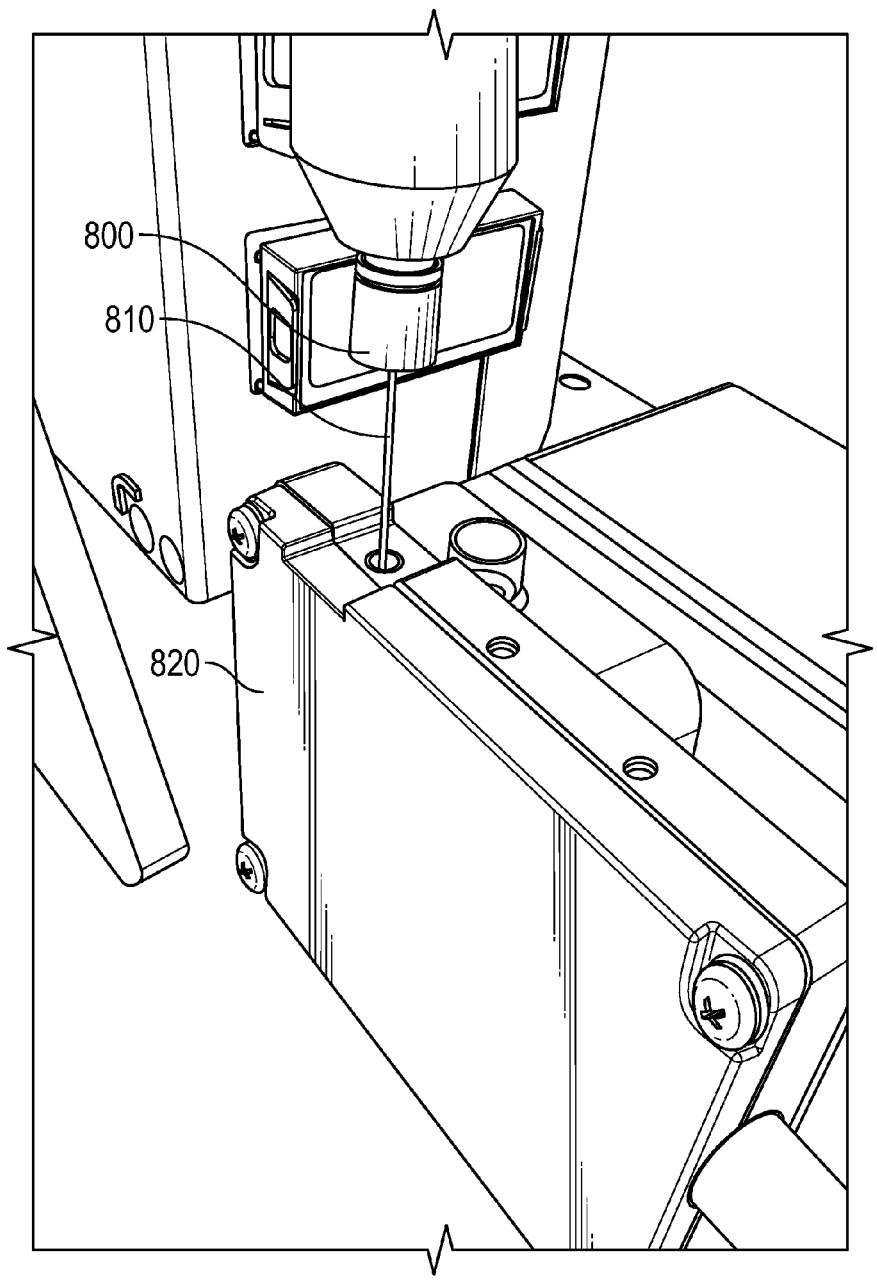
FIG. 20 illustrates a non-limiting example of a NovoGen MMX™ bioprinter including a UV module; in this case, a printer head is positioned such that a capillary tube is partially introduced to a UV module.

Referring to FIG. 20, in a particular embodiment, a bioprinter includes a printer head 800, which holds a cartridge 810. In this embodiment, a cartridge 810 includes a glass capillary tube which is partially lowered into a UV light module 820 attached to the bioprinter. The UV module 820 in this case, comprises a housing, a cover, and an opening to allow introduction of the cartridge 810.

Figure 21:
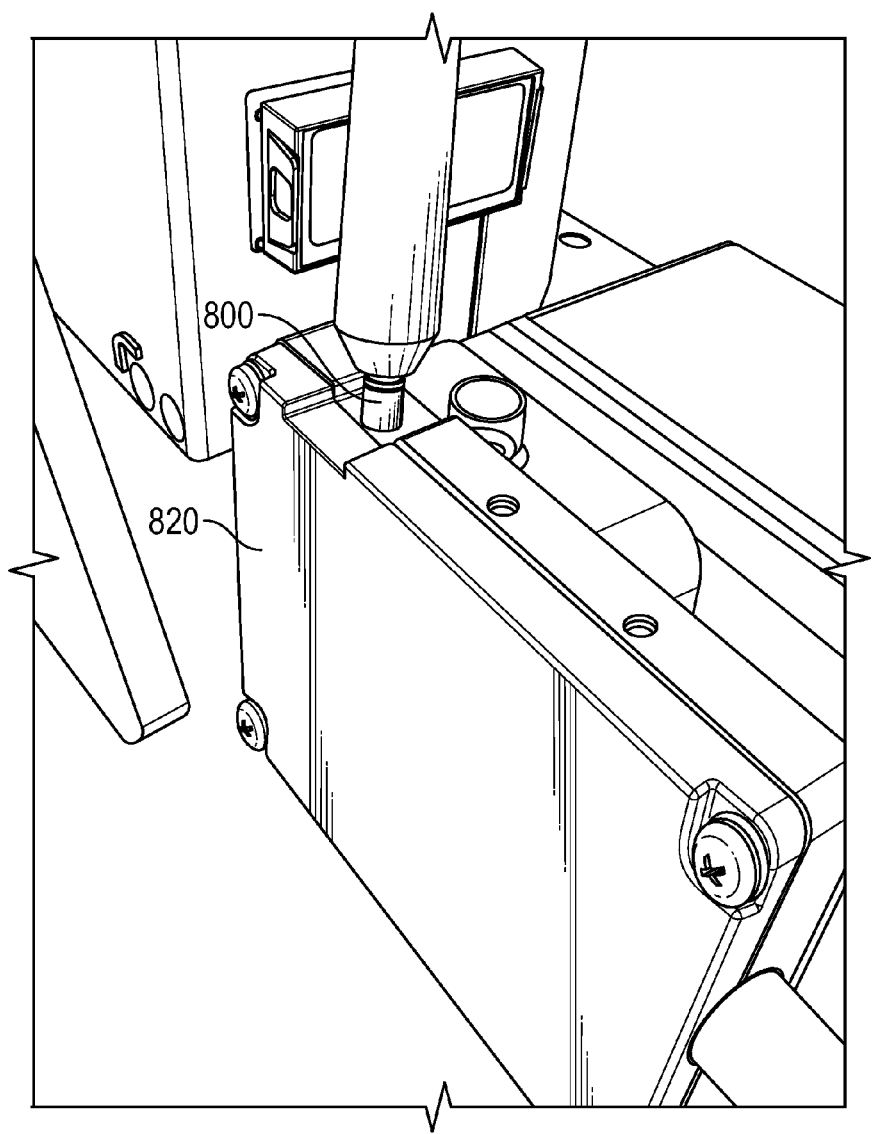
FIG. 21 illustrates a non-limiting example of a NovoGen MMX™ bioprinter including a UV module; in this case, a printer head is positioned such that a capillary tube is entirely introduced to a UV module.

Referring to FIG. 21, in a further particular embodiment, a printer head 800, which holds a cartridge 810 is completely lowered into a UV light module 820.

In some embodiments, a UV module enables a bioprinter disclosed herein to automatically cure and print UV cross-linkable materials by exposing them to UV light for a predetermined period of time. Many durations of exposure to a UV light source are suitable. In light of the disclosure provided herein, those of skill in the art will recognize that particular UV cross-linkable materials are suited to particular exposure times. In some embodiments, exposure time is selected to completely UV cross-link a material, resulting in a more solid structure. In other embodiments, exposure time is selected to partially UV cross-link a material, resulting in a more semi-solid structure. In various embodiments, suitable exposure times include, by way of non-limiting examples, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more seconds. In other various embodiments, suitable exposure times include, by way of non-limiting examples, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more minutes.

In some embodiments, exposure time is about 5 seconds to about 15 minutes. In further embodiments, exposure time is about 10 seconds to about 10 minutes. In still further embodiments, exposure time is about 15 seconds to about 5 minutes. In some cases, exposure time is adjusted for the presence of cells in a UV cross-linkable material.

Receiving Surface

Disclosed herein, in certain embodiments, are bioprinters for fabricating tissues and organs. In some embodiments, the bioprinter dispenses a plurality of elements, sections, and/or areas of bio-ink and/or support material onto a receiving surface. In further embodiments, dispensing occurs in a specific pattern and at specific positions. In still further embodiments, the locations at which the bioprinter deposits bio-ink and/or support material onto a receiving surface are defined by user input and translated into computer code.

In some embodiments, each of the elements, sections, and/or areas of bio-ink and/or support material has dimensions of less than 300 mm×300 mm×160 mm. By way of example only, the dimensions of a section of bio-ink or support material are optionally 75 mm×5.0 mm×5.0 mm; 0.3 mm×2.5 mm×2.5 mm; 1 mm×1 mm×50 mm; or 150 mm×150 mm×80 mm. Due to the generally small size of each section, and in some cases, the high degree of precision required, minute imperfections in the receiving surface may result in imperfections (and possibly, failure) of a cellular construct, tissue, or organ. Thus, there is a need for a substantially smooth and substantially flat receiving surface, or a defined or substantially defined receiving surface, that is able to receive sections of bio-ink and/or support material.

Disclosed herein, in certain embodiments, are receiving surfaces for receiving one or more structures generated by the bioprinter disclosed herein. In some embodiments, the receiving surface is flat or substantially flat. In some embodiments, the receiving surface is smooth or substantially smooth. In some embodiments, the receiving surface is flat or substantially flat. In some embodiments, the receiving surface is defined or substantially defined. In other embodiments the receiving surface is designed specifically to accommodate the shape, size, texture, or geometry of a specific bioprinted structure. In further embodiments, the receiving surface controls or influences the size, shape, texture, or geometry of a bioprinted construct.

In some embodiments, the receiving surface comprises a solid material, a semi-solid material, or a combination thereof. In some embodiments, the receiving surface comprises glass, coated glass, plastic, coated plastic, metal, a metal alloy, or a combination thereof. In some embodiments, the receiving surface comprises a gel. In some embodiments, the receiving surface and any coatings thereon are biocompatible. In various embodiments, the receiving surface comprises any of the support materials and/or confinement materials disclosed herein. In specific embodiments, the receiving surface comprises polymerized NovoGel™ or polymerized agarose, polymerized gelatin, extracellular matrix (or components thereof), collagen, or a combination thereof. In some embodiments, the receiving surface is a standard assay plate. In some embodiments, the receiving surface is a transwell insert fitted into a 24-well transwell carrier.

Software

Disclosed herein, in certain embodiments, are bioprinters for fabricating tissues and organs. In some embodiments, one or more cartridges attached to the bioprinter comprise bio-ink and/or support material. In some embodiments, the bioprinter dispenses bio-ink or support material in a specific pattern and at specific positions in order to form a specific cellular construct, tissue, or organ.

In order to fabricate complex tissue constructs, the bioprinter deposits the bio-ink or support material at precise locations (in two or three dimensions) on a receiving surface. In some embodiments, the locations at which the bioprinter deposits bio-ink and/or support material are defined by user input and translated into computer code. In further embodiments, the computer code includes a sequence of instructions, executable in the central processing unit (CPU) of a digital processing device, written to perform a specified task. In some embodiments, additional bioprinting parameters including, by way of non-limiting examples, print height, pump speed, robot speed, control of variable dispensing orifices, UV intensity, and UV exposure time are defined by user input and translated into computer code. In other embodiments, such bioprinting parameters are not directly defined by user input, but are derived from other parameters and conditions by the computer code described herein.

Disclosed herein, in certain embodiments, are methods for fabricating tissue constructs, tissues, and organs, comprising: a computer module receiving input of a visual representation of a desired tissue construct; a computer module generating a series of commands, wherein the commands are based on the visual representation and are readable by a bioprinter; a computer module providing the series of commands to a bioprinter; and the bioprinter depositing bio-ink and/or support material according to the commands to form a construct with a defined geometry.

Non-Transitory Computer Readable Storage Medium

In some embodiments, the locations at which the bioprinter deposits the bio-ink and/or support material are defined by user input and translated into computer code. In some embodiments, the devices, systems, and methods disclosed herein further comprise non-transitory computer readable storage media or storage media encoded with computer readable program code. In further embodiments, a computer readable storage medium is a tangible component of a digital processing device such as a bioprinter (or a component thereof) or a computer connected to a bioprinter (or a component thereof). In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the storage media.

Computer Modules

In some embodiments, the devices, systems, and methods described herein comprise software, server, and database modules. In some embodiments, a "computer module" is a software component (including a section of code) that interacts with a larger computer system. In further embodiments, a software module (or program module) comes in the form of one or more files and typically handles a specific task within a larger software system.

In some embodiments, a module is included in one or more software systems. In other embodiments, a module is integrated with one or more other modules into one or more software systems. A computer module is optionally a stand-alone section of code or, optionally, code that is not separately identifiable. In some embodiments, the modules are in a single application. In other embodiments, the modules are in a plurality of applications. In some embodiments, the modules are hosted on one machine. In other embodiments, the modules are hosted on a plurality of machines. In some embodiments, the modules are hosted on a plurality of machines in one location. In other embodiments, the modules are hosted a plurality of machines in more than one location. Further described herein is the formatting of location and positioning data. In some embodiments, the data files described herein are formatted in any suitable data serialization format including, by way of non-limiting examples, tab-separated values, comma-separated values, character-separated values, delimiter-separated values, XML, JSON, BSON, and YAML. A key feature of a computer module is that it allows an end user to use a computer to perform the identified functions.

Graphic User Interface

In some embodiments, a computer module comprises a graphic user interface (GUI). As used herein, "graphic user interface" means a user environment that uses pictorial as well as textual representations of the input and output of applications and the hierarchical or other data structure in which information is stored. In some embodiments, a computer module comprises a display screen. In further embodiments, a computer module presents, via a display screen, a two-dimensional GUI. In other embodiments, a computer module presents, via a display screen, a three-dimensional GUI such as a virtual reality environment. In some embodiments, the display screen is a touchscreen or multitouch-screen and presents an interactive GUI.

In some embodiments, the display screen presents a GUI that consists essentially of a grid comprising regularly spaced objects of substantially the same shape and substantially equal size. The objects presented have any suitable shape. In some embodiments, suitable shapes for objects include, by way of non-limiting examples, circle, oval, square, rectangle, triangle, diamond, polygon, or a combination thereof.

In some embodiments, a user defines the content of one or more objects to form a two-dimensional or three-dimensional visual representation of a desired tissue construct. See, e.g., FIG. 5. In some embodiments, the user-defined content of an object is, by way of non-limiting examples, a bio-ink with various compositions or support material with various compositions. In some embodiments, the user defines the content of an object by modifying the color of the cell or the shape of the object.

Bio-Ink

Disclosed herein, in certain embodiments, are devices, systems, and methods for fabricating tissues and organs. In some embodiments, the devices comprise one or more printer heads for receiving and holding at least one cartridge that optionally contains bio-ink. In some embodiments, the methods comprise the use of bio-ink. In further embodiments, the tissues and organs fabricated by use of the devices, systems, and methods described herein comprise bio-ink at the time of fabrication or thereafter.

Bio-ink has high cell density or native-like cell density. In various embodiments, the cell density of bio-ink is 30, 35, 40, 45, 50, 55, 60, 65, 70, 75, 80, 85, 90, or 95 percent, or more, including increments therein. In some embodiments, bio-ink consists essentially of cells.

In some embodiments, "bio-ink" includes liquid, semi-solid, or solid compositions comprising a plurality of cells. In some embodiments, bio-ink comprises liquid or semi-solid cell solutions, cell suspensions, or cell concentrations. In further embodiments, a cell solution, suspension, or concentration comprises a liquid or semi-solid (e.g., viscous) carrier and a plurality of cells. In still further embodiments, the carrier is a suitable cell nutrient media, such as those described herein. In some embodiments, bio-ink comprises semi-solid or solid multicellular aggregates or multicellular bodies. In further embodiments, the bio-ink is produced by 1) mixing a plurality of cells or cell aggregates and a biocompatible liquid or gel in a pre-determined ratio to result in bio-ink, and 2) compacting the bio-ink to produce the bio-ink with a desired cell density and viscosity. In some embodiments, the compacting of the bio-ink is achieved by centrifugation, tangential flow filtration ("TFF"), or a combination thereof. In some embodiments, the compacting of the bio-ink results in a composition that is extrudable, allowing formation of multicellular aggregates or multicellular bodies. In some embodiments, "extrudable" means able to be shaped by forcing (e.g., under pressure) through a nozzle or orifice (e.g., one or more holes or tubes). In some embodiments, the compacting of the bio-ink results from growing the cells to a suitable density. The cell density necessary for the bio-ink will vary with the cells being used and the tissue or organ being produced. In some embodiments, the cells of the bio-ink are cohered and/or adhered. In some embodiments, "cohere," "cohered," and "cohesion" refer to cell-cell adhesion properties that bind cells, multicellular aggregates, multicellular bodies, and/or layers thereof. In further embodiments, the terms are used interchangeably with "fuse," "fused," and "fusion." In some embodiments, the bio-ink additionally comprises support material, cell culture medium, extracellular matrix (or components thereof), cell adhesion agents, cell death inhibitors, anti-apoptotic agents, anti-oxidants, extrusion compounds, and combinations thereof.

Cells

Disclosed herein, in various embodiments, are bio-inks that include liquid, semi-solid, or solid compositions comprising a plurality of cells. In some embodiments, bio-ink comprises liquid or semi-solid cell solutions, cell suspensions, or cell concentrations. In some embodiments, any mammalian cell is suitable for use in bio-ink and in the fabrication of tissues and organs using the devices, systems, and methods described herein. In various embodiments, the cells are any suitable cell. In further various embodiments, the cells are vertebrate cells, mammalian cells, human cells, or combinations thereof. In some embodiments, the type of cell used in a method disclosed herein depends on the type of cellular construct, tissue, or organ being produced. In some embodiments, the bio-ink comprises one type of cell (also referred to as a "homogeneous ink"). In some embodiments, the bio-ink comprises more than one type of cell (also referred to as a "heterogeneous ink").

In further embodiments, the cells are, by way of non-limiting examples, contractile or muscle cells (e.g., skeletal muscle cells, cardiomyocytes, smooth muscle cells, and myoblasts), connective tissue cells (e.g., bone cells, cartilage cells, fibroblasts, and cells differentiating into bone forming cells, chondrocytes, or lymph tissues), bone marrow cells, endothelial cells, skin cells, epithelial cells, breast cells, vascular cells, blood cells, lymph cells, neural cells, Schwann cells, gastrointestinal cells, liver cells, pancreatic cells, lung cells, tracheal cells, corneal cells, genitourinary cells, kidney cells, reproductive cells, adipose cells, parenchymal cells, pericytes, mesothelial cells, stromal cells, undifferentiated cells (e.g., embryonic cells, stem cells, and progenitor cells), endoderm-derived cells, mesoderm-derived cells, ectoderm-derived cells, and combinations thereof.

In some embodiments, the cells are adult, differentiated cells. In further embodiments, "differentiated cells" are cells with a tissue-specific phenotype consistent with, for example, a smooth muscle cell, a fibroblast, or an endothelial cell at the time of isolation, wherein tissue-specific phenotype (or the potential to display the phenotype) is maintained from the time of isolation to the time of use. In other embodiments, the cells are adult, non-differentiated cells. In further embodiments, "non-differentiated cells" are cells that do not have, or have lost, the definitive tissue-specific traits of for example, smooth muscle cells, fibroblasts, or endothelial cells. In some embodiments, non-differentiated cells include stem cells. In further embodiments, "stem cells" are cells that exhibit potency and self-renewal. Stem cells include, but are not limited to, totipotent cells, pluripotent cells, multipotent cells, oligopotent cells, unipotent cells, and progenitor cells. Stem cells are optionally embryonic stem cells, adult stem cells, amniotic stem cells, and induced pluripotent stem cells. In yet other embodiments, the cells are a mixture of adult, differentiated cells and adult, non-differentiated cells.

In some embodiments, the cells are immunomodulatory cells. In further embodiments, the immunomodulatory cells are selected from mesenchymal stem cells (MSCs) or macrophages, or a combination of both. In some embodiments, the mesenchymal stem cells are bone and/or adipose derived. In some embodiments, the macrophages are sourced from tissue and/or blood). In some embodiments, the macrophages are M2-activated macrophages. In some embodiments, the M2-activated macrophages, isolated from spleen, blood, and/or other tissue locations, are added to a bio-ink admixture. In some embodiments, neutral macrophages are activated in vitro prior to being added to a bio-ink admixture. In some embodiments, neutral macrophages are added to a bio-ink admixture that incorporates the necessary cytokines for M2-activation of the macrophages. In some embodiments, neutral macrophages are added to a bio-ink admixture that contains cells that produce the necessary cytokines for M2-activation of the macrophages. In some embodiments, mixtures of macrophages and MSCs are combined in bio-ink admixtures of cells. In some embodiments, parenchymal support cells such as, but not limited to, fibroblasts, are added to the bio-ink admixtures to enhance the structural properties of the bio-ink. As used herein, "I-bio-ink" means a bio-ink admixture that contains some proportion of immunomodulatory cells as described herein, in addition to the possible, but not mandatory presence of non-immunomodulatory cells and/or biomaterial support. In some embodiments, I-bio-ink comprises (1) parenchymal cells; and (2) MSCs, macrophages, or a combination thereof. In some embodiments, I-bio-ink comprises (1) parenchymal cells; (2) MSCs, macrophages, or a combination thereof; and (3) biomaterial support, wherein the biomaterial support is one or more extrusion compounds as defined herein. In some embodiments, the biomaterial support is a hydrogel.

Cell Culture Media

In some embodiments, the bio-ink comprises a cell culture medium. The cell culture medium is any suitable medium. In various embodiments, suitable cell culture media include, by way of non-limiting examples, Dulbecco's Phosphate Buffered Saline, Earle's Balanced Salts, Hanks' Balanced Salts, Tyrode's Salts, Alsever's Solution, Gey's Balanced Salt Solution, Kreb's-Henseleit Buffer Modified, Kreb's-Ringer Bicarbonate Buffer, Puck's Saline, Dulbecco's Modified Eagle's Medium, Dulbecco's Modified Eagle's Medium/Nutrient F-12 Ham, Nutrient Mixture F-10 Ham (Ham's F-10), Medium 199, Minimum Essential Medium Eagle, RPMI-1640 Medium, Ames' Media, BGJb Medium (Fitton-Jackson Modification), Click's Medium, CMRL-1066 Medium, Fischer's Medium, Glasgow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, William's Medium E, or combinations thereof. In some embodiments, the cell culture medium is modified or supplemented. In some embodiments, the cell culture medium further comprises albumin, selenium, transferrins, fetuins, sugars, amino acids, vitamins, growth factors, cytokines, hormones, antibiotics, lipids, lipid carriers, cyclodextrins, or a combination thereof.

Extracellular Matrix

In some embodiments, the bio-ink further comprises one or more components of an extracellular matrix or derivatives thereof. In some embodiments, "extracellular matrix" includes proteins that are produced by cells and transported out of the cells into the extracellular space, where they may serve as a support to hold tissues together, to provide tensile strength, and/or to facilitate cell signaling. Examples, of extracellular matrix components include, but are not limited to, collagen, fibronectin, laminin, hyaluronates, elastin, and proteoglycans. For example, multicellular aggregates optionally contain various ECM proteins (e.g., gelatin, fibrinogen, fibrin, collagen, fibronectin, laminin, elastin, and/or proteoglycans). The ECM components or derivatives of ECM components can be added to the cell paste used to form the multicellular aggregate. The ECM components or derivatives of ECM components added to the cell paste can be purified from a human or animal source, or produced by recombinant methods known in the art. Alternatively, the ECM components or derivatives of ECM components can be naturally secreted by the cells in the elongate cellular body, or the cells used to make the elongate cellular body can be genetically manipulated by any suitable method known in the art to vary the expression level of one or more ECM components or derivatives of ECM components and/or one or more cell adhesion molecules or cell-substrate adhesion molecules (e.g., selectins, integrins, immunoglobulins, and adherins). The ECM components or derivatives of ECM components may promote cohesion of the cells in the multicellular aggregates. For example, gelatin and/or fibrinogen can suitably be added to the cell paste, which is used to form multicellular aggregates. The fibrinogen can then be converted to fibrin by the addition of thrombin.

In some embodiments, the bio-ink further comprises an agent that encourages cell adhesion.

In some embodiments, the bio-ink further comprises an agent that inhibits cell death (e.g., necrosis, apoptosis, or autophagocytosis). In some embodiments, the bio-ink further comprises an anti-apoptotic agent. Agents that inhibit cell death include, but are not limited to, small molecules, antibodies, peptides, peptibodies, or combination thereof. In some embodiments, the agent that inhibits cell death is selected from: anti-TNF agents, agents that inhibit the activity of an interleukin, agents that inhibit the activity of an interferon, agents that inhibit the activity of an GCSF (granulocyte colony-stimulating factor), agents that inhibit the activity of a macrophage inflammatory protein, agents that inhibit the activity of TGF-B (transforming growth factor B), agents that inhibit the activity of an MMP (matrix metalloproteinase), agents that inhibit the activity of a caspase, agents that inhibit the activity of the MAPK/JNK signaling cascade, agents that inhibit the activity of a Src kinase, agents that inhibit the activity of a JAK (Janus kinase), or a combination thereof. In some embodiments, the bio-ink comprises an anti-oxidant.

Extrusion Compounds

In some embodiments, the bio-ink further comprises an extrusion compound (i.e., a compound that modifies the extrusion properties of the bio-ink). Examples of extrusion compounds include, but are not limited to gels, hydrogels (including UV cross-linkable and thermoreversible hydrogels described herein), surfactant polyols (e.g., Pluronic F-127 or PF-127), thermo-responsive polymers, hyaluronates, alginates, extracellular matrix components (and derivatives thereof), collagens, other biocompatible natural or synthetic polymers, nanofibers, and self-assembling nanofibers.

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

Suitable hydrogels include those derived from collagen, hyaluronate, fibrin, alginate, agarose, chitosan, and combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, the support material is selected from: hydrogel, NovoGel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof.

UV Cross-Linkable Hydrogels

Suitable hydrogels include methacrylated hydrogels, such as Polyethylene (glycol) diacrylate-based (PEG-DA) hydrogels, which are used in cell biology due to their ability to cross-link in presence of UV light and due to their inertness to cells. PEG-DA is commonly used as scaffold in tissue engineering since polymerization occurs rapidly at room temperature and requires low energy input, has high water content, is elastic, and can be customized to include a variety of biological molecules.

Photoinitiators

In some embodiments, an extrusion compound comprises a photoinitiator, which is a molecule that upon absorption of light at a specific wavelength produces reactive species capable of catalyzing polymerization or polycondensation reactions. These reactions area also called photopolymerization or radiation curing. Photoinitiators are typically ketones which contain both aromatic and carbonyl groups.

There are two types of photoinitiators: cationic and radical photoinitiators. Radical photoinitiators are water-compatible and act on molecules containing an acrylate or styrene group. The range of wavelengths used is typically near UV (300 nm-400 nm) but recent progress in initiator chemistry is expanding the ranges of wavelengths that can be used. Photoinitiators used in biology such as Irgacure 2959, 184, and 651 fall into this class.

A suitable photoinitiator for use with the bio-inks and/or support materials described herein is Irgacure 2959 (4-(2-hydroxyethoxy)phenyl-(2-propyl) ketone (Glycosan BioSystems, Inc.; Salt Lake City, Utah) due to its high solubility in water and its minimal toxicity compared to other Irgacure species. Upon absorption of UV light, Irgacure 2959 dissociates into 2 primary radicals which then react with the vinyl (C=C) groups of PEG-DA to initiate polymerization. There are three phases in photopolymerization: photoinitiation, propagation, and termination. Rate of reaction during the first step is dependent on the nature of the photoinitiator (quantum yield, photoinitiator efficiency) and intensity of light while the later steps (propagation and termination) are a function of vinyl bond concentration and the rate constants for propagation and termination.

Thermoreversible Gels

In some embodiments, hydrogel-based extrusion compounds are thermoreversible gels (also known as thermoresponsive gels or thermogels). In some embodiments, a suitable thermoreversible hydrogel is not a liquid at room temperature. In specific embodiments, the gelation temperature (Tgel) of a suitable hydrogel is about 10° C., about 15° C., about 20° C., about 25° C., about 30° C., about 35° C., and about 40° C., including increments therein. In certain embodiments, the Tgel of a suitable hydrogel is about 10° C. to about 25° C. In some embodiments, the bio-ink (e.g., comprising hydrogel, one or more cell types, and other additives, etc.) described herein is not a liquid at room temperature. In specific embodiments, the gelation temperature (Tgel) of a bio-ink described herein is about 10° C., about 15° C., about 20° C., about 25° C., about 30° C., about 35° C., and about 40° C., including increments therein. In certain embodiments, the Tgel of a bio-ink described herein is about 10° C. to about 25° C.

Polymers composed of polyoxypropylene and polyoxyethylene form thermoreversible gels when incorporated into aqueous solutions. These polymers have the ability to change from the liquid state to the gel state at temperatures that can be maintained in a bioprinter apparatus. The liquid state-to-gel state phase transition is dependent on the polymer concentration and the ingredients in the solution.

Poloxamer 407 (Pluronic F-127 or PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. It is one of the series of poloxamer ABA block copolymers. PF-127 has good solubilizing capacity, low toxicity and is, therefore, considered a suitable extrusion compound.

In some embodiments, the viscosity of the hydrogels and bio-inks presented herein is measured by any means described. For example, in some embodiments, an LVDV-II+ CP Cone Plate Viscometer and a Cone Spindle CPE-40 is used to calculate the viscosity of the hydrogels and bio-inks. In other embodiments, a Brookfield (spindle and cup) viscometer is used to calculate the viscosity of the hydrogels and bio-inks. In some embodiments, the viscosity ranges referred to herein are measured at room temperature. In other embodiments, the viscosity ranges referred to herein are measured at body temperature (e.g., at the average body temperature of a healthy human).

In further embodiments, the hydrogels and/or bio-inks are characterized by having a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise.

In some embodiments, the bio-ink comprises cells and extrusion compounds suitable for continuous bioprinting. In specific embodiments, the bio-ink has a viscosity of about 1500 mPa·s. A mixture of Pluronic F-127 and cellular material may be suitable for continuous bioprinting. Such a bio-ink is optionally prepared by dissolving Pluronic F-127 powder by continuous mixing in cold (4° C.) phosphate buffered saline (PBS) over 48 hours to 30% (w/v). Pluronic F-127 may also be dissolved in water. Cells are cultivated and expanded using standard sterile cell culture techniques. The cells may be pelleted at 200 g for example, and re-suspended in the 30% Pluronic F-127 and aspirated into a reservoir affixed to a bioprinter where it can be allowed to solidify at a gelation temperature from about 10 to about 25° C. Gelation of the bio-ink prior to bioprinting is optional. The bio-ink, including bio-ink comprising Pluronic F-127 can be dispensed as a liquid.

In various embodiments, the concentration of Pluronic F-127 can be any value with suitable viscosity and/or cytotoxicity properties. A suitable concentration of Pluronic F-127 may also be able to support weight while retaining its shape when bioprinted. In some embodiments, the concentration of Pluronic F-127 is about 10%, about 15%, about 20%, about 25%, about 30%, about 35%, about 40%, about 45%, or about 50%. In some embodiments, the concentration of Pluronic F-127 is between about 30% and about 40%, or between about 30% and about 35%.

Figure 6:
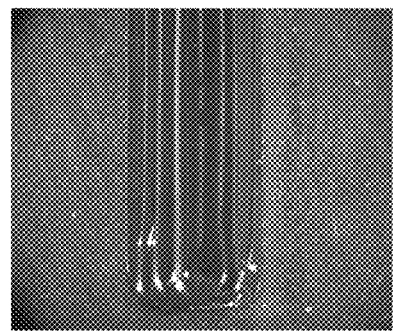
FIG. 6 illustrates a non-limiting example of a three-dimensional construct generated by continuous deposition of PF-127 using a NovoGen MMX™ bioprinter connected to a syringe with a 510 µm needle; in this case, a pyramid-shaped construct.

Referring to FIG. 6, in a particular embodiment, a three-dimensional, pyramid-shaped construct is generated by continuous deposition of PF-127 using a NovoGen MMX™ bioprinter connected to a syringe with a 510 μm needle.

Figure 7:
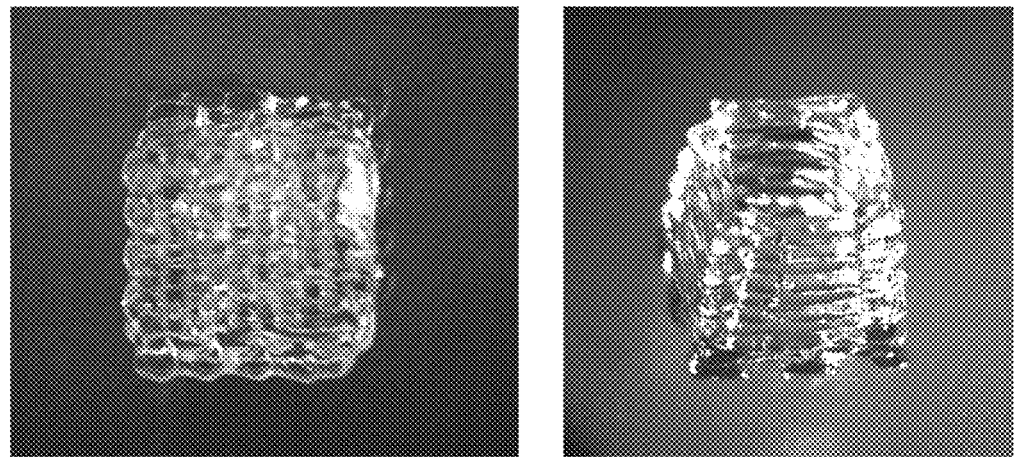
FIG. 7 illustrates a non-limiting example of a three-dimensional construct generated by continuous deposition of PF-127 using a NovoGen MMX™ bioprinter connected to a syringe with a 510 µm needle; in this case, cube-shaped (left) and hollow cube-shaped (right) constructs.

Referring to FIG. 7, in a particular embodiment, a three-dimensional, cube-shaped (left) and hollow cube-shaped (right) constructs generated by continuous deposition of PF-127 using a NovoGen MMX™ bioprinter connected to a syringe with a 510 µm needle.

In some embodiments, the non-cellular components of the bio-ink (e.g., extrusion compounds, etc.) are removed prior to use. In further embodiments, the non-cellular components are, for example, hydrogels, surfactant polyols, thermo-responsive polymers, hyaluronates, alginates, collagens, or other biocompatible natural or synthetic polymers. In still further embodiments, the non-cellular components are removed by physical, chemical, or enzymatic means. In some embodiments, a proportion of the non-cellular components remain associated with the cellular components at the time of use.

In some embodiments, the cells are pre-treated to increase cellular interaction. For example, cells are optionally incubated inside a centrifuge tube after centrifugation in order to enhance cell-cell interactions prior to shaping the bio-ink.

Support Material

Disclosed herein, in certain embodiments, are devices, systems, and methods for fabricating tissues and organs. In some embodiments, the devices comprise one or more printer heads for receiving and holding at least one cartridge that optionally contains support material. In some embodiments, the methods comprise the use of support material. In further embodiments, the tissues and organs fabricated by use of the devices, systems, and methods described herein comprise support material at the time of fabrication or thereafter.

In some embodiments, the support material is capable of excluding cells growing or migrating into or adhering to it. In some embodiments, the support material is permeable for nutrient media.

In some embodiments, the viscosity of the support material is changeable. In some embodiments, the viscosity of the support material is changed by modifying the temperature of the support material. In some embodiments, the viscosity of the support material is changed by modifying the pressure of the support material. In some embodiments, the viscosity of the support material is changed by modifying the concentration of the support material. In some embodiments, the viscosity of the support material is changed by cross-linking (e.g., by use of a chemical cross-linker), or photocrosslinking (e.g., using ultraviolet light exposure).

In some embodiments, the permeability of the support material is changeable. In some embodiments, the permeability of the support material is modified by varying the temperature of the support material or the temperature surrounding the support material. In some embodiments, the permeability of the support material is modified by contacting the support material with an agent that modifies permeability.

In some embodiments, the compliance (i.e., elasticity or hardness) of the support material is modified. In some embodiments, the compliance of the support material is modified by varying the temperature of the support material or the temperature surrounding the support material. In some embodiments, the compliance of the support material is modified by contacting the support material with an agent that modifies compliance.

Many support materials are suitable for use in the methods described herein. In some embodiments, hydrogels (including UV cross-linkable and thermoreversible hydrogels described herein) are exemplary support materials possessing one or more advantageous properties including: non-adherent, biocompatible, extrudable, bioprintable, non-cellular, and of suitable strength. In some embodiments, suitable hydrogels are natural polymers. In one embodiment, the confinement material is comprised of NovoGel™. In further embodiments, suitable hydrogels include those derived from surfactant polyols (e.g., Pluronic F-127), collagen, hyaluronate, fibrin, alginate, agarose, chitosan, derivatives or combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, the confinement material is selected from: hydrogel, NovoGel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof.

In some embodiments, the support material contains cells prior to being present in the bioprinter. In some embodiments, the support material is a hydrogel containing a suspension of cells. In some embodiments, the support material is a hydrogel containing a mixture of more than one cell type.

Exemplary Uses of Support Materials

In some embodiments, the support material is used as building units for constructing a biological construct (e.g., cellular construct, tissue, organ, etc.). In further embodiments, the support material unit is used to define and maintain the domains void of cellular material (i.e., the intermediate cellular units) of a desired construct. In some embodiments, the support material is capable of assuming any shape or size.

For example, according to one embodiment, NovoGel™ solution (originally in powder phase mixed with buffer and water) may be heated to reduce its viscosity and taken up in a micropipette with a desired dimension (or in a chamber of a desired shape by negative displacement of a piston). The NovoGel™ solution in the pipette (or the chamber) may be cooled to room temperature, for example by forced air on the exterior of the pipette (or the chamber) or plunging the micropipette into a container with cold liquid, so that it can solidify into a gel with the desired shape, i.e., a support material. The resulting support material is optionally dispensed from the pipette or chamber during the construction of a particular cellular construct, tissue, or organ. See e.g., FIG. 5.

In some embodiments, the support material is used for increasing the viability of the engineered tissue or organ after bioprinting. In further embodiments, support material provides direct contact between the tissue or organ and a nutrient medium through a temporary or semi-permanent lattice of confinement material (e.g., support material). In some embodiments, the tissue is constrained in a porous or gapped material. Direct access of at least some of the cells of the tissue or organ to nutrients increases the viability of the tissue or organ.

In further embodiments, the methods disclosed herein comprise additional and optional steps for increasing the viability of an engineered tissue or organ including: 1) optionally dispensing base layer of confinement material (e.g., support material) prior to placing cohered multicellular aggregates; 2) optionally dispensing a perimeter of confinement material; 3) bioprinting cells of the tissue within a defined geometry; and 4) dispensing elongate bodies (e.g., cylinders, ribbons, etc.) of confinement material overlaying the nascent tissue in a pattern that introduces gaps in the confinement material, such as a lattice, mesh, or grid.

In some embodiments, the gaps overlaying pattern are distributed uniformly or substantially uniformly around the surface of the tissue or organ. In other embodiments, the gaps are distributed non-uniformly, whereby the cells of the tissue or organ are exposed to nutrients non-uniformly. In non-uniform embodiments, the differential access to nutrients is optionally exploited to influence one or more properties of the tissue or organ. For instance, it may be desirable to have cells on one surface of a bioprinted, cellular construct, tissue, or organ proliferate faster than cells on another surface. In some embodiments, the exposure of various parts of the tissue or organ to nutrients can be changed at various times to influence the development of the tissue or organ toward a desired endpoint.

In some embodiments, the confinement material is removed at any suitable time, including but not limited to, immediately after bioprinting (e.g., within 10 minutes), after bioprinting (e.g., after 10 minutes), before the cells are substantially cohered to each other, after the cells are substantially cohered to each other, before the cells produce an extracellular matrix, after the cells produce an extracellular matrix, just prior to use, and the like. In various embodiments, confinement material is removed by any suitable method. For example, in some embodiments, the confinement material is excised, pulled off the cells, digested, or dissolved.

Methods and Systems for Calibrating the Position of a Bioprinter Cartridge

Disclosed herein, in certain embodiments, are bioprinters for fabricating tissues and organs. In some embodiments, a cartridge attached to the bioprinter comprises a bio-ink and/or a support material. In some embodiments, the bioprinter deposits the bio-ink or support material in a specific pattern and at specific positions in order to form a specific tissue construct. In some embodiments, a cartridge comprising bio-ink is disposable. In some embodiments, the cartridge is ejected from the bioprinter following extrusion, dispensing, or deposition of the contents. In some embodiments, a new cartridge is attached to the bioprinter.

In order to fabricate complex structures, the bioprinters disclosed herein dispense bio-ink and/or support material from a cartridge with a suitable repeatable accuracy. In various embodiments, suitable repeatable accuracies include those of about ±5, 10, 20, 30, 40, or 50 μm on any axis. In some embodiments, the bioprinters disclosed herein dispense bio-ink and/or support material from a cartridge with a repeatable accuracy of about ±20 μm. However, in some embodiments, due to the removal and insertion of cartridges, the position of the printer head (and thus the cartridges) with respect to the tissue construct varies. Thus, there is a need for a method of precisely calibrating the position of the printer head, cartridge, and dispensing orifice with respect to the printer stage, receiving surface, tissue, or organ.

In some embodiments, the method of calibrating the position of a printer head comprises use of at least one laser. In further embodiments, the method of calibrating the position of a printer head comprises use of a first and second laser. In still further embodiments, the method of calibrating the position of a printer head comprises use of a first and second laser and one or more cameras. In some embodiments, the method of calibrating the position of a printer head comprises at least one laser and at least one camera. In some embodiments, the method of calibrating the position of a printer head comprises at least camera.

In some embodiments, the method of calibrating the position of a printer head comprises manual (e.g., visual) calibration.

In some embodiments, the method of calibrating the position of a printer head comprises image-based calibration. In some embodiments, the method of calibrating the position of a printer head comprises one or more cameras.

In some embodiments, the method of calibrating the position of a printer head comprises manual calibration and laser calibration. In some embodiments, the method of calibrating the position of a printer head comprises manual calibration, image-based calibration, and laser calibration.

In some embodiments, the position of the printer head is calibrated along one axis, wherein the axis is selected from the x-axis, the y-axis, and the z-axis. In some embodiments, the position of the printer head is calibrated along two axes, wherein the axes are selected from the x-axis, the y-axis, and the z-axis. In some embodiments, the position of the printer head is calibrated along three axes, wherein the axes are selected from the x-axis, the y-axis, and the z-axis.

In some embodiments, calibration is made by use of at least one laser. In further embodiments, calibration is made by use of a first and a second laser. In still further embodiments, calibration is made by use of a first and a second laser and one or more cameras. In some embodiments, calibration is made by use of at least one camera.

Method for Calibrating Using a Horizontal Laser

Disclosed herein, in certain embodiments, are methods of calibrating the position of a printer head comprising a dispensing orifice. In some embodiments, a method disclosed herein further comprises activating a laser and generating at least one substantially stable and/or substantially stationary laser beam, and where said laser beam is horizontal to the ground. See, e.g., FIG. 1.

In some embodiments, the methods comprise, calibrating the position of a printer head along at least one axis, wherein the axis is selected from the x-axis, y-axis, and z-axis. In some embodiments, the methods comprise calibrating the position of the printer head along at least two axes, wherein the axis is selected from the x-axis, y-axis, and z-axis. In some embodiments, the methods comprise calibrating the position of the printer head along at least three axes, wherein the axis is selected from the x-axis, y-axis, and z-axis. In some embodiments, the methods comprise (a) calibrating the position of the printer head along the y-axis; (b) calibrating the position of the printer head along the x-axis; and/or (c) calibrating the position of the printer head along the z-axis; wherein each axis corresponds to the axis of the same name in the Cartesian coordinate system. In some embodiments, calibration is made by use of at least one laser. In some embodiments, calibration is made by use of a first and a second laser. In some embodiments, calibration is made by the additional use of at least one camera.

In some embodiments, calibrating the position of a printer head along the y-axis comprises: (a) positioning the printer head so that the printer head is (i) located in a first y octant and (ii) the dispensing orifice is below the upper threshold of the laser beam; (b) moving the printer head towards the laser beam and stopping said movement as soon as the laser beam is interrupted by the printer head, wherein the position at which the laser beam is interrupted by the printer head is the first y position; (c) re-positioning the printer head so that the printer head is located in the second y octant and the dispensing orifice is below the upper threshold of the laser beam; (d) moving the printer head towards the laser beam and stopping said movement as soon as the laser beam is interrupted by the printer head, wherein the position at which the laser beam is interrupted is the second y position; (e) and calculating the mid-point between the first y position and the second y position.

In some embodiments, calibrating the position of a printer head along the x-axis comprises: (a) positioning the printer head (i) at the mid-point between the first y position and the second y position, and (ii) outside the sensor threshold of the laser; and (b) moving the printer head towards the sensor threshold and stopping said movement as soon as the printer head contacts the sensor threshold; wherein the position at which the printer head contacts the sensor increased by half the printer head width is the x position.

In some embodiments, calibrating the position of a printer head along the y-axis comprises: (a) positioning the printer head so that the laser beam can measure the precise location of one side of the printer head; (b) positioning the printer head so that the laser beam can measure the precise location of the opposing side of the printer head; (c) and calculating the midpoint location of the printer head to be relative to the laser location during each measurement and the measured distances.

In some embodiments, calibrating the position of a printer head along the x-axis comprises: (a) positioning the printer head so that the laser beam can measure the precise location of one side of the printer head; (b) positioning the printer head so that the laser beam can measure the precise location of the opposing side of the printer head; (c) and calculating the midpoint location of the printer head to be relative to the laser location during each measurement and the measured distances.

In some embodiments, calibrating the position of a printer head along the z-axis comprises: (a) positioning the printer head so that the dispensing orifice is located above the laser beam; and (b) moving the printer head towards the laser beam and stopping said movement as soon as the laser beam is interrupted by the printer head, wherein the position at which the laser beam is interrupted is the z position.

Method for Calibrating Using a Vertical Laser

Disclosed herein, in certain embodiments, are methods of calibrating the position of a printer head comprising a dispensing orifice. In some embodiments, a method disclosed herein further comprises activating the laser and generating at least one substantially stable and/or substantially stationary laser beam, and where said laser beam is vertical to the ground. See, e.g., FIG. 2. In some embodiments, a method disclosed herein further comprises the use of at least one camera.

In some embodiments, the methods comprise, calibrating the position of a printer head along at least one axis, wherein the axis is selected from the x-axis, y-axis, and z-axis. In some embodiments, the methods comprise calibrating the position of a printer head along at least two axes, wherein the axis is selected from the x-axis, y-axis, and z-axis. In some embodiments, the methods comprise calibrating the position of a printer head along at least three axes, wherein the axis is selected from the x-axis, y-axis, and z-axis.

In some embodiments, the methods comprise (a) calibrating the position of the printer head along the y-axis; (b) calibrating the position of the printer head along the x-axis; and (c) calibrating the position of the printer head along the z-axis; wherein each axis corresponds to the axis of the same name in the Cartesian coordinate system.

In some embodiments, calibrating the position of a printer head along the y-axis comprises: (a) positioning the printer head so that the printer head is (i) located in a first y octant and (ii) the dispensing orifice is outside the sensor threshold of the laser; (b) moving the printer head towards the laser beam and stopping said movement as soon as the laser beam is interrupted by the printer head, wherein the position at which the laser beam is interrupted by the printer head is the first y position; (c) re-positioning the printer head so that the printer head is located in the second y octant and the dispensing orifice is outside the sensor threshold of the laser; (d) moving the printer head towards the laser beam and stopping said movement as soon as the laser beam is interrupted by the printer head, wherein the position at which the laser beam is interrupted is the second y position; (e) and calculating the mid-point between the first y position and the second y position.

In some embodiments, calibrating the position of a printer head along the x-axis comprises: (a) positioning the printer head (i) at the mid-point between the first y position and the second y position, and (ii) outside the sensor threshold of the laser; and (b) moving the printer head towards the sensor threshold and stopping said movement as soon as the printer head contacts the sensor threshold; wherein the position at which the printer head contacts the sensor increased by half the printer head width is the x position.

In some embodiments, calibrating the position of a printer head along the z-axis comprises: (a) positioning the printer head so that the dispensing orifice is located above the laser beam so that it is just outside of the laser sensor range threshold; and (b) lowering the printer head until the sensor threshold is reached, wherein the position at which the laser sensor threshold is reached is the z position. In some embodiments, steps (a) and (b) are repeated at multiple points of the printer head and measured heights are averaged to determine the z position.

In some embodiments, calibrating the position of a printer head along the z-axis comprises: (a) positioning the printer head so that the laser beam can measure the precise location of one or more points on the bottom of the printer head; (b) calculating the absolute or average location of the printer head based on the laser position and known measured distance.

Method for Calibrating Using a Vertical and Horizontal Laser

Disclosed herein, in certain embodiments, are methods of calibrating the position of a printer head comprising a dispensing orifice, wherein the printer head is attached to a bioprinter, comprising calibrating the position of the printer head along at least one axis, wherein the axis is selected from the x-axis, y-axis, and z-axis. In some embodiments, the method comprises calibrating the position of a printer head along at least two axes, wherein the axis is selected from the x-axis, y-axis, and z-axis. In some embodiments, the method comprises calibrating the position of a printer head along at least three axes, wherein the axis is selected from the x-axis, y-axis, and z-axis.

In some embodiments, the methods comprise (a) calibrating the position of the printer head along the y-axis; (b) calibrating the position of the printer head along the x-axis; and (c) calibrating the position of the printer head along the z-axis; wherein each axis corresponds to the axis of the same name in the Cartesian coordinate system.

In some embodiments, calibration comprises use of a first laser and a second laser. In some embodiments, the first laser is a vertical laser and the second laser is a horizontal laser. In some embodiments, calibration further comprises use of at least one camera.

System for Calibrating Using a Laser

Disclosed herein, in certain embodiments, are systems for calibrating the position of a cartridge comprising a deposition orifice, wherein the cartridge is attached to a bioprinter, said system comprising: a means for calibrating the position of the cartridge along at least one axis, wherein the axis is selected from the y-axis, x-axis, and z-axis.

Also disclosed herein, in certain embodiments, are systems for calibrating the position of a printer head comprising a dispensing orifice, wherein the printer head is attached to a bioprinter, said system comprising: a means for calibrating the position of the printer head along an x-axis; a means for calibrating the position of the printer head along a y-axis; and a means for calibrating the position of the printer head along a z-axis.

In some embodiments, a system for calibrating the position of a printer head comprises a means for calibrating the printer head along the x-axis, y-axis, and z-axis. In some embodiments, the means for calibrating a printer head along the x-axis, y-axis, and z-axis is laser alignment, optical alignment, mechanical alignment, piezoelectric alignment, magnetic alignment, electrical field or capacitance alignment, ultrasound alignment, image-based alignment, or a combination thereof.

In some embodiments, a system for calibrating the position of a printer head comprises a means for calibrating the printer head along the x-axis, y-axis, and z-axis. In some embodiments, the means for calibrating a printer head along the x-axis, y-axis, and z-axis is laser alignment. In some embodiments, the laser alignment means comprises at least one laser. In some embodiments, the laser alignment means comprises a plurality of lasers. In some embodiments, the system for calibrating the position of a printer head further comprises an additional means for calibrating the printer head along the x-axis, y-axis, and z-axis. In some embodiments, the means for calibrating the printer head along the x-axis, y-axis, and z-axis is image-based alignment using at least one camera.

In some embodiments, the laser alignment means it has any suitable accuracy. In various embodiments, suitable accuracies include those of about ±5, 10, 20, 30, 40, or 50 μm on any axis. In some embodiments, the laser alignment means is accurate to ±40 μm on the vertical axis and ±20 μm on the horizontal axis.

In some embodiments, the laser path is uninterrupted between the laser source and the measurement point. In some embodiments, the laser path is altered by up to 179° by use of a reflective surface or optical lens. In some embodiments, the laser path is altered by 90°. In some embodiments, a horizontal laser beam is used to measure in a vertical path by deflection using a reflective surface. In some embodiments, a vertical laser beam is used to measure in a horizontal path by deflection using a reflective surface.

Three-Dimensional Calibration System for Full Automation

Disclosed herein, in certain embodiments, are bioprinters comprising the means to automatically determine the x, y, z coordinates of the deposition orifice and the print target surface before and during the bioprinting process. The automatic three-dimensional determination of such coordinates both before and during the bioprinting process ensures that biomaterials are printed at the target surface at the proper positions and using the optimum dispensing orifice to target surface separation distance. The frequent replacement of deposition orifices and receiving surfaces prior to a bioprinting job necessitates the accurate determination of the positioning of these two elements before initiation of bioprinting in order to control and maximize bioprinting quality. Determination of the positions of the deposition orifice and the printing target surface during the bioprinting process enables dynamic mapping of the target surface. Such positional determination during the bioprinting process is important as the surface height may not be as uniform as required due to product tolerances or shrinkage of the surface material and the surface height is continuously changing as layer upon layer of bio-ink is deposited onto the surface. Moreover, dynamic measurement of the thickness of each track of deposited bio-ink is optionally used as feedback to adjust bioprinting parameters such as deposition rate, dispensing orifice/receiving surface relative travel speed and print height (distance between the deposition orifice and print target surface). The three-dimensional positional determination optionally allows for printer deposition error checking, plate positioning error checking, monitoring for structural changes such as construct shrinkage during or after a bioprinting job, automated well center determination for transwell and microtiter plates, and automated quality control monitoring, especially with the incorporation digital camera technology.

Disclosed herein, in certain embodiments, are three-dimensional calibration systems for an automated bioprinter comprising a sensor fixed to a receiving surface of the bioprinter for determining the position of a deposition orifice of the bioprinter; and a sensor fixed to a printer head of the bioprinter for determining the position of a print target surface associated with the receiving surface; whereby the system calculates a print height, the print height comprising the distance between the deposition orifice and a print target surface. In some embodiments, a three-dimensional calibration system comprises at least two lasers, a sensor fixed to the receiving surface for determining the position of a deposition orifice; and a sensor fixed to the printer head for determining the position of the receiving surface; whereby the system calculates a print height, the print height comprising the distance between the deposition orifice and receiving surface.

In some embodiments, the sensors are selected from: triangulation sensors, ultrasonic distance sensing probes, and digital cameras.

In some embodiments, the calibration system has any suitable accuracy. In various embodiments, suitable accuracies include those of about ±5, 10, 20, 30, 40, or 50 μm on any axis.

Figure 4:
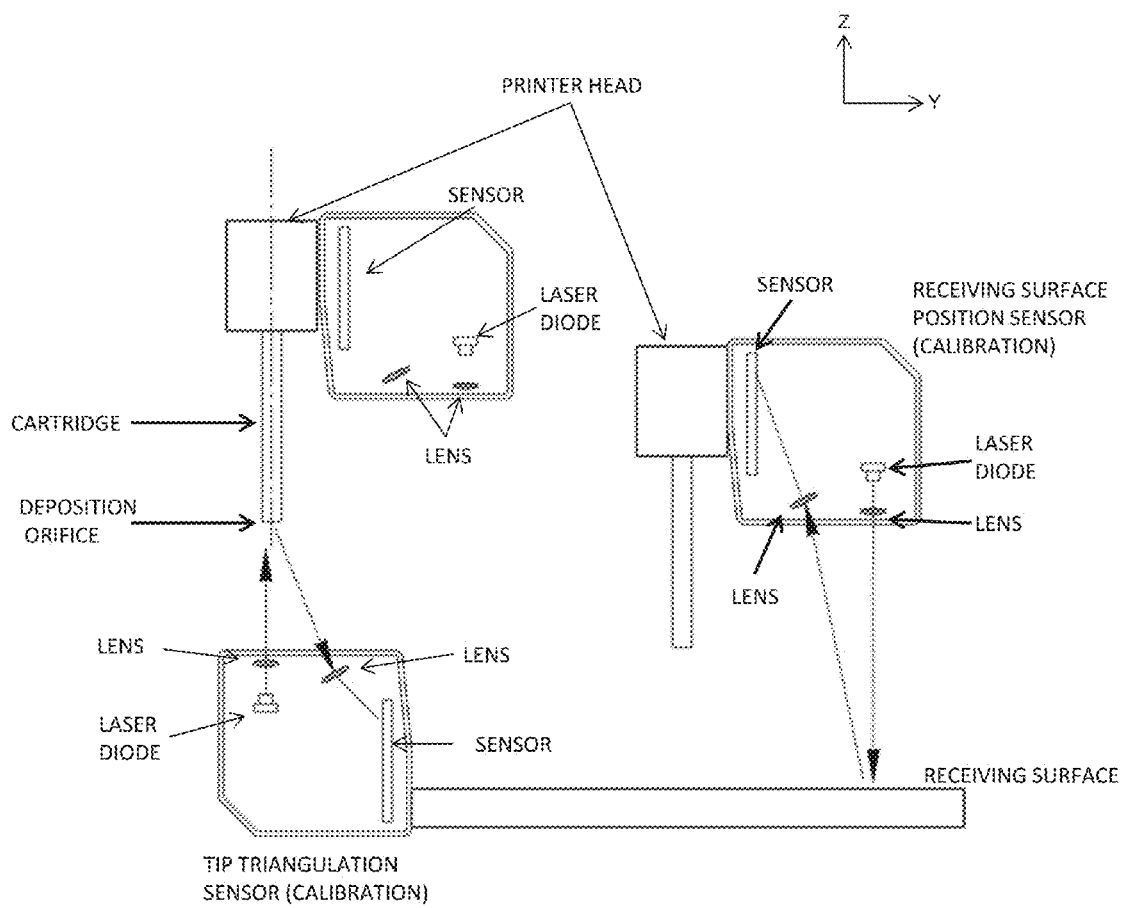
FIG. 4 illustrates a non-limiting schematic example of a fully automated calibration configuration with dual sensors; in this case, a schematic depicting a tip triangulation sensor mounted to a print surface and a surface distance sensor mounted to a pump head, wherein information from the two sensors is used to automate a bioprinting process.

Referring to FIG. 4, in a particular embodiment, a three-dimensional calibration system with triangulation sensors is depicted. The left-hand side of FIG. 4 shows a printer head with attached capillary held above the tip sensing triangulation sensor. The relative position of the capillary tip (deposition orifice) and the sensor beam is varied in order to produce a distance vs. position data file from which both the capillary center X,Y coordinate and the average tip height can be determined automatically. The right-hand side of FIG. 4 shows the print head at a later time with attached capillary held above the target print surface. The relative position of the surface sensing triangulation sensor beam and the target printing surface is varied in order to produce a distance vs. position data file from which a surface map of the print surface can be constructed. The information obtained from these two sensors can be combined and used to automate the bioprinting process, with the deposition of materials occurring with the optimum separation between the deposition orifice and target printing surface. This separation can be adjusted to correct for surface height changes throughout the bioprinting process using the information recorded as described above.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent.

Example 1

HASMC-HAEC Mixed Cellular Cylinders

Cell Culture

Smooth Muscle Cells:

Primary human aortic smooth muscle cells (HASMC) were maintained and expanded in low glucose Dulbecco's modified eagle medium (DMEM; Invitrogen Corp., Carlsbad, Calif.) supplemented with 10% fetal bovine serum (FBS), 100 U/ml Penicillin, 0.1 mg/ml streptomycin, 0.25 µg/ml of amphotericin B, 0.01M of HEPES (all from Invitrogen Corp., Carlsbad, Calif.), 50 mg/L of proline, 50 mg/L of glycine, 20 mg/L of alanine, 50 mg/L of ascorbic acid, and 3 µg/L of $CuSO_4$ (all from Sigma, St. Louis, Mo.) at 37° C. and 5% $CO_2$. Confluent cultures of HASMCs between passage 4 and 8 were used in all studies.

Endothelial Cells:

Primary human aortic endothelial cells (HAEC) were maintained and expanded in Medium 200 supplemented with 2% FBS, 1 µg/ml of hydrocortisone, 10 ng/ml of human epidermal growth factor, 3 ng/ml of basic fibroblast growth factor, 10 µg/ml of heparin, 100 U/ml Penicillin, 0.1 mg/ml streptomycin, and 0.25 µg/ml of amphotericin B (all from Invitrogen Corp., Carlsbad, Calif.). The cells were grown on gelatin (from porcine serum; Sigma, St. Louis, Mo.) coated tissue culture treated flasks at 37° C. and 5% $CO_2$. Confluent cultures of HAEC's between passage 4 and 8 were used in all studies.

NovoGel™ Mold

Preparation of 2% w/v NovoGel™ Solution:

1 g of low melting point NovoGel™ was dissolved in 50 ml of Dulbecco's phosphate buffered saline (DPBS). Briefly, the DPBS and NovoGel™ were heated to 85° C. on a hot plate with constant stirring until the NovoGel™ dissolved completely. NovoGel™ solution was sterilized by steam sterilization at 125° C. for 25 minutes. The NovoGel™ solution remained in liquid phase as long as the temperature is maintained above 66.5° C. Below this temperature a phase transition occurs, the viscosity of the NovoGel™ solution increases and the NovoGel™ forms a solid gel.

Preparation of NovoGel™ Mold:

A NovoGel™ mold was fabricated for the incubation of cellular cylinders using a Teflon® mold that fits a 10 cm Petri dish. Briefly, the Teflon® mold was pre-sterilized using 70% ethanol solution and subjecting the mold to UV light for 45 minutes. The sterilized mold was placed on top of the 10 cm Petri dish (VWR International LLC, West Chester, Pa.) and securely attached. This assembly (Teflon® mold+Petri dish) was maintained vertically and 45 ml of pre-warmed, sterile 2% NovoGel™ solution was poured in the space between the Teflon® mold and the Petri dish. The assembly was then placed horizontally at room temperature for 1 hour to allow complete gelation of the NovoGel™. After gelation, the Teflon® print was removed and the NovoGel™ mold was washed twice using DPBS. 17.5 ml of HASMC culture medium was then added to the NovoGel™ mold.

HASMC-HAEC Cylinders

Fabrication of HASMC-HAEC Mixed Cellular Cylinders:

To prepare mixed cellular cylinders HASMC and HAEC were individually collected and then mixed at pre-determined ratios. Briefly, the culture medium was removed from confluent culture flasks and the cells were washed with DPBS (1 ml/5 $cm^2$ of growth area). Cells were detached from the surface of the culture flasks by incubation in the presence of trypsin (1 ml/15 $cm^2$ of growth area) for 10 minutes. HASMC were detached using 0.15% trypsin while HAEC were detached using 0.1% trypsin. Following the incubation appropriate culture medium was added to the flasks (2× volume with respect to trypsin volume). The cell suspension was centrifuged at 200 g for 6 minutes followed by complete removal of supernatant solution. Cell pellets were resuspended in respective culture medium and counted using a hemacytometer. Appropriate volumes of HASMC and HAEC were combined to yield mixed cell suspensions containing 5, 7.5, 10, 12.5, and 15% HAEC (as a % of total cell population). The mixed cell suspensions were centrifuged at 200 g for 5 minutes followed by complete removal of supernatant solution. Mixed cell pellets were resuspended in 6 ml of HASMC culture medium and transferred to 20 ml glass vials, followed by incubation on an orbital shaker at 150 rpm for 60 minutes, and at 37° C. and 5% $CO_2$. This allows the cells to aggregate with one another and initiate cell-cell adhesions. Post-incubation, the cell suspension was transferred to a 15 ml centrifuge tube and centrifuged at 200 g for 5 minutes. After removal of the supernatant medium, the cell pellet was resuspended in 400 µl of HASMC culture medium and pipetted up and down several times to ensure all cell clusters were broken. The cell suspension was transferred into a 0.5 ml microfuge tube placed inside a 15 ml centrifuge tube followed by centrifugation at 2000 g for 4 minutes to form a highly dense and compact cell pellet. The supernatant medium was aspirated and the cells were transferred into capillary tubes (OD 1.0 mm, ID 0.5 mm, L 75 mm; Drummond Scientific Co., Broomall, Pa.) by aspiration so as to yield cell cylinders 50 mm in length. The cell paste inside the capillaries was incubated in HASMC medium for 20 minutes at 37° C. and 5% $CO_2$. The cellular cylinders were then deposited from the capillary tubes into the grooves of the NovoGel™ mold (covered with HASMC medium) using the plunger supplied with the capillaries. The cellular cylinders were incubated for 24 and 48 hours at 37° C. and 5% $CO_2$.

Example 2

Multi-Layered Vascular Tubes

Cell Culture

Smooth Muscle Cells:

Primary human aortic smooth muscle cells (HASMC; GIBCO) were maintained and expanded in low glucose Dulbecco's modified eagle medium (DMEM) supplemented with 10% fetal bovine serum (FBS), 100 U/ml Penicillin, 0.1 mg/ml streptomycin, 0.25 µg/ml of amphotericin B, 0.01M of HEPES (all from Invitrogen Corp., Carlsbad, Calif.), 50 mg/L of proline, 50 mg/L of glycine, 20 mg/L of alanine, 50 mg/L of ascorbic acid, and 3 µg/L of $CuSO_4$ (all from Sigma, St. Louis, Mo.) at 37° C. and 5% $CO_2$. Confluent cultures of HASMC between passage 4 and 8 were used in all studies.

Endothelial Cells:

Primary human aortic endothelial cells (HAEC) were maintained and expanded in Medium 200 supplemented with 2% FBS, 1 µg/ml of hydrocortisone, 10 ng/ml of human epidermal growth factor, 3 ng/ml of basic fibroblast growth factor, 10 µg/ml of heparin, 100 U/ml Penicillin, 0.1 mg/ml streptomycin, and 0.25 µg/ml of amphotericin B (all from Invitrogen Corp., Carlsbad, Calif.). The cells were grown on gelatin (from porcine serum) coated tissue culture treated flasks at 37° C. and 5% $CO_2$. Confluent cultures of HAEC between passage 4 and 8 were used in all studies.

Fibroblasts:

Primary human dermal fibroblasts (HDF) were maintained and expanded in Medium 106 supplemented with 2% FBS, 1 µg/ml of hydrocortisone, 10 ng/ml of human epidermal growth factor, 3 ng/ml of basic fibroblast growth factor, 10 µg/ml of heparin, 100 U/ml Penicillin, and 0.1 mg/ml streptomycin (all from Invitrogen Corp., Carlsbad, Calif.) at 37° C. and 5% $CO_2$. Confluent cultures of HDF between passage 4 and 8 were used in all studies.

NovoGel™ Solutions and Mold

Preparation of 2% and 4% (w/v) NovoGel™ Solution:

1 g or 2 g (for 2% or 4% respectively) of low melting point NovoGel™ (Ultrapure LMP) was dissolved in 50 ml of Dulbecco's phosphate buffered saline (DPBS). Briefly, the DPBS and NovoGel™ were heated to 85° C. on a hot plate with constant stirring until the NovoGel™ dissolves completely. NovoGel™ solution was sterilized by steam sterilization at 125° C. for 25 minutes. The NovoGel™ solution remains in liquid phase as long as the temperature is maintained above 66.5° C. Below this temperature a phase transition occurs, the viscosity of the NovoGel™ solution increases and the NovoGel™ forms a solid gel.

Preparation of NovoGel™ Mold:

A NovoGel™ mold was fabricated for the incubation of cellular cylinders using a Teflon® mold that fit a 10 cm Petri dish. Briefly, the Teflon® mold was pre-sterilized using 70% ethanol solution and subjecting the mold to UV light for 45 minutes. The sterilized mold was placed on top of the 10 cm Petri dish and securely attached. This assembly (Teflon® mold+Petri dish) was maintained vertically and 45 ml of pre-warmed, sterile 2% NovoGel™ solution was poured in the space between the Teflon® mold and the Petri dish. The assembly was then placed horizontally at room temperature for 1 hour to allow complete gelation of the NovoGel™. After gelation, the Teflon® print was removed and the NovoGel™ mold was washed twice using DPBS. Then, either 17.5 ml of HASMC culture medium was added to the NovoGel™ mold for incubating HASMC-HAEC mixed cell cylinders or 17.5 ml of HDF culture medium is added to the NovoGel™ mold for incubating HDF cell cylinders.

Cellular Cylinders

Fabrication of HASMC-HAEC Mixed Cellular Cylinders:

To prepare mixed cellular cylinders HASMC and HAEC were individually collected and then mixed at pre-determined ratios. Briefly, the culture medium was removed from confluent culture flasks and the cells were washed with DPBS (1 ml/5 $cm^2$ of growth area). Cells were detached from the surface of the culture flasks by incubation in the presence of trypsin (1 ml/15 $cm^2$ of growth area) for 10 minutes. HASMC were detached using 0.15% trypsin while HAEC were detached using 0.1% trypsin. Following the incubation appropriate culture medium was added to the flasks (2× volume with respect to trypsin volume). The cell suspension was centrifuged at 200 g for 6 minutes followed by complete removal of supernatant solution. Cell pellets were resuspended in respective culture medium and counted using a hemacytometer. Appropriate volumes of HASMC and HAEC were combined to yield a mixed cell suspension containing 15% HAEC and remainder 85% HASMC (as a percentage of total cell population). The mixed cell suspension was centrifuged at 200 g for 5 minutes followed by complete removal of supernatant solution. Mixed cell pellets were resuspended in 6 ml of HASMC culture medium and transferred to 20 ml glass vials, followed by incubation on an orbital shaker at 150 rpm for 60 minutes, and at 37° C. and 5% $CO_2$. This allows the cells to aggregate with one another and initiate cell-cell adhesions. Post-incubation, the cell suspension was transferred to a 15 ml centrifuge tube and centrifuged at 200 g for 5 mins. After removal of the supernatant medium, the cell pellet was resuspended in 400 µl of HASMC culture medium and pipetted up and down several times to ensure all cell clusters were broken. The cell suspension was transferred into a 0.5 ml microfuge tube placed inside a 15 ml centrifuge tube followed by centrifugation at 2000 g for 4 minutes to form a highly dense and compact cell pellet. The supernatant medium was aspirated and the cells were transferred into capillary tubes (OD 1.0 mm, ID 0.5 mm, L 75 mm) by aspiration so as to yield cell cylinders 50 mm in length. The cell paste inside the capillaries was incubated in HASMC medium for 20 minutes at 37° C. and 5% $CO_2$. The cellular cylinders were then deposited from the capillary tubes into the grooves of the NovoGel™ mold (covered with HASMC medium) using the plunger supplied with the capillaries. The cellular cylinders were incubated for 24 hours at 37° C. and 5% $CO_2$.

Fabrication of HDF Cell Cylinders:

HDF cylinders were prepared using a method similar to preparing HASMC-HAEC mixed cellular cylinders. Briefly, the culture medium was removed from confluent HDF culture flasks and the cells were washed with DPBS (1 ml/5 $cm^2$ of growth area). Cells were detached from the surface of the culture flasks by incubation in the presence of trypsin (0.1%; 1 ml/15 $cm^2$ of growth area) for 10 minutes. Following the incubation HDF culture medium was added to the flasks (2× volume with respect to trypsin volume). The cell suspension was centrifuged at 200 g for 6 minutes followed by complete removal of supernatant solution. Cell pellets were resuspended in 6 ml of HDF culture medium and transferred to 20 ml glass vials, followed by incubation on an orbital shaker at 150 rpm for 75 minutes, and at 37° C. and 5% $CO_2$. Post-incubation, the cell suspension was transferred to a 15 ml centrifuge tube and centrifuged at 200 g for 5 minutes. After removal of the supernatant medium, the cell pellet was resuspended in 400 µl of HDF culture medium and pipetted up and down several times to ensure all cell clusters were broken. The cell suspension was transferred into a 0.5 ml microfuge tube placed inside a 15 ml centrifuge tube followed by centrifugation at 2000 g for 4 minutes to form a highly dense and compact cell pellet. The supernatant medium was aspirated and the cells were transferred into capillary tubes (OD 1.0 mm, ID 0.5 mm, L 75 mm) by aspiration so as to yield cell cylinders 50 mm in length. The cell paste inside the capillaries were incubated in HDF culture medium for 20 minutes at 37° C. and 5% $CO_2$. The cellular cylinders were then deposited from the capillary tubes into the grooves of the NovoGel™ mold (covered with HDF medium). The cellular cylinders were incubated for 24 hours at 37° C. and 5% $CO_2$.

Fabrication of Multi-Layered Vascular Tubes

Preparation of NovoGel™ Base Plate:

A NovoGel™ base plate was fabricated by dispensing 10 ml of pre-warmed (>40° C.) NovoGel™ (2% w/v) into a 10 cm Petri dish. Immediately after dispensing, the NovoGel™ was evenly spread so as to cover the entire base of the dish and form a uniform layer. The Petri dish was incubated at room temperature for 20 minutes to allow the NovoGel™ to gel completely.

Figure 5:
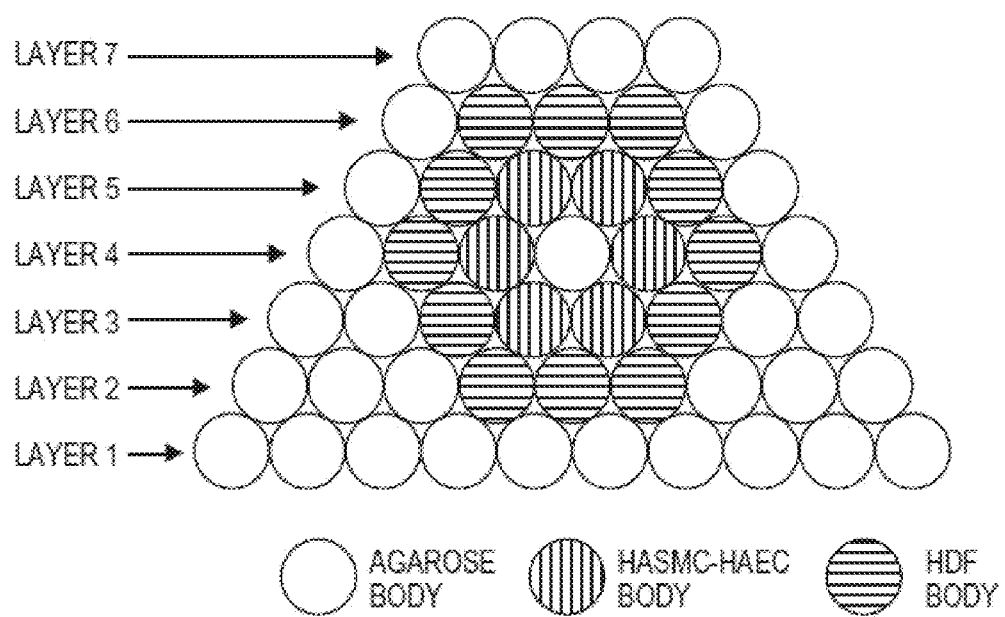
FIG. 5 illustrates a non-limiting example of a two-dimensional representation of a bio-printed tissue construct.

Multi-Layered Vascular Tube:

Vascular tubes consisting of an outer layer of HDF and an inner layer of HASMC-HAEC were fabricated utilizing HDF cylinders, and HASMC-HAEC mixed cell cylinders. A geometrical arrangement as shown in FIG. 5 was utilized. Briefly, at the end of the 24-hour incubation period mature HDF and HASMC-HAEC cylinders were aspirated back into the capillary tubes and placed in appropriate culture medium until further use. The support structure consisting of NovoGel™ rods was prepared as follows: Pre-warmed 2% NovoGel™ was aspirated into the capillary tubes (L=50 mm) and rapidly cooled in cold PBS solution (4° C.). The 5 cm long gelled NovoGel™ cylinder was deposited from the capillary (using the plunger) and laid down straight on the NovoGel™ base plate. A second NovoGel™ cylinder was adjoined to the first one and the process was repeated until 10 NovoGel™ cylinders were deposited to form the first layer. At this point 20 µl of PBS was dispensed above the NovoGel™ cylinders to keep them wet. Further six NovoGel™ cylinders were deposited on top of layer 1 at positions as shown in FIG. 5 (layer 2). Three HDF cylinders were then deposited at positions 4, 5, and 6 to complete layer 2. After dispensing each HDF cylinder 40 µl of HDF culture medium was dispensed on top of the deposited cylinder to assist the deposition of the subsequent cylinder as well as to prevent dehydration of the cellular cylinders. Next NovoGel™ cylinders for layer 3 were deposited followed by HDF cylinders at positions 3 and 6. Following rewetting of the structure with HDF culture medium, HASMC-HAEC mixed cylinders were laid down in positions 4 and 5. Subsequently, 40 µl of HASMC medium and 40 µl of HDF medium were dispensed on top of the cell cylinders. Layer 4 was completed by depositing NovoGel™ cylinders at positions 1 and 7, HDF cylinders at positions 2 and 6, HASMC-HAEC mixed cylinders at positions 3 and 5, and finally a 4% NovoGel™ cylinder at position 4. Layers 5, 6, and 7 were completed similarly by laying down NovoGel™ cylinders followed by HDF cylinders and finally HASMC-HAEC cylinders at positions shown in FIG. 5. Once the entire construct was completed 0.5 ml of warm NovoGel™ was dispensed over each end of the construct and allowed to gel at room temperature for 5 minutes. Following gelation of that NovoGel™, 30 ml of HASMC medium was added to the Petri dish (to ensure the entire construct was completely submerged). The construct was incubated for 24 hours at 37° C. and 5% $CO_2$ to allow for fusion between the cellular cylinders.

At the end of 24 hours, the surrounding NovoGel™ support structure was removed from the fused multi-layered vascular tube.

Example 3

Bioprinter

A bioprinter was assembled. The bioprinter contained a printer head having a collet chuck grip for holding a cartridge, and a piston for dispensing the contents of the cartridge. The cartridges used were glass microcapillary tubes having a length of 75-85 mm. A new capillary tube was loaded each time bio-ink or support material was required.

In order to print structures, a dispense position repeatability of ±20 µm was required for the duration of the printing process, i.e., when new capillaries were loaded into the printer head. In order to maintain repeatability of all loaded capillary tubes relative to the same point in the x-, y-, and z-directions, the bioprinter contained a laser calibration system for calibrating the position of the microcapillary tube. The laser calibration system calibrated the position of all capillary tips to a common reference location. All printing moves were made relative to this reference position.

All three axes (x-, y-, and z-axes) were calibrated through usage of a single laser distance measurement sensor. The system consisted of a laser sensor and a laser beam. The sensor threshold was the maximum sensing distance of the laser sensor. The sensor was configured to ignore all signals further away than a pre-defined threshold. The sensor used triangulation to determine distance to the object (the capillary tip). The laser sensor was orientated with the beam aimed vertically up (+z-axis).

Vertical Laser Calibration

For Calibration in the x-Axis:

The capillary tip was moved in the range of the laser sensor, with the tip to the left (−x) of the laser beam. The capillary was moved to in the +x direction until the sensor detected the capillary edge, and this position was recorded. The above steps were repeated from the opposite side (i.e., the tip was positioned at the right (+x) of the laser beam and moved in the −x direction until the sensor detected the capillary edge). The positions from both steps were averaged to calculate the mid-point of the capillary. Optionally, the above process was repeated for different y-positions and the calculated mid-points were averaged.

For Calibration in the y-Axis:

The above procedure (for the x-axis) was repeated for the y-axis.

For Calibration in the z-Axis:

The capillary tip was moved to above the sensor beam so that the bean hit the bottom surface of the capillary, and the tip was just outside of the sensor range threshold. The capillary was lowered until the sensor threshold was reached, and that position was recorded as the z-position. Optionally, the above steps were repeated at multiple points on the capillary tip surface and measured heights were averaged.

Horizontal Laser Calibration

For Calibration in the y-Axis:

The capillary was moved so that the tip was just below the laser beam height, and the capillary was off to one side (in the y-direction). The capillary was moved in the y-direction towards the laser. The capillary was stopped when the laser sensor detected the beam reflected off the capillary, and this position was recorded. The above steps were repeated with the capillary off to the other side of the laser, and moved in the −y direction). The mid-point from the above steps was recorded as the y-position.

For Calibration in the x-Axis:

Using the results of the calibration in the y-axis, the y-axis was moved so that the laser was centered on the capillary. The capillary was moved past the sensor threshold and moved towards the sensor. The capillary was stopped as soon as the capillary crossed the sensor threshold and the sensor output changed. This position, plus ½ the capillary width (from the y-calibration) was recorded as the x-position.

For Calibration in the z-Axis:

The capillary was moved up from the x-position until it was clear of the laser beam. The capillary tip was moved down towards the laser beam, and stopped as soon as the laser beam was interrupted (using the same process as for the y-axis). This position was recorded as the z-position.

Capillary Priming

Before printing from a capillary, the bio-ink or support material inside the capillary was primed so that the bio-ink or support material would begin printing at the very tip of the capillary. The calibration laser was used to prime the capillary. The capillary tip was moved just above the laser beam, with the beam centered in the y-axis. The tip was between 20-100 µm above the laser beam. The dispensing piston in the printer head was driven down until the bio-ink or support material started to dispense out of the capillary tip and interrupted the laser beam. The dispensed bio-ink or support material was aspirated back into the capillary tube by driving the piston in the reverse direction (20-100 µm). The capillary was then primed and ready to dispense.

NovoGel® Capillary Cleaning

NovoGel® was used as a support material. In order to remove excess NovoGel™ sticking to the outside surface of the capillary tube and to avoid the excess NovoGel™ from affecting print quality, the excess NovoGel® was removed. A wiping feature was integrated into a bulk NovoGel® vessel. A bulk NovoGel® vessel was fitted with a standard medical vial with an open cap for a septum to be attached. A septum was configured with a cross cut in the center of 1-2 mm thick silicone. By dipping the capillary into the bulk NovoGel® vessel through the septum and aspirating NovoGel® excess NovoGel® was wiped from the capillary as it exited the vessel, and remained in the bulk vessel.

Printing of a Vascular Structure

The bioprinter and cartridge was assembled as above. The bioprinter had a stage having a Petri dish for receiving structures generated by the bioprinter. The Petri dish was coated with NovoGel™.

A two dimensional representation (see e.g., FIG. 5) of a vascular structure was inputted by a user into a software program into a computer which was connected to the bioprinter. The two dimensional representation of the vascular structure consisted of rods of HASMC-HAEC mixed cellular cylinders, HDF cylinders, and NovoGel® rods defining the voids of the vascular structure and surrounding the vascular structure. HASMC-HAEC mixed cellular cylinders and HDF cellular cylinders were prepared as in Example 1, and aspirated into capillary tubes for insertion into the collet chuck of the printer head. Alternatively, capillary tubes were loaded into the printer head and dipped into the bulk NovoGel® vessel and NovoGel® was aspirated into the capillary tube. The capillary tubes were calibrated using the vertical laser calibration system.

When the commands from the software program were provided to the bioprinter, the bioprinter would print the three-dimensional structure, alternating between HASMC-HAEC rods, HDF rods and NovoGel® rods, onto the Petri dish, in predetermined locations. See Example 2. After each rod was laid down on the Petri dish, the rod was wetted with a small amount of culture medium. Once the entire construct was completed warm NovoGel® was dispensed over each end of the construct and allowed to gel at room temperature, and cell culture medium was added to the Petri dish to submerge the entire construct. The construct was then incubated at 37° C. and 5% $CO_2$ to allow for fusion between the cellular cylinders. At the end of the incubation time, the surrounding NovoGel® support structure was removed from the fused multi-layered vascular tube.

Example 4

Bioprinting of UV Cross-Linked PEG-DA

A solution of 10% (w/v) PEG-DA (Glycosan BioSystems, Inc.; Salt Lake City, Utah) in water is mixed with a curing agent (0.1% w/v PEGcure Photoinitiator) (Glycosan BioSystems, Inc.; Salt Lake City, Utah). The resultant solution is kept away from light in a vial chamber in a bioprinter. This solution is then aspirated using a 300 µm or 500 µm sized glass capillary via extrusion method and exposed to UV light (wavelength 365 nm, intensity 15,000-20,000 µW/cm$^2$) for at least 3 minutes to allow polymerization via cross-linking to occur. The cross-linking converts the liquid hydrogel into semi-solid structure. The semi-solid hydrogel is bioprintable with or without cells and be used to create geometrically complex structures such as sheets, sacs, tubes, conduits, cylinders, tissues, organs, etc.

Cross-Linked PEG-DA with Cells

In various applications, PEG-DA is used to encapsulate cells, proteins, or other biological material prior to being extruded from the bioprinter. For applications where a UV cross-linkable material (e.g., PEG-DA, etc.) including cells is bioprinted, an attenuation filter is added to the UV module to achieve reduced UV light intensities. In one application, the PEG-DA is exposed to UV light at an intensity and/or exposure time not optimal for full cross-linking. In a particular case, PEG-DA including mammalian cells was exposed to UV light with an intensity of 800 mW/cm$^2$ and the UV source at a distance of 2 inches away from the PEG-DA material. The degree of cross-linking is optionally controlled by altering the composition of UV cross-linkable material and photoinitiator. See Table 2.

TABLE 2

| Composition | Ratios | UV Exposure | Result |
|---|---|---|---|
| 5% PEGDA + 5% Irgacure 2959 | 1:100/1:50 | 6 minutes | <50% cross-linked |
| 5% PEGDA + 15% Irgacure 2959 | 1:100/1:50 | 6 minutes | <75% but >50% cross-linked |
| 5% PEGDA + 5%/ 15% Irgacure | 1:25 | 6 minutes | 100% cross-linked |

The bioprinter then prints successive layers of PEG-DA and cells in a structure where the cells are partially or completely encapsulated by the PEG-DA. Lastly, the entire structure is further exposed to UV to promote full cross-linking of the PEG-DA surrounding the cells. This procedure is optionally used to encapsulate other types of biological materials either in liquid or semi-solid state.

Cross-Linked PEG-DA without Cells

In another application, PEG-DA is used as the basis of a scaffold onto which cells and other material is bioprinted. A pre-formed PEG-DA structure is created via mechanical molding with exposure to UV light. For example, PEG-DA is dissolved in a 50 mM Tris HCL buffer and cross-linked using 5% Irgacure 2959 at a 1:250 dilution ratio. Long-wave UV light (i.e. 365 nm) with an intensity of 800 mW/cm$^2$ is utilized to achieve complete cross-linking in 5 minutes of exposure. The preformed PEG-DA structure is placed in the bioprinter and cells and other materials are printed onto the structure. Once the cells are printed, they are allowed to fuse and the PEG-DA scaffold is subsequently removed. This technique is capable of producing cellular structures in the shape of organs such as a bladder and other complex shapes.

Example 5

Bioprinting of UV Cross-Linked Methacrylated Hydrogel

Cross-linked methacrylated hydrogel is bioprinted from a NovoGen MMX™ Bioprinter including a UV module using the following parameters:
Hydrogel Concentration: 5%
Irgacure 2959 Concentration: 0.5%
UV Intensity: 1.50 W/cm$^2$
UV Exposure Time: 15 sec
Dispense Height: 0.5 mm (1×D using a 500 µm capillary)

Optionally, a longer exposure time is used in combination with a lower UV intensity. Because some methacrylated hydrogels expand to a bioprintable length approximately 40% longer than the aspiration amount, a variable pump speed dispense command is configured to dispense a shorter length of material from the dispense pump at a slower speed than the actual robot axes movements. To print a 50 mm long piece of methacrylated hydrogel in the +Y axis at 2 mm/sec. The following calculations are made to determine the correct amount of material to aspirate and the corresponding pump speed to result in a 50 mm line:

Calculate the amount of methacrylated hydrogel to aspirate: 50 mm/1.4=35.71 mm

Calculate pump speed: 2 mm/sec/1.4=1.43 mm/sec

The bioprinter software script commands are configured as follows:

Aspirates 35.71 mm of fluid and then moves to the UV exposure chamber for 15 seconds.

Moves the gel capillary to the zero point at a dispense height of 0.5 mm.

Moves the robot 50 mm in the Y-axis at a speed of 2 mm/sec and moves the gel dispense pump 35.71 mm at a speed of 1.43 mm/sec. The gel pump and Y-axis should stop at the same time, resulting in a 50 mm line.

Example 6

Coaxial Nozzle—Varying Flow Rates

Figure 29:
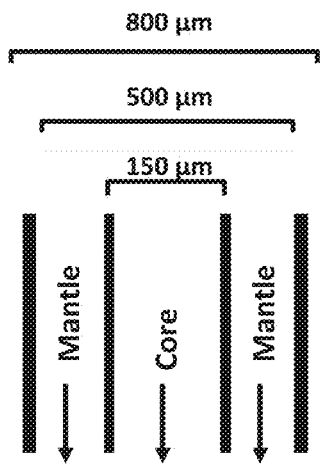
FIG. 29 illustrates a non-limiting example of the specifications for a coaxial nozzle.

Nozzle modification allows for spatial portioning of cell types, materials, and/or mixtures of cells. This experiment investigates the use of model compounds of a given viscosity extruded through the nozzle at a variety of flow rates in order to assess optimal condition for minimizing mantle-core mixing due to volumetric outflow mismatch. Specifications for the nozzle were as follows: inner diameter of nozzle for bio-ink flow of the core layer: 150 µm; inner diameter of nozzle for bio-ink flow of the mantle layer: 500 µm; outer diameter of the nozzle: 800 µm (see FIG. 29). The materials were initially a blue-tinted 30% P-F127 and clear 30% P-F127. Later, because of rapid diffusional normalization of the blue tint, an opaque viscous proteinaceous material with viscosity similar to P-F127 was employed. Assessment was qualitatively determined by the naked eye for proper mantle/core formation. Results are shown below. Higher flow rates induced flow instability and therefore should be considered the upper limit of sustainable flow for the nozzle and bio-inks of this experiment.

| | Core Flow (mL/h) | Mantle Flow (mL/h) | Qualitative result |
|---|---|---|---|
| 1 | 4 | 4 | Core and mantle side by side, asymmetrical positioning |
| 2 | 6 | 4 | Coaxial structure, but mantle is too thin |
| 3 | 8 | 4 | Good formation of mantle thickness, symmetrical |
| 4 | 10 | 4 | Instability forms, oscillation in flows |

Figure 30:
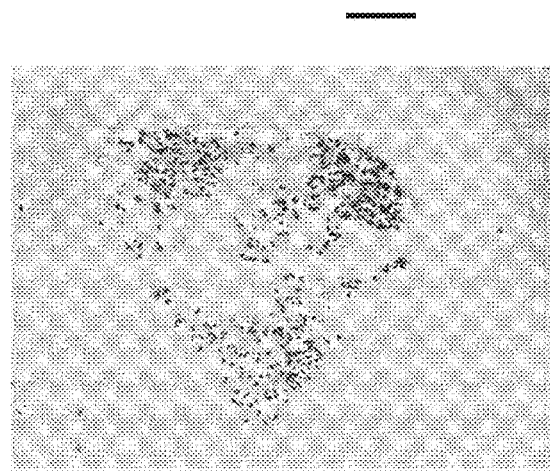
FIG. 30 illustrates a non-limiting example of a coaxial tube with a cell-containing core layer and cell-free mantle layer extruded from a coaxial nozzle; in this case, histology of a cross section illustrates compact cell core structure.

A follow-up experiment was conducted with 1% alginate as the mantle material, with model cells (NIH3T3) comprising the core layer. Flow rates were determined from the initial experiment. Expected bulk morphological results (H & E staining) are shown in FIG. 30, indicating that the compact cell core remains intact after extrusion.

Both sets of experiments demonstrate the feasibility of the production of complex bilayer structures using a coaxial nozzle. Variations in volumetric flow rates to the mantle and core impacted the morphological outcome of the extruded components, but utilizing a core flow that was approximately twice that of the mantle flow generated a stable structure.

Example 7

Coaxial Nozzle—Printing of Vascular Vessels

The functionality of a coaxial nozzle (specifications for the nozzle: inner diameter of nozzle for bio-ink flow of the core layer: 514 µm; inner diameter of nozzle for bio-ink flow of the mantle layer: 819 µm; outer diameter of the nozzle: 3200 µm) was tested on a non-cellular material-only system. An alginate gelatin mixture was extruded through the outer nozzle around Novogel-containing calcium chloride extruded through the center. The presence of the calcium chloride in the center was sufficient to crosslink the outer shell. The Novogel was flushed out with PBS by manual use of a syringe and needle. Once verified in the material-only system, a cell/alginate/gelatin mixture was extruded to create a hollow tube (inner diameter 820 µm, outer diameter 2300 µm). The extruded cell/material tube was flushed to establish patency, and then segmented into six 50 mm tubes. Tubes were cultured both under static and flow conditions.

In a subsequent experiment, 50:50 normal human lung fibroblasts (NHLFs): human pulmonary endothelial cells (HPAECs) bio-ink was utilized in the printing of vascular vessels. It was hypothesized that creation of a strong oxygen gradient (high outside the vessel/low inside the vessel) would reverse the undesirable effect seen previously where the HPAECs automatically migrated to the abluminal surface of the vessel under standard conditioning protocols. FC40, an oxygen carrier, was utilized in conjunction with aerated media in order to generate a high oxygen abluminal compartment in the bioreactor. Two (6×1) vessels of aforementioned composition were printed and conditioned under the high abluminal oxygen conditions for 5 days. At day 5 the vessels were fixed and given for histological analysis.

Figure 31:
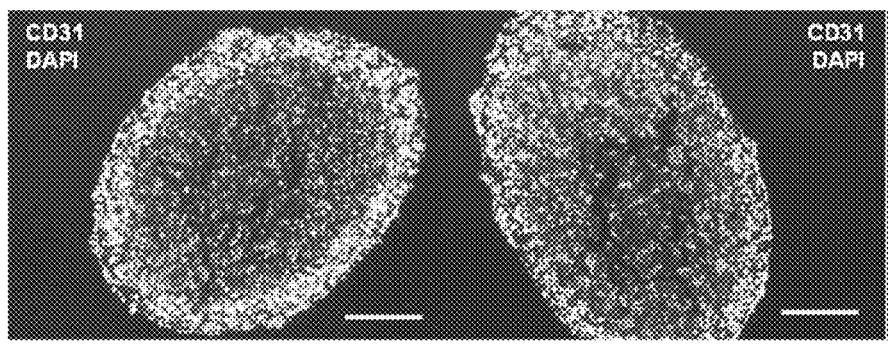
FIG. 31 illustrates a non-limiting example of six-day old bio-printed vascular vessels using 50:50 normal human lung fibroblasts:human pulmonary endothelial cells; in this example, two separate views of CD31 stained cross-sections of the vessel show migration of almost all the endothelial cells to the lumen of the vessel. All scale bars represent 200 microns.

Resulting compartmentalization of HAPECs in response to the high abluminal oxygen gradient is seen in FIG. 31. CD31 staining clearly showed mass migration of HPAECs into the lumen of the vessel, compared with previous results (not shown here) indicating that in the absence of such a gradient, HPAEC preference is to migrate to and to colonize the abluminal surface of the vessel.

These results suggest that the oxygen gradient method can be utilized for this particular cell type (HPAECs) to force migration of cells to the inner compartment, or (in using a reverse gradient) to the outer compartment. The technique of driving cells to a specific compartment can be utilized not only in tubular elements or spherical elements, but in other geometric constructions.

Example 8

Coaxial Nozzle—Bioprinting with I-Bio-Ink

Experiment 1:

With a cellular admixture consisting of 70% normal human lung fibroblasts (NHLFs): 20% bronchial smooth muscle cells (BSMCs): 10% human adipose derived mesenchymal stem cells (ADSCs), 500-µm diameter bio-printed vessels were generated and evaluated qualitatively at 12 hours for cohesion, surface smoothness (a sign of proper intra-bio-ink fusion), shortening (contraction), and ability to form tubular structures through standard bio-printing protocols (a sign of inter-bio-ink fusion). After assessment, vessels were embedded in a bioactive hydrogel and perfused with pulsatile flow. Following time on the bioreactor, the hydrogel with embedded vessels was sent for histological examination which demonstrated expected cellularity and morphology.

Figure 32:
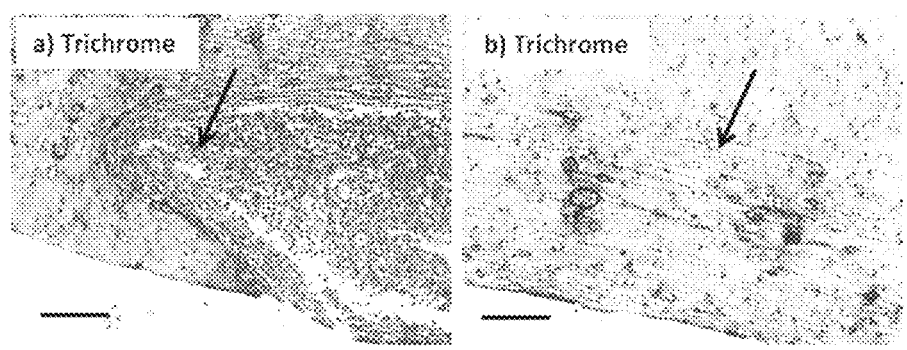
FIG. 32 illustrates a non-limiting example of coaxial structures using I-bio-ink; in this case, histology of embedded tubular structure and surrounding hydrogel is observed.

Qualitative assessment showed no discernible difference from similar bio-ink admixtures that did not contain ADSCs. Surface characterization of bio-ink was smooth and opaque. Bio-ink cylinders, when handled, were resilient—indicative of good cohesion. Contraction (shortening) was on the order of 50%, which is consistent for bio-ink generated in cylindrical shapes. Three bioprinted vessels (ID 500 µm/OD 1500 µm) were fused and patent (i.e., open and non-occluded) at 12 hours. Two representative vessels were conditioned in a hydrogel on a bioreactor for 3 days. Histological assessment showed consistency with previous non-MSC containing specimens. Example histology of embedded tubular structure and surrounding hydrogel is shown in FIG. 32.

Experiment 2:

With two cellular admixtures [50% normal human lung fibroblasts (NHLFs): 40% human pulmonary artery endothelial cells (HPAECs): 10% human adipose derived mesenchymal stem cells (ADSCs); 50% normal human lung fibroblasts (NHLFs): 45% human pulmonary artery endothelial cells (HPAECs): 5% human adipose derived mesenchymal stem cells (ADSCs)], 500-µm diameter bio-printed vessels were generated and evaluated qualitatively at 12 hours for cohesion, surface smoothness (a sign of proper intra-bio-ink fusion), shortening (contraction), and ability to form tubular structures through standard bioprinting protocols (a sign of inter-bio-ink fusion). Representative samples were perfused in a bioreactor. Samples from these groups were submitted for histology with staining for morphology (H&E), apoptosis (TUNEL), proliferation (ki67), smooth muscle cell actin, endothelial marker (CD31), fibroblast marker (TE7), and extracellular matrix deposition (Trichrome).

Qualitative assessment showed no discernible difference from similar bio-ink admixtures that did not contain ADSCs. Surface characterization of bio-ink was smooth and opaque. Bio-ink cylinders, when handled, were resilient—indicative of good cohesion. Contraction (shortening) was on the order of 50% which is consistent for bio-ink generated in cylindrical shapes. Lastly, four bioprinted vessels (ID 500 µm/OD 1500 µm) were fused and patent (i.e., open and non-occluded) at 12 hours. Two vessels that were loaded into the bioreactor were from the 50% NHLF: 45% HPAEC: 5% ADSC group due to their exceptional quality. Conditioning with pulsatile flow occurred for 9 days and vessels were histologically analyzed as described above. Resulting histology showed qualitatively no difference with control constructs generated from bio-ink without immunomodulatory cells.

Experiment 3:

With a cellular admixture consisting of 75% human adipose derived mesenchymal stem cells (ADSCs): 25% human artery endothelial cells (HAECs), 500-µm diameter bio-printed vessels were generated and evaluated qualitatively at 12 hours for cohesion, surface smoothness (a sign of proper intra-bio-ink fusion) and shortening (contraction). This same cellular admixture was also evaluated for ability to form patch structures (5 mm×5 mm) through standard bioprinting protocols (a sign of inter-bio-ink fusion). Samples from these groups were submitted for histology with staining for morphology (H&E) & apoptosis (TUNEL).

Figure 33:
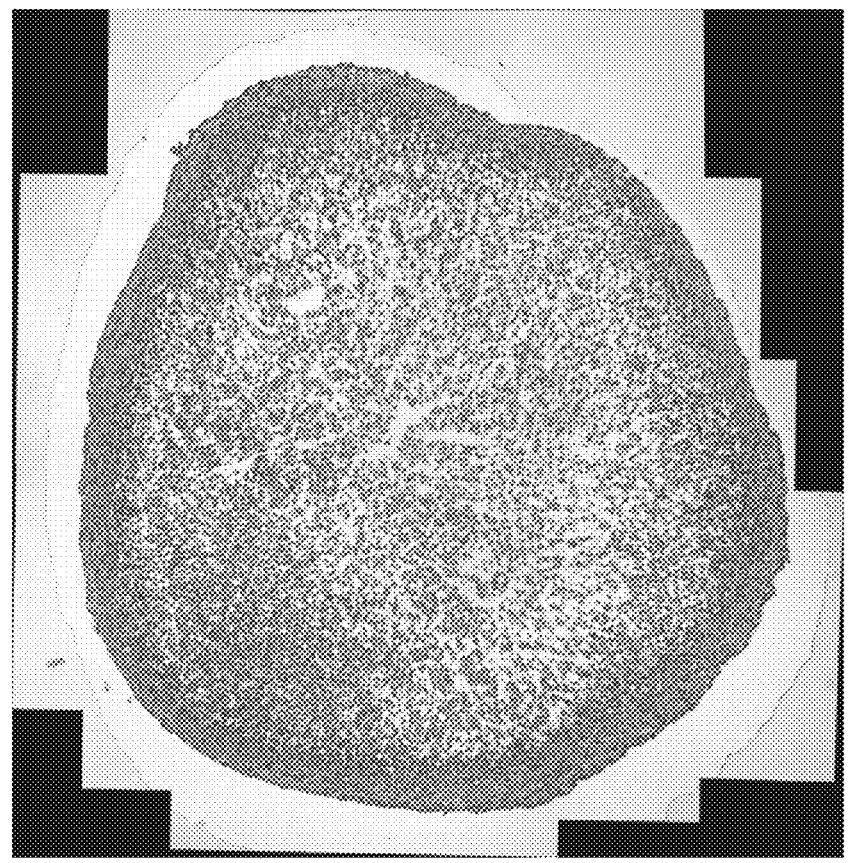
FIG. 33 illustrates a non-limiting example of a patch created with I-bio-ink; in this case, histology is shown using H & E staining.

Qualitative assessment showed no discernible difference from similar bio-ink admixtures that did not contain ADSCs. Surface characterization of bio-ink was smooth and opaque. Bio-ink cylinders, when handled, were resilient—indicative of good cohesion. Contraction (shortening) was on the order of 50% which is consistent for bio-ink generated in cylindrical shapes. Lastly, four bioprinted patches (5 mm×5 mm) were fused and patent (i.e., open and non-occluded) at 12 hours. The patches were submitted for histology after 2 days. An example patch is shown in FIG. 33.

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

What is claimed is:

1. A bioprinter comprising one or more coaxial nozzles with an N-value of two or more configured to control the deposition of materials to form one or more constructs having a pre-determined three-dimensional geometry, wherein each coaxial nozzle has concentric flow wherein each coaxial nozzle comprises at least two independent inputs for at least two different materials and at least two independent outputs configured to prepare a coaxial tube comprising a core layer and a mantle layer, any two adjacent layers having a different composition of materials with respect to each other, and the materials being selected from a bio-ink, or a combination of bio-ink and support material, wherein the bio-ink comprises living cells.

2. The bioprinter of claim 1, wherein each of the one or more coaxial nozzles further comprises a means to independently regulate the flow of each of the at least two different materials through the at least two independent outputs.

3. The bioprinter of claim 2, wherein the means to independently regulate the flow of each of the at least two different materials through the at least two independent outputs allows for continuous extrusion or sputter extrusion, wherein sputter extrusion is the stopping and starting of the flow through at least one of the at least two independent outputs.

4. The bioprinter of claim 2, wherein the means to independently regulate the flow of each of the at least two different materials produces a flow rate for at least one of the materials of about 0.1 to about 1 ml/min.

5. The bioprinter of claim 1, wherein one of the at least two different materials is removed after bioprinting to create one or more voids.

6. The bioprinter of claim 1, wherein the one or more coaxial nozzles has an N-value of three or more.

7. The bioprinter of claim 6, comprising three independent inputs for three different materials and three independent outputs for the preparation of a coaxial tube with a core layer, a mantle layer, and an intermediate layer, the intermediate layer between the core layer and the mantle layer.

8. The bioprinter of claim 1, wherein the one or more coaxial nozzles are configured to produce a core layer that is about 150 µm in diameter and a mantle layer that is about 500 µm in diameter.

9. The bioprinter of claim 1, comprising four independent inputs for four different materials and four independent outputs configured to prepare a coaxial tube with a core layer, a mantle layer, and at least two intermediate layers.

10. The bioprinter of claim 1, configured to prepare any of the one or more constructs with a three-dimensional geometry that is a cylinder, hollow cylinder, polygon, sheet, or sphere.

11. The bioprinter of claim 1, wherein the bio-ink, or the bio-ink and the support material are a solid or semi-solid.

12. The bioprinter of claim 1, wherein the bioprinter deposits the materials by application of pressure to extrude the materials though an orifice.

* * * * *